(12) United States Patent
Fitz et al.

(10) Patent No.: US 9,216,025 B2
(45) Date of Patent: *Dec. 22, 2015

(54) JOINT ARTHROPLASTY DEVICES AND SURGICAL TOOLS

(75) Inventors: Wolfgang Fitz, Sherborn, MA (US); Philipp Lang, Lexington, MA (US); Daniel Steines, Lexington, MA (US); Konstantinos Tsougarakis, San Francisco, CA (US); Rene Vargas-Voracek, Sunnyvale, CA (US)

(73) Assignee: ConforMIS, Inc., Bedford, MA (US)

( * ) Notice: Subject to any disclaimer, the term of this patent is extended or adjusted under 35 U.S.C. 154(b) by 638 days.

This patent is subject to a terminal disclaimer.

(21) Appl. No.: 13/405,797

(22) Filed: Feb. 27, 2012

(65) Prior Publication Data

US 2012/0197260 A1     Aug. 2, 2012

Related U.S. Application Data

(63) Continuation of application No. 12/606,830, filed on Oct. 27, 2009, now Pat. No. 8,377,129, which is a continuation of application No. 10/724,010, filed on Nov. 25, 2003, now Pat. No. 7,618,451, which is a (Continued)

(51) Int. Cl.
*A61B 17/56*     (2006.01)
*A61B 17/17*     (2006.01)

(Continued)

(52) U.S. Cl.
CPC .......... *A61B 17/1739* (2013.01); *A61B 5/4528* (2013.01); *A61B 17/15* (2013.01);

(Continued)

(58) Field of Classification Search
CPC .. A61B 17/1739; A61B 5/4528; A61B 17/15; A61B 17/155; A61B 17/157; A61B 17/158; A61B 17/1666; A61B 17/1668; A61B 17/1671; A61B 19/5244; A61B 17/16; A61B 17/1675; A61B 17/1764; A61B 5/4504; A61B 17/7098; A61B 17/8805; A61B 19/50; A61B 2019/461; A61B 2019/502; A61B 2019/505; A61B 2019/508; A61B 2019/566; A61B 5/4514; A61F 2/30756; A61F 2/30942; A61F 2/4657; A61F 2/30767; A61F 2/36; A61F 2/3859; A61F 2002/30062; A61F 2002/30677; A61F 2002/30787; A61F 2002/30841; A61F 2002/30894; A61F 2002/30948; A61F 2002/3095; A61F 2002/30957; A61F 2002/30962; A61F 2002/3097; A61F 2002/4631; A61F 2210/0004; A61F 2310/00011; A61F 2310/00017; A61F 2310/00023; A61F 2310/00029; A61F 2310/00047; A61F 2310/00065; A61F 2310/00071; A61F 2310/00077; A61F 2310/00083; A61F 2310/00107; A61F 2310/00113; A61F 2310/00119; A61F 2310/00131; A61F 2310/00143; A61F 2310/00149; A61F 2310/00155; A61F 2310/00293; A61F 2310/00383; A61F 2310/00395; A61F 2310/00592; B23Q 17/00
USPC .............. 606/79–85, 86 A, 86 R, 87–89
See application file for complete search history.

(56) References Cited

U.S. PATENT DOCUMENTS 3,314,420 A    4/1967  Smith et al. ............... 128/92
3,605,123 A    9/1971  Hahn ............................. 3/1

(Continued)

FOREIGN PATENT DOCUMENTS

DE     2306552      8/1974     ............... A61F 1/00
DE     3516743     11/1986     ............... A61F 2/36

(Continued)

OTHER PUBLICATIONS

Andersson et al., "MacIntosh Arthroplasty in Rheumatoid Arthritis," Acta. Orthop. Scand. 45(2):245-259 (1974).

(Continued)

*Primary Examiner* — Pedro Philogene
(74) *Attorney, Agent, or Firm* — Sunstein Kann Murphy & Timbers LLP

(57) ABSTRACT

Disclosed herein are methods, compositions and tools for repairing articular surfaces repair materials and for repairing an articular surface. The articular surface repairs are customizable or highly selectable by patient and geared toward providing optimal fit and function. The surgical tools are designed to be customizable or highly selectable by patient to increase the speed, accuracy and simplicity of performing total or partial arthroplasty.

20 Claims, 36 Drawing Sheets

Related U.S. Application Data continuation-in-part of application No. 10/305,652, filed on Nov. 27, 2002, now Pat. No. 7,468,075, which is a continuation-in-part of application No. 10/160,667, filed on May 28, 2002.

(60) Provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002.

(51) Int. Cl.

| | |
|---|---|
| *A61B 17/15* | (2006.01) |
| *A61B 17/16* | (2006.01) |
| *A61F 2/30* | (2006.01) |
| *A61F 2/46* | (2006.01) |
| *B23Q 17/00* | (2006.01) |
| *A61B 5/00* | (2006.01) |
| *A61B 17/70* | (2006.01) |
| *A61B 17/88* | (2006.01) |
| *A61B 19/00* | (2006.01) |
| *A61F 2/36* | (2006.01) |
| *A61F 2/38* | (2006.01) |
| *A61B 6/00* | (2006.01) |

(52) U.S. Cl.
CPC ............ *A61B 17/155* (2013.01); *A61B 17/157* (2013.01); *A61B 17/158* (2013.01); *A61B 17/16* (2013.01); *A61B 17/1666* (2013.01); *A61B 17/1668* (2013.01); *A61B 17/1671* (2013.01); *A61B 17/1675* (2013.01); *A61B 17/1764* (2013.01); *A61B 19/5244* (2013.01); *A61F 2/30756* (2013.01); *A61F 2/30942* (2013.01); *A61F 2/4657* (2013.01); *B23Q 17/00* (2013.01); *A61B 5/4504* (2013.01); *A61B 5/4514* (2013.01); *A61B 6/508* (2013.01); *A61B 17/7098* (2013.01); *A61B 17/8805* (2013.01); *A61B 19/50* (2013.01); *A61B 2019/461* (2013.01); *A61B 2019/502* (2013.01); *A61B 2019/505* (2013.01); *A61B 2019/508* (2013.01); *A61B 2019/566* (2013.01); *A61F 2/30767* (2013.01); *A61F 2/36* (2013.01); *A61F 2/3859* (2013.01); *A61F 2002/30062* (2013.01); *A61F 2002/3095* (2013.01); *A61F 2002/3097* (2013.01); *A61F 2002/30677* (2013.01); *A61F 2002/30787* (2013.01); *A61F 2002/30841* (2013.01); *A61F 2002/30894* (2013.01); *A61F 2002/30948* (2013.01); *A61F 2002/30957* (2013.01); *A61F 2002/30962* (2013.01); *A61F 2002/4631* (2013.01); *A61F 2210/0004* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01); *A61F 2310/00065* (2013.01); *A61F 2310/00071* (2013.01); *A61F 2310/00077* (2013.01); *A61F 2310/00083* (2013.01); *A61F 2310/00107* (2013.01); *A61F 2310/00113* (2013.01); *A61F 2310/00119* (2013.01); *A61F 2310/00131* (2013.01); *A61F 2310/00143* (2013.01); *A61F 2310/00149* (2013.01); *A61F 2310/00155* (2013.01); *A61F 2310/00293* (2013.01); *A61F 2310/00383* (2013.01); *A61F 2310/00395* (2013.01); *A61F 2310/00592* (2013.01); *Y10T 29/49* (2015.01); *Y10T 29/49764* (2015.01); *Y10T 29/49778* (2015.01)

(56) References Cited

U.S. PATENT DOCUMENTS

| | | | |
|---|---|---|---|
| 3,798,679 A | 3/1974 | Ewald | 3/1 |
| 3,808,606 A | 5/1974 | Tronzo | 3/1 |
| 3,843,975 A | 10/1974 | Tronzo | 3/1 |
| 3,855,638 A | 12/1974 | Pilliar | 3/1 |
| 3,938,198 A | 2/1976 | Kahn et al. | 3/1.912 |
| 3,987,499 A | 10/1976 | Scharbach et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |
| 4,203,444 A | 5/1980 | Bonnell et al. | 128/276 |
| 4,213,816 A | 7/1980 | Morris | 156/245 |
| 4,340,978 A | 7/1982 | Buechel et al. | 3/1.911 |
| 4,368,040 A | 1/1983 | Weissman | 433/36 |
| 4,436,684 A | 3/1984 | White | 264/138 |
| 4,501,266 A | 2/1985 | McDaniel | 128/69 |
| 4,502,161 A | 3/1985 | Wall | 3/1.91 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,886,258 A | 12/1989 | Scott | 269/328 |
| 4,936,862 A | 6/1990 | Walker et al. | 623/23 |
| 4,979,949 A | 12/1990 | Matsen, III et al. | 606/53 |
| 5,002,547 A | 3/1991 | Poggie et al. | 606/88 |
| 5,007,936 A | 4/1991 | Woolson | 623/23 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/20 |
| 5,067,964 A | 11/1991 | Richmond et al. | 623/18 |
| 5,122,144 A | 6/1992 | Bert et al. | 606/88 |
| 5,129,908 A | 7/1992 | Petersen | 606/88 |
| 5,133,759 A | 7/1992 | Turner | 623/20 |
| 5,154,717 A | 10/1992 | Matsen, III et al. | 606/53 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,246,530 A | 9/1993 | Bugle et al. | 156/643 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,299,288 A | 3/1994 | Glassman et al. | 395/80 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,344,459 A | 9/1994 | Swartz | 623/18 |
| 5,360,446 A | 11/1994 | Kennedy | 623/16 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/88 |
| 5,403,319 A | 4/1995 | Matsen, III et al. | 606/88 |
| 5,437,676 A | 8/1995 | Bouraly et al. | 606/88 |
| 5,452,407 A | 9/1995 | Crook | 395/121 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |

(56) References Cited

U.S. PATENT DOCUMENTS

| | | | |
|---|---|---|---|
| 5,501,687 A | 3/1996 | Willert et al. | 606/94 |
| 5,503,162 A | 4/1996 | Athanasiou et al. | 128/774 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,291 A | 8/1997 | Techiera | 606/80 |
| 5,671,741 A | 9/1997 | Lang et al. | 128/653.2 |
| 5,681,316 A | 10/1997 | DeOrio et al. | 606/88 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,690,637 A | 11/1997 | Wen et al. | 606/88 |
| 5,728,162 A | 3/1998 | Eckhoff | 623/20 |
| 5,735,277 A | 4/1998 | Schuster | 128/653.1 |
| 5,737,506 A | 4/1998 | McKenna et al. | 395/125 |
| 5,741,215 A | 4/1998 | D'Urso | 600/407 |
| 5,749,874 A | 5/1998 | Schwartz | 606/75 |
| 5,749,876 A | 5/1998 | Duvillier et al. | 606/88 |
| 5,766,259 A | 6/1998 | Sammarco | 623/21 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,795,353 A | 8/1998 | Felt | 623/18 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,297 A | 3/1999 | Matsen, III | 606/87 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/88 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,296,646 B1 | 10/2001 | Williamson | 606/90 |
| 6,299,905 B1 | 10/2001 | Peterson et al. | 424/486 |
| 6,322,588 B1 | 11/2001 | Ogle et al. | 623/1.46 |
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,478,799 B1 | 11/2002 | Williamson | 606/90 |
| 6,479,996 B1 | 11/2002 | Hoogeveen et al. | 324/309 |
| 6,510,334 B1 | 1/2003 | Schuster et al. | 600/407 |
| 6,520,964 B2 | 2/2003 | Tallarida et al. | 396/567 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,589,281 B2 | 7/2003 | Hyde, Jr. | 623/18.11 |
| 6,620,168 B1 | 9/2003 | Lombardo et al. | 606/88 |
| 6,626,945 B2 | 9/2003 | Simon et al. | 623/17.19 |
| 6,626,948 B2 | 9/2003 | Storer et al. | 623/23.14 |
| 6,632,225 B2 | 10/2003 | Sanford et al. | 606/87 |
| 6,632,235 B2 | 10/2003 | Weikel et al. | 606/192 |
| 6,652,587 B2 | 11/2003 | Felt et al. | 623/20.16 |
| 6,673,077 B1 | 1/2004 | Katz | 606/88 |
| 6,673,116 B2 | 1/2004 | Reiley | 623/21.18 |
| 6,679,917 B2 | 1/2004 | Ek | 623/20.14 |
| 6,702,821 B2 | 3/2004 | Bonutti | 606/88 |
| 6,712,856 B1 * | 3/2004 | Carignan et al. | 623/20.35 |
| 6,875,218 B2 | 4/2005 | Dye et al. | 606/91 |
| 6,905,514 B2 | 6/2005 | Carignan et al. | 623/20.35 |
| 6,916,341 B2 | 7/2005 | Rolston | 623/20.3 |
| 6,928,742 B2 | 8/2005 | Broers et al. | 33/512 |
| 6,969,393 B2 | 11/2005 | Pinczewski et al. | 606/88 |
| 6,984,249 B2 | 1/2006 | Keller | 623/20.24 |
| 7,008,430 B2 | 3/2006 | Dong et al. | 606/80 |

(56) References Cited

U.S. PATENT DOCUMENTS

| | | | |
|---|---|---|---|
| 7,048,741 B2 | 5/2006 | Swanson | 606/88 |
| 7,060,074 B2 | 6/2006 | Rosa et al. | 606/88 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,282,054 B2 | 10/2007 | Steffensmeier et al. | 606/96 |
| 7,292,674 B2 | 11/2007 | Lang | 378/54 |
| 7,379,529 B2 | 5/2008 | Lang | 378/54 |
| 7,442,196 B2 | 10/2008 | Fisher et al. | 606/88 |
| 7,467,892 B2 | 12/2008 | Lang et al. | 378/207 |
| 7,468,075 B2 | 12/2008 | Lang et al. | 623/16.11 |
| 7,534,263 B2 | 5/2009 | Burdulis, Jr. et al. | 623/14.12 |
| 7,603,192 B2 | 10/2009 | Martin et al. | 700/98 |
| 7,615,054 B1 | 11/2009 | Bonutti | 606/88 |
| 7,618,451 B2 * | 11/2009 | Berez et al. | 623/14.12 |
| 7,695,477 B2 | 4/2010 | Creger et al. | 606/87 |
| 7,742,801 B2 * | 6/2010 | Neubauer et al. | 600/411 |
| 7,747,305 B2 | 6/2010 | Dean et al. | 600/407 |
| 7,758,651 B2 | 7/2010 | Chauhan et al. | 623/20.18 |
| 7,806,896 B1 | 10/2010 | Bonutti | 606/86 R |
| 7,833,275 B2 | 11/2010 | Mears et al. | 623/22.11 |
| 7,881,768 B2 | 2/2011 | Lang et al. | 600/407 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 * | 11/2011 | Lang et al. | 606/87 |
| 8,066,708 B2 | 11/2011 | Lang et al. | 606/88 |
| 8,083,745 B2 * | 12/2011 | Lang et al. | 606/87 |
| 8,092,462 B2 | 1/2012 | Pinczewski et al. | 606/88 |
| 8,105,330 B2 * | 1/2012 | Fitz et al. | 606/88 |
| 8,109,942 B2 | 2/2012 | Carson | 606/130 |
| 8,112,142 B2 | 2/2012 | Alexander et al. | 600/407 |
| 8,122,582 B2 * | 2/2012 | Burdulis et al. | 29/527.1 |
| 8,123,753 B2 | 2/2012 | Poncet | 606/87 |
| RE43,282 E | 3/2012 | Alexander et al. | 600/427 |
| 8,167,888 B2 | 5/2012 | Steffensmeier | 606/88 |
| 8,231,634 B2 * | 7/2012 | Mahfouz et al. | 606/102 |
| 8,234,097 B2 | 7/2012 | Steines et al. | 703/1 |
| 8,257,360 B2 | 9/2012 | Richard et al. | 606/88 |
| 8,265,730 B2 | 9/2012 | Alexander et al. | 600/410 |
| 8,306,601 B2 | 11/2012 | Lang et al. | 600/407 |
| 8,337,501 B2 | 12/2012 | Fitz et al. | 606/86 R |
| 8,337,503 B2 | 12/2012 | Lian | 606/87 |
| 8,337,507 B2 | 12/2012 | Lang et al. | 606/102 |
| 8,343,218 B2 | 1/2013 | Lang et al. | 623/16.11 |
| 8,357,166 B2 | 1/2013 | Aram et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,066 B2 | 2/2013 | Katrana et al. | 606/86 |
| 8,377,068 B2 | 2/2013 | Aker et al. | 606/87 |
| 8,377,073 B2 * | 2/2013 | Wasielewski | 606/102 |
| 8,377,129 B2 * | 2/2013 | Fitz et al. | 623/14.12 |
| 8,439,926 B2 * | 5/2013 | Bojarski et al. | 606/88 |
| 8,460,304 B2 * | 6/2013 | Fitz et al. | 606/88 |
| 8,480,754 B2 | 7/2013 | Bojarski et al. | 623/20.35 |
| 8,500,740 B2 | 8/2013 | Bojarski et al. | 606/86 R |
| 8,529,568 B2 | 9/2013 | Bouadi | 606/84 |
| 8,529,630 B2 | 9/2013 | Bojarski et al. | 623/20.14 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 * | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,617,172 B2 | 12/2013 | Fitz et al. | 606/88 |
| 8,617,242 B2 | 12/2013 | Philipp | 623/16.11 |
| 8,623,026 B2 | 1/2014 | Wong et al. | 606/96 |
| 8,634,617 B2 | 1/2014 | Tsougarakis et al. | 382/128 |
| 8,638,998 B2 | 1/2014 | Steines et al. | 382/128 |
| 8,641,716 B2 | 2/2014 | Fitz et al. | 606/80 |
| 8,657,827 B2 | 2/2014 | Fitz et al. | 606/87 |
| 8,682,052 B2 | 3/2014 | Fitz et al. | 382/131 |
| 8,690,945 B2 | 4/2014 | Fitz et al. | 623/16.11 |
| 8,709,089 B2 | 4/2014 | Lang et al. | 623/18.11 |
| 8,735,773 B2 | 5/2014 | Lang | 219/121.72 |
| 8,768,028 B2 | 7/2014 | Lang et al. | 382/131 |
| 8,771,365 B2 | 7/2014 | Bojarski et al. | 623/20.32 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0029038 A1 | 3/2002 | Haines | 606/54 |
| 2002/0045940 A1 | 4/2002 | Giannetti et al. | 623/11.11 |
| 2002/0059049 A1 | 5/2002 | Bradbury et al. | 703/11 |
| 2002/0068979 A1 | 6/2002 | Brown et al. | 623/20.3 |
| 2002/0072821 A1 | 6/2002 | Baker | 700/98 |
| 2002/0079601 A1 | 6/2002 | Russell et al. | 264/40.1 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0151986 A1 | 10/2002 | Asculai et al. | 424/484 |
| 2002/0156150 A1 | 10/2002 | Williams et al. | 623/23.75 |
| 2002/0173852 A1 | 11/2002 | Felt et al. | 623/20.32 |
| 2002/0183850 A1 | 12/2002 | Felt et al. | 623/20.16 |
| 2003/0028196 A1 | 2/2003 | Bonutti | 606/87 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0069591 A1 | 4/2003 | Carson et al. | 606/130 |
| 2003/0100907 A1 | 5/2003 | Rosa et al. | 606/86 |
| 2003/0100953 A1 | 5/2003 | Rosa et al. | 623/20.3 |
| 2003/0120347 A1 | 6/2003 | Steinberg | 623/22.17 |
| 2003/0158558 A1 | 8/2003 | Horn | 606/87 |
| 2003/0158606 A1 | 8/2003 | Coon et al. | 623/20.15 |
| 2003/0163137 A1 | 8/2003 | Smucker et al. | 606/87 |
| 2003/0173695 A1 | 9/2003 | Monkhouse et al. | 264/40.1 |
| 2003/0216669 A1 | 11/2003 | Lang et al. | 600/587 |
| 2003/0225457 A1 | 12/2003 | Justin et al. | 623/20.14 |
| 2003/0236521 A1 | 12/2003 | Brown et al. | 606/80 |
| 2004/0098133 A1 | 5/2004 | Carignan et al. | 623/20.35 |
| 2004/0102852 A1 | 5/2004 | Johnson et al. | 623/20.15 |
| 2004/0102866 A1 | 5/2004 | Harris et al. | 700/117 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0236424 A1 | 11/2004 | Berez et al. | 623/14.12 |
| 2004/0249386 A1 | 12/2004 | Faoro | 606/88 |
| 2005/0015153 A1 | 1/2005 | Goble et al. | 623/23.46 |
| 2005/0021039 A1 | 1/2005 | Cusick et al. | 606/88 |
| 2005/0043807 A1 | 2/2005 | Wood | 623/20.14 |
| 2005/0055028 A1 | 3/2005 | Haines | 606/79 |
| 2005/0085920 A1 | 4/2005 | Williamson | 623/20.14 |
| 2005/0107801 A1 | 5/2005 | Davies et al. | 606/96 |

(56) References Cited

U.S. PATENT DOCUMENTS

| | | | |
|---|---|---|---|
| 2005/0107883 A1 | 5/2005 | Goodfried et al. | 623/20.15 |
| 2005/0107884 A1 | 5/2005 | Johnson et al. | 623/20.15 |
| 2005/0107886 A1 | 5/2005 | Crabtree et al. | 623/20.24 |
| 2005/0119664 A1 | 6/2005 | Carignan et al. | 606/96 |
| 2005/0143745 A1 | 6/2005 | Hodorek et al. | 606/87 |
| 2005/0148843 A1 | 7/2005 | Roose | 600/407 |
| 2005/0171545 A1 | 8/2005 | Walsh et al. | 606/72 |
| 2005/0171612 A1 | 8/2005 | Rolston | 623/20.19 |
| 2005/0192588 A1 | 9/2005 | Garcia | 606/88 |
| 2005/0216305 A1 | 9/2005 | Funderud | 705/2 |
| 2005/0234461 A1 | 10/2005 | Burdulis, Jr. et al. | 606/79 |
| 2005/0267584 A1 | 12/2005 | Burdulis et al. | 623/20.19 |
| 2005/0278034 A1 | 12/2005 | Johnson et al. | 623/20.15 |
| 2006/0052795 A1 | 3/2006 | White | 606/102 |
| 2006/0069318 A1 | 3/2006 | Keaveny et al. | 600/300 |
| 2006/0111722 A1 | 5/2006 | Bouadi | 606/79 |
| 2006/0122616 A1 | 6/2006 | Bennett et al. | 606/87 |
| 2006/0149283 A1 | 7/2006 | May et al. | 606/96 |
| 2006/0200162 A1 | 9/2006 | Farling et al. | 606/88 |
| 2006/0235421 A1 | 10/2006 | Rosa et al. | 606/88 |
| 2007/0015995 A1 | 1/2007 | Lang | 600/407 |
| 2007/0073305 A1 | 3/2007 | Lionberger et al. | 606/87 |
| 2007/0118141 A1 | 5/2007 | Marchyn et al. | 606/88 |
| 2007/0198022 A1 | 8/2007 | Lang et al. | 606/88 |
| 2007/0203430 A1 | 8/2007 | Lang et al. | 600/587 |
| 2007/0208349 A1 | 9/2007 | Bastian et al. | 606/87 |
| 2007/0226986 A1* | 10/2007 | Park et al. | 29/592 |
| 2007/0233151 A1 | 10/2007 | Chudik | 606/96 |
| 2007/0233156 A1 | 10/2007 | Metzger | 606/130 |
| 2007/0255288 A1 | 11/2007 | Mahfouz et al. | 606/102 |
| 2007/0276224 A1 | 11/2007 | Lang et al. | 600/410 |
| 2007/0276501 A1 | 11/2007 | Betz et al. | 623/17.16 |
| 2007/0288030 A1 | 12/2007 | Metzger et al. | 606/87 |
| 2007/0293868 A1 | 12/2007 | Delfosse et al. | 606/88 |
| 2008/0004709 A1 | 1/2008 | O'Neill et al. | 623/20.35 |
| 2008/0015433 A1 | 1/2008 | Alexander et al. | 600/427 |
| 2008/0021566 A1 | 1/2008 | Peters et al. | 623/20.16 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0097450 A1 | 4/2008 | Brown et al. | 606/88 |
| 2008/0114370 A1 | 5/2008 | Schoenefeld | 606/96 |
| 2008/0147072 A1* | 6/2008 | Park et al. | 606/87 |
| 2008/0170659 A1 | 7/2008 | Lang et al. | 378/54 |
| 2008/0195216 A1 | 8/2008 | Philipp | 623/18.11 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0255445 A1 | 10/2008 | Neubauer et al. | 600/416 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Lang et al. | 606/87 |
| 2008/0281426 A1 | 11/2008 | Fitz et al. | 623/17.16 |
| 2008/0319448 A1 | 12/2008 | Lavallee et al. | 606/102 |
| 2009/0024131 A1 | 1/2009 | Metzger et al. | 606/88 |
| 2009/0076371 A1 | 3/2009 | Lang et al. | 600/407 |
| 2009/0087276 A1 | 4/2009 | Rose | 409/79 |
| 2009/0088753 A1 | 4/2009 | Aram et al. | 606/79 |
| 2009/0088758 A1 | 4/2009 | Bennett | 606/82 |
| 2009/0099567 A1 | 4/2009 | Zajac | 606/79 |
| 2009/0108912 A1 | 4/2009 | Erstad | 327/509 |
| 2009/0131941 A1 | 5/2009 | Park et al. | 606/87 |
| 2009/0131942 A1 | 5/2009 | Aker et al. | 606/88 |
| 2009/0222014 A1 | 9/2009 | Bojarski et al. | 606/88 |
| 2009/0226068 A1 | 9/2009 | Fitz et al. | 382/131 |
| 2009/0254093 A1 | 10/2009 | White et al. | 606/96 |
| 2009/0307893 A1 | 12/2009 | Burdulis, Jr. et al. | 29/527.1 |
| 2009/0326666 A1 | 12/2009 | Wyss et al. | 623/20.29 |
| 2010/0160917 A1 | 6/2010 | Fitz et al. | 606/88 |
| 2010/0168754 A1 | 7/2010 | Fitz et al. | 606/88 |
| 2010/0274534 A1 | 10/2010 | Steines et al. | 703/1 |
| 2010/0281678 A1 | 11/2010 | Burdulis, Jr. et al. | 29/592 |
| 2010/0298894 A1 | 11/2010 | Bojarski et al. | 606/86 R |
| 2010/0303313 A1 | 12/2010 | Lang et al. | 382/128 |
| 2010/0305573 A1 | 12/2010 | Fitz et al. | 606/87 |
| 2010/0305574 A1 | 12/2010 | Fitz et al. | 606/88 |
| 2011/0029093 A1 | 2/2011 | Bojarski et al. | 623/20.35 |
| 2011/0040387 A1 | 2/2011 | Ries et al. | 623/20.27 |
| 2011/0066193 A1 | 3/2011 | Lang et al. | 606/86 R |
| 2011/0071581 A1 | 3/2011 | Lang et al. | 606/86 R |
| 2011/0125009 A1 | 5/2011 | Lang et al. | 600/425 |
| 2011/0166578 A1 | 7/2011 | Stone et al. | 606/88 |
| 2011/0213368 A1 | 9/2011 | Fitz et al. | 606/80 |
| 2011/0213373 A1 | 9/2011 | Fitz et al. | 606/87 |
| 2011/0213374 A1 | 9/2011 | Fitz et al. | 606/87 |
| 2011/0213377 A1 | 9/2011 | Lang et al. | 606/89 |
| 2011/0213427 A1 | 9/2011 | Fitz et al. | 606/86 R |
| 2011/0213428 A1 | 9/2011 | Fitz et al. | 606/86 R |
| 2011/0213429 A1 | 9/2011 | Lang et al. | 606/86 R |
| 2011/0213430 A1 | 9/2011 | Lang et al. | 606/86 R |
| 2011/0213431 A1 | 9/2011 | Fitz et al. | 606/86 R |
| 2011/0218539 A1 | 9/2011 | Fitz et al. | 606/87 |
| 2011/0218542 A1 | 9/2011 | Lian | 606/88 |
| 2011/0218584 A1 | 9/2011 | Fitz et al. | 606/86 R |
| 2011/0230888 A1 | 9/2011 | Lang et al. | 606/87 |
| 2011/0238073 A1 | 9/2011 | Lang et al. | 606/89 |
| 2011/0295329 A1 | 12/2011 | Fitz et al. | 606/86 R |
| 2011/0313423 A1 | 12/2011 | Lang et al. | 606/87 |
| 2011/0319897 A1 | 12/2011 | Lang et al. | 606/79 |
| 2011/0319900 A1 | 12/2011 | Lang et al. | 606/87 |
| 2012/0018379 A1 | 1/2012 | Fitz et al. | 606/88 |
| 2012/0029520 A1 | 2/2012 | Lang et al. | 606/89 |
| 2012/0041446 A1 | 2/2012 | Wong et al. | 606/96 |
| 2012/0066892 A1 | 3/2012 | Lang et al. | 29/592 |
| 2012/0071881 A1 | 3/2012 | Lang et al. | 606/87 |
| 2012/0071882 A1 | 3/2012 | Lang et al. | 606/88 |
| 2012/0071883 A1 | 3/2012 | Lang et al. | 606/88 |
| 2012/0072185 A1 | 3/2012 | Lang et al. | 703/1 |
| 2012/0101503 A1 | 4/2012 | Lang et al. | 606/87 |
| 2012/0123422 A1 | 5/2012 | Agnihotri et al. | 606/89 |
| 2012/0143197 A1 | 6/2012 | Lang et al. | 606/87 |
| 2012/0151730 A1 | 6/2012 | Fitz et al. | 29/407.01 |
| 2012/0158001 A1 | 6/2012 | Burdulis, Jr. et al. | 606/88 |
| 2012/0209394 A1 | 8/2012 | Bojarski et al. | 623/20.32 |
| 2012/0289966 A1 | 11/2012 | Fitz et al. | 606/88 |
| 2012/0296337 A1 | 11/2012 | Fitz et al. | 606/80 |
| 2013/0018380 A1 | 1/2013 | Fitz et al. | 623/14.12 |
| 2013/0018464 A1 | 1/2013 | Fitz et al. | 606/88 |
| 2013/0023884 A1 | 1/2013 | Fitz et al. | 623/20.14 |
| 2013/0024000 A1 | 1/2013 | Bojarski et al. | 623/20.14 |
| 2013/0030419 A1 | 1/2013 | Fitz et al. | 606/1 |
| 2013/0030441 A1 | 1/2013 | Fitz et al. | 606/87 |
| 2013/0079781 A1 | 3/2013 | Fitz et al. | 606/80 |
| 2013/0079876 A1 | 3/2013 | Fitz et al. | 623/14.12 |
| 2013/0081247 A1 | 4/2013 | Fitz et al. | 29/407.09 |
| 2013/0096562 A1 | 4/2013 | Fitz et al. | 606/88 |
| 2013/0103363 A1 | 4/2013 | Lang et al. | 703/1 |
| 2013/0123792 A1 | 5/2013 | Fitz et al. | 606/96 |
| 2013/0184713 A1 | 7/2013 | Bojarski et al. | 606/88 |
| 2013/0211409 A1 | 8/2013 | Burdulis, Jr. et al. | 606/88 |
| 2013/0253522 A1 | 9/2013 | Bojarski et al. | 606/88 |
| 2013/0289570 A1 | 10/2013 | Chao | 606/88 |
| 2013/0296874 A1 | 11/2013 | Chao | 606/88 |
| 2013/0317511 A1 | 11/2013 | Bojarski et al. | 606/102 |
| 2013/0331850 A1 | 12/2013 | Bojarski et al. | 606/102 |
| 2014/0031826 A1 | 1/2014 | Bojarski et al. | 606/87 |
| 2014/0058396 A1 | 2/2014 | Fitz et al. | 606/87 |
| 2014/0058397 A1 | 2/2014 | Fitz et al. | 606/88 |
| 2014/0066935 A1 | 3/2014 | Fitz et al. | 606/87 |
| 2014/0066936 A1 | 3/2014 | Fitz et al. | 606/87 |
| 2014/0074441 A1 | 3/2014 | Fitz et al. | 703/1 |
| 2014/0163568 A1 | 6/2014 | Wong et al. | 606/96 |
| 2014/0188240 A1 | 7/2014 | Lang et al. | 623/22.12 |
| 2014/0208578 A1 | 7/2014 | Linderman et al. | 29/592 |
| 2014/0250676 A1 | 9/2014 | Lang et al. | 29/592 |

FOREIGN PATENT DOCUMENTS

| | | | |
|---|---|---|---|
| DE | 44 34 539 | 4/1996 | A61F 2/38 |
| DE | 20303498 | 8/2003 | A61B 17/15 |
| EP | 0337901 | 10/1989 | A61B 17/14 |
| EP | 0528080 | 2/1993 | A61F 2/30 |

(56) References Cited

FOREIGN PATENT DOCUMENTS

| | | | |
|---|---|---|---|
| EP | 0 704 193 | 4/1996 | ............... A61F 2/30 |
| EP | 0626156 | 7/1997 | ............... A61F 2/38 |
| EP | 0908836 | 4/1999 | ............... G06F 19/00 |
| EP | 0613380 | 12/1999 | ............... A61F 27/00 |
| EP | 0993807 | 4/2000 | ............... A61B 17/17 |
| EP | 1074229 | 2/2001 | ............... A61F 2/38 |
| EP | 1077253 | 2/2001 | ............... C12N 5/00 |
| EP | 1120087 | 8/2001 | ............... A61B 17/06 |
| EP | 1129675 | 9/2001 | ............... A61F 2/30 |
| EP | 1132061 | 9/2001 | ............... A61F 2/28 |
| EP | 0732091 | 12/2001 | ............... A61F 2/38 |
| EP | 0896825 | 7/2002 | ............... A61L 27/00 |
| EP | 0814731 | 8/2002 | ............... A61F 2/30 |
| EP | 1234552 | 8/2002 | ............... A61F 2/00 |
| EP | 1234555 | 8/2002 | ............... A61F 2/30 |
| EP | 0809987 | 10/2002 | ............... A61F 2/38 |
| EP | 0833620 | 10/2002 | ............... A61K 9/22 |
| EP | 0530804 | 6/2004 | ............... A61L 25/00 |
| FR | 2819714 | 7/2002 | ............... A61F 2/44 |
| FR | 2918554 | 1/2009 | ............... A61B 17/17 |
| GB | 1451283 | 9/1976 | ............... A61F 1/24 |
| GB | 2291355 | 1/1996 | ............... A61F 2/38 |
| GB | 2348373 | 10/2000 | ............... A61F 2/38 |
| JP | 1-249049 | 10/1989 | ............... A61F 2/38 |
| JP | 8-173465 | 7/1996 | ............... A61F 2/38 |
| JP | 9-206322 | 8/1997 | ............... A61F 2/38 |
| JP | 2002-102236 | 4/2002 | ............... A61B 17/16 |
| WO | WO 87/02882 | 5/1987 | ............... A61F 2/38 |
| WO | WO 90/09769 | 9/1990 | ............... A61F 2/28 |
| WO | WO 93/04710 | 3/1993 | ............... A61L 25/00 |
| WO | WO 93/09819 | 5/1993 | ............... A61L 27/00 |
| WO | WO 93/25157 | 12/1993 | ............... A61B 17/57 |
| WO | WO 95/27450 | 10/1995 | ............... A61F 2/38 |
| WO | WO 95/28688 | 10/1995 | ............... G06T 15/00 |
| WO | WO 95/30390 | 11/1995 | ............... A61F 2/38 |
| WO | WO 95/32623 | 12/1995 | ............... A01N 1/02 |
| WO | WO 96/24302 | 8/1996 | ............... A61B 17/90 |
| WO | WO 97/25942 | 7/1997 | ............... A61F 2/32 |
| WO | WO 97/26847 | 7/1997 | ............... A61F 2/44 |
| WO | WO 97/27885 | 8/1997 | ............... A61L 27/00 |
| WO | WO 97/38676 | 10/1997 | ............... A61K 9/10 |
| WO | WO 98/12994 | 4/1998 | ............... A61F 2/28 |
| WO | WO 98/20816 | 5/1998 | ............... A61F 2/38 |
| WO | WO 98/30617 | 7/1998 | ............... C08G 63/12 |
| WO | WO 98/32384 | 7/1998 | ............... A61B 17/58 |
| WO | WO 99/02654 | 1/1999 | ............... C12N 5/00 |
| WO | WO 99/08598 | 2/1999 | ............... A61B 8/00 |
| WO | WO 99/08728 | 2/1999 | ............... A61L 27/00 |
| WO | WO 99/40864 | 8/1999 | ............... A61B 17/56 |
| WO | WO 99/42061 | 8/1999 | ............... A61F 2/38 |
| WO | WO 99/47186 | 9/1999 | ............... A61L 27/00 |
| WO | WO 99/51719 | 10/1999 | ............... C12M 3/00 |
| WO | WO 99/56674 | 11/1999 | ............... A61F 2/36 |
| WO | WO 00/09179 | 2/2000 | ............... A61L 25/00 |
| WO | WO 00/15153 | 3/2000 | ............... A61F 2/38 |
| WO | WO 00/19911 | 4/2000 | ............... A61B 17/02 |
| WO | WO 00/35346 | 6/2000 | ............... A61B 5/11 |
| WO | WO 00/48550 | 8/2000 | |
| WO | WO 00/59411 | 10/2000 | ............... A61F 2/38 |
| WO | WO 00/74554 | 12/2000 | |
| WO | WO 01/10356 | 2/2001 | ............... A61F 2/46 |
| WO | WO 01/17463 | 3/2001 | ............... A61F 2/30 |
| WO | WO 01/19254 | 3/2001 | ............... A61B 17/00 |
| WO | WO 01/35968 | 5/2001 | ............... A61K 35/00 |
| WO | WO 01/45764 | 6/2001 | ............... A61L 27/36 |
| WO | WO 01/66021 | 9/2001 | ............... A61B 17/14 |
| WO | WO 01/68800 | 9/2001 | ............... C12M 3/00 |
| WO | WO 01/70142 | 9/2001 | ............... A61F 2/38 |
| WO | WO 01/91672 | 12/2001 | ............... A61F 2/36 |
| WO | WO 02/00270 | 1/2002 | ............... A61L 27/14 |
| WO | WO 02/00275 | 1/2002 | ............... A61L 31/14 |
| WO | WO 02/02158 | 1/2002 | ............... A61L 27/14 |
| WO | WO 02/22013 | 3/2002 | ............... A61B 5/055 |
| WO | WO 02/22014 | 3/2002 | ............... A61B 5/055 |
| WO | WO 02/23483 | 3/2002 | ............... G06T 11/00 |
| WO | WO 02/34310 | 5/2002 | ............... A61L 31/04 |
| WO | WO 02/36147 | 5/2002 | ............... A61K 31/04 |
| WO | WO 02/061688 | 8/2002 | ............... G06T 17/00 |
| WO | WO 02/096268 | 12/2002 | |
| WO | WO 03/007788 | 1/2003 | |
| WO | WO 03/037192 | 5/2003 | ............... A61B 17/15 |
| WO | WO 03/047470 | 6/2003 | ............... A61F 2/34 |
| WO | WO 03/051210 | 6/2003 | ............... A61B 17/58 |
| WO | WO 03/055400 | 7/2003 | ............... A61B 17/74 |
| WO | WO 2004/043305 | 5/2004 | ............... A61F 2/30 |
| WO | WO 2004/049981 | 6/2004 | ............... A61F 2/46 |
| WO | WO 2005/051239 | 6/2005 | ............... A61F 2/08 |
| WO | WO 2005/051240 | 6/2005 | ............... A61F 2/08 |
| WO | WO 2006/060795 | 6/2006 | ............... A61B 17/17 |
| WO | WO 2006/127283 | 11/2006 | ............... A61B 17/17 |
| WO | WO 2007/041375 | 4/2007 | ............... A61F 2/38 |
| WO | WO 2007/092841 | 8/2007 | ............... A61B 17/15 |
| WO | WO 2008/112996 | 9/2008 | ............... A61B 17/15 |
| WO | WO 2008/117028 | 10/2008 | ............... A61B 17/15 |
| WO | WO 2008/157412 | 12/2008 | ............... A61B 17/17 |
| WO | WO 2009/009660 | 1/2009 | ............... A61F 2/30 |
| WO | WO 2009/111639 | 9/2009 | ............... A61B 17/58 |
| WO | WO 2010/121147 | 10/2010 | ............... A61B 17/90 |
| WO | WO 2012/112694 | 8/2012 | ............... A61B 6/00 |
| WO | WO 2012/112698 | 8/2012 | ............... A61F 2/30 |
| WO | WO 2012/112701 | 8/2012 | ............... A61F 2/30 |
| WO | WO 2012/112702 | 8/2012 | ............... A61F 2/30 |
| WO | WO 2013/119865 | 8/2013 | ............... A61B 17/90 |

OTHER PUBLICATIONS

Argenson et al., "Is There a Place for Patellofemoral Arthroplasty?," Clinical Orthopaedics and Related Research No. 321, pp. 162-167 (1995).

Birnbaum et al., "Computer-Assisted Orthopedic Surgery With Individual Templates and Comparison to Conventional Operation Method", Spine, vol. 26, No. 4, pp. 365-369, Feb. 2001.

Blum et al., "Knee Arthroplasty in Patients with Rheumatoid Arthritis," Ann. Rheum. Dis. 33 (1): 1-11 (1974).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

CAOS, "MIS meets CAOS Spring 2005 Symposium Schedule", *CAOS Spring 2005 Symposium*, pp. 1-9, May 19, 2005.

Carr et al., "Surface Interpolation with Radial Basis Functions for Medical Imaging," IEEE Transactions on Medical Imaging, IEEE, Inc. New York, vol. 16, pp. 96-107 (Feb. 1997).

Chelule et al., "Patient-Specific Template to Preserve Bone Stock in Total Knee Replacement: Preliminary Results", *15th Annual ISTA Symposium*, Sep. 2002, 1 page.

Chelule et al., "Computer Aided Design of Personalized Jigs in Total Knee Replacement", 3rd Annual Meeting of CAOS Int'l Proc., Spain, Jun. 18, 21, 2003, pp. 58-59.

Clary et al., "Experience with the MacIntosh Knee Prosthesis," South Med. J. 65(3):265-272 (1972).

Conaty, et al., "Surgery of the Hip and Knee in Patients with Rheumatoid Arthritis," J. Bone Joint Surg. Am. 55(2):301-314 (1973).

DeWinter et al., "The Richards Type II Patellofemoral Arthroplasty", Acta Orthop Scand 2001; 72 (5): 487-490.

(56) References Cited

OTHER PUBLICATIONS

Delp et al., "A Graphics-Based Software System to Develop and Analyze Models of Musculoskeletal Structures," Comput. Biol. Med., vol. 25, No. 1, pp. 21-34, 1995.
Farrar et al., "Computed Tomography Scan Scout Film for Measurement of Femoral Axis in Knee Arthroplasty," J. Arthroplasty, vol. 14, No. 8, pp. 1030-1031, 1999.
Froemel et al., "Computer Assisted Template Based Navigation for Total Knee Replacement", Documents presented at CAOS on Jun. 17, 2001, 4 pages.
Ghelman et al., "Kinematics of the Knee After Prosthetic Replacements", Clin. Orthop. May 1975: (108): 149-157.
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hafez et al., "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatol., vol. 1, pp. 121-131, 2006.
Hastings et al., "Double Hemiarthroplasty of the Knee in Rheumatoid Arthritis," A Survey of Fifty Consecutive Cases, J. Bone Joint Surg. Br. 55(1):112-118 (1973).
Henderson et al., "Experience with the Use of the Macintosh Prosthesis in Knees of Patients with Pheumatoid Arthritis," South. Med. J. 62(11):1311-1315 (1969).
Jessop et al., "Follow-up of the MacIntosh Arthroplasty of the Knee Joint," Rheumatol Phys. Med. 11(5):217-224 (1972).
Kates, et al., "Experiences of Arthroplasty of the Rheumatoid Knee Using MacIntosh Prostheses," Ann. Rheum. Dis. 28(3):328 (1969).
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Kim et al., "Measurement of Femoral Neck Anteversion in 3D. Part 1: 3D Imaging Method," Med and Viol. Eng. and Computing, vol. 38, No. 6, pp. 603-609, 2000.
Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.
Lam et al., "X-Ray Diagnosis: A Physician's Approach", Editor Lam, 1998, Springer-Verlag publishers, Title page and Table of Contents pgs. Only (ISBN 9813083247).
Lam et al., "Varus/Valgus Alignment of the Femoral Component in Total Knee Arthroplasty," The Knee, vol. 10, pp. 237-241, 2003.
Leenslag et al., "A Porous Composite for Reconstruction of Meniscus Lesions," Biological and Biomechanical Perform. of Biomaterials, Elsevier Science Publishers Amsterdam pp. 147-152 (1986).
Lu et al., "In vitro degradation of porous poly(L-lactic acid) foams", Biomaterials, 21(15):1595-1605, Aug. 2000.
MacIntosh, "Arthroplasty of the Knee in Rheumatoid Arthritis," Proceedings and Reports of Councils and Assotions, J. Bone & Joint Surg., vol. 48B No. (1): 179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Mahaisavariya et al., "Morphological Study of the Proximal Femur: A New Method of Geometrical Assessment Using 3 Dimensional Reverse Engineering," Med. Eng. and Phys., vol. 24, pp. 617-622, 2002.
Marler et al., "Soft-Tissue Augmentation with Injectable Alginate and Syngeneic Fibroblasts", Plastic & Reconstructive Surgery, 105(6):2049-2058, May 2000.
Matsen, III et al., "Robotic Assistance in Orthopaedic Surgery: A Proof of Principle Using Distal Femoral Arthroplasty", Clinical Ortho. and Related Research, 296:178-186 (1993).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Nelson et al., "Arthroplasty and Arthrodesis of the Knee Joint," Orthop. Clin. North Am. 2 (1): 245-64 (1971).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine et al., English Translation with Certification: "Model-Based Operation Planning in Orthopedic Surgery", Thesis, RWTH Aachen University, Apr. 22, 2004, 170 pages.
Portheine et al., In German: "Computer-Assisted Total Knee Endoprosthetics with Planning-Specific Treatement Templates", Biomed. Tech., vol. 46, Supp. vol. 1, Jan. 2001.
Portheine et al., English Translation with Certification: "Computer-Assisted Total Knee Endoprosthetics with Planning-Specific Treatement Templates", Biomed. Tech., vol. 46, Supp. vol. 1, Jan. 2001.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Radermacher, English Translation : Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." in Troccaz J. Grimson E., Mosges R (eds). Computer Vision, Virtual Reality and Robotics in

(56) References Cited

OTHER PUBLICATIONS

Medicine and Medical Robotics and Computer Assisted Surgery, Lecture Notes in Computer Science. Berlin, Springer-Verlag 606-616, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and aspects of Clinical Applications." In Nolte LP, Ganz, R. (eds). CAOS—Computer Assisted Orthopaedic Surgery. Bern, Hans Huber (In Press) 1998.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—are there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Radermacher, "Template Based Navigation—An Efficient Technique for Hip and Knee Surgery", CAOS First Asian Meet, India, Mar. 27-28, 2004, pp. 44-50.
Ranawat et al., "MacIntosh Hemiarthroplasty in Rheumatoid Knee," Acta Orthop Belg., 39 (1): 1-11 (1973).
Rau et al., "Small and Neat", Medical Tech. Int'l, pp. 65, 67 and 69, 1993-94.

Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schkommadau et al., "Clinical Application of Individual Templates for Pedicle Screw Placement in Comparison to Computer Navigation", Poster presented at CAOS, Feb. 18, 2000, 1 page.
Schkommadau et al., In German: "Clinical Experience With the Individual Template Technique", Orth. Prac., vol. 37, No. 1, pp. 19-22, 2001.
Schkommadau et al., English Translation with Certification: "Clinical Experience With the Individual Template Technique", Orth. Prac., vol. 37, No. 1, pp. 19-22, 2001.
Schorn et al., "MacIntosh Arthroplasty in Rheumatoid Arthritis," Rheumatol Rehabil. Aug. 1978:17(3):155-163.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Slone et al., "Body CT: A Practical Approach", Editor Slone, 1999 McGraw-Hill publishers, Title page and Table of Contents pgs. Only (ISBN 007058219).
Staudte et al., In German: "Computer-Assisted Operation Planning and Technique in Orthopedics", North Rhine-Westphalia Acad. for Sciences, Lecture N.444, ISSN 0944-8799, 2000, 17 pages.
Staudte et al., English Translation with Certification: "Computer-Assisted Operation Planning and Technique in Orthopedics", North Rhine-Westphalia Acad. for Sciences, Lecture N.444, ISSN 0944-8799, 2000, 34 pages.
Stauffer et al. "The MacIntosh Prosthesis. Prospective Clinical and Gait Evaluation," Arch. Surg. 110(6):717-720 (1975).
Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Testi et al., "Border Tracing Algorithm Implementation for the Femoral Geometry Reconstruction," Comp. Meth. and Programs in Biomed., vol. 65, pp. 175-182, 2001.
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
Vandeberg et al., "Assessment of Knee Cartilage in Cadavers With Dual-Detector Spiral CT Arthrography and MR Imaging", Radiology, Feb. 2002: 222(2): 430-435.
Wiese et al., "Biomaterial properties and biocompatibility in cell culture of a novel self-inflating hydrogel tissue expander", J. Biomedical Materials Research Part A, 54(2):179-188, Nov. 2000.
Wordsworth et al., "MacIntosh Arthroplasty for the Rheumatoid Knee: A 10-year Follow Up," Ann. Rheum. Dis. 44(11):738-741 (1985).

(56) References Cited

OTHER PUBLICATIONS

Yusof et al., "Preparation and characterization of chitin beads as a wound dressing precursor", J. Biomedical Materials Research Part A, 54(1):59-68, Oct. 2000.
International Searching Authority, International Search Report—International Application No. PCT/US03/38158, dated Feb. 23, 2005, 6 pages.
European Patent Office, European Search Report—Application No. EP 03790194, dated Jul. 13, 2006, 5 pages.
International Searching Authority, International Search Report—International Application No. PCT/US04/39616, dated Mar. 28, 2005, together with the Written Opinion of the International Searching Authority, 6 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2006/045172, dated Apr. 19, 2007, 5 pages.
International Searching Authority, International Search Report—International Application No. PCT/US2007/061681, dated Sep. 7, 2007, together with the Written Opinion of the International Searching Authority, 12 pages.
European Patent Office, Supplementary European Search Report—Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
International Searching Authority, International Search Report—International Application No. PCT/US2008/057045, dated Jul. 15, 2008, together with the Written Opinion of the International Searching Authority, 9 pages.
International Searching Authority, Invitation to Pay Additional Fees, and Where Applicable, Protest Fee—International Application No. PCT/US2008/066994, dated Oct. 21, 2008, 5 pages.
International Searching Authority, International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark Office, Office Action dated Jan. 6, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 16 pages.
International Searching Authority, International Search Report—International Application No. PCT/US2009/036189, dated Jul. 13, 2009, together with the Written Opinion of the International Searching Authority, 11 pages.
Sunstein Kann Murphy & Timbers LLP, Supplemental Amendment dated Sep. 18, 2009, pertaining to U.S. Appl. No. 09/882,363, 11 pages.
United States Patent and Trademark Office Office, Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office action dated Jan. 26, 2010, pertaining to U.S. Appl. No. 11/671,745, 48 pages.
International Searching Authority, International Search Report—International Application No. PCT/US10/31415, dated Jun. 29, 2010, together with the Written Opinion of the International Searching Authority, 9 pages.
United States Patent and Trademark Office, Office Action dated Oct. 20, 2010, pertaining to U.S. Appl. No. 12/135,719, 10 pages.
Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 10181743.5-2310, dated Mar. 11, 2011, 6 pages.
European Patent Office, Extended European Search Report—Application No. 10765271.1-2310, dated Dec. 19, 2012, 6 pages.
European Patent Office, European Search Report—Application No. 09716738.1 dated Feb. 6, 2012, 10 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
United States Patent and Trademark Office, Office Action dated Apr. 20, 2011, pertaining to U.S. Appl. No. 12/135,612, 13 pages.
United States Patent and Trademark Office, Office Action dated Sep. 26, 2011 pertaining to U.S. Appl. No. 12/048,764, 9 pages.
United States Patent and Trademark Office, Office Action dated Oct. 23, 2009, pertaining to U.S. Appl. No. 10/764,010, 13 pages.
United States Patent and Trademark Office, Office Action dated Jan. 9, 2009, pertaining to U.S. Appl. No. 10/764,010 11 pages.
Bromberg & Sunstein LLP, Response to Office Action dated Jan. 9, 2009, pertaining to U.S. Appl. No. 10/764,010, 25 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
United States Patent and Trademark Office, Notice of Allowance dated Aug. 5, 2011, pertaining to U.S. Appl. No. 10/764,010, 14 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.

(56) References Cited

OTHER PUBLICATIONS

Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
United States Patent and Trademark Office, Office Action dated Jan. 13, 2012 pertaining to U.S. Appl. No. 12/776,840, 10 pages.
United States Patent and Trademark Office, Office Action dated Jan. 26, 2012, pertaining to U.S. Appl. No. 12/139,324, 14 pages.
United States Patent and Trademark Office, Office Action dated May 31, 2012, pertaining to U.S. Appl. No. 12/398,753, 7 pages.
United States Patent and Trademark Office, Office Action dated Jun. 5, 2012, pertaining to U.S. Appl. No. 12/776,984, 7 pages.
European Patent Office European Search Report—Application No. 12170854.9-1526, dated Oct. 9, 2012, 6 pages.
Cohen et al., "Computer-Aided Planning of Patellofemoral Joint OA Surgery: Developing Physical Models from Patient MRI", MICCAI, Oct. 11-13, 1998, 13 pages.
Cohen et al., "Knee Cartilage Topography Thickness and Contact Areas From MRI: In-Vitro Calibration and In-Vivo Measurements", Osteoarthritis and Cartilage vol. 7, No. 1, pp. 95-109 (1999).
Macdonald et al., "Inaccuracy of Acetabular Reaming Under Surgical Conditions", Journ. of Arthro., vol. 14, No. 6, pp. 730-737, 1999.
Müller-Wittig et al., "A Computer-Assisted Planning System for Total Knee Replacement", CG Topics, pp. 17-19, Jun. 2000.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/025274 dated Oct. 25, 2012, together with the Written Opinion of the International Searching Authority, 12 pages.
International Searching Authority, International Search Report—International Application No. PCT/US2012/025277 dated Oct. 25, 2012, together with the Written Opinion of the International Searching Authority, 12 pages.
International Searching Authority, International Search Report—International Application No. PCT/US2012/025280 dated Oct. 25, 2012, together with the Written Opinion of the International Searching Authority, 11 pages.
International Searching Authority, International Search Report—International Application No. PCT/US2013/025216 dated May 30, 2013, 5 pages.
European Patent Office, Extended European Search Report—Application No. 13164557.4-1659 dated Nov. 25, 2013, 8 pages.
European Patent Office, Extended European Search Report—Application No. 13167237.0-1659 dated Nov. 25, 2013, 8 pages.
European Patent Office, Extended European Search Report—Application No. 13167246.1-1659 dated Nov. 25, 2013, 8 pages.
European Patent Office, Extended European Search Report—Application No. 13167257.8-1659 dated Nov. 25, 2013, 8 pages.
United States Patent and Trademark Office, Office Action pertaining to U.S. Appl. No. 13/405,843 dated Dec. 10, 2013, 9 pages.
United States Patent and Trademark Office, Office Action dated Feb. 13, 2014, pertaining to U.S. Appl. No. 13/306,501, 25 pages.
United States Patent and Trademark Office, Office Action dated Jul. 28, 2014, pertaining to U.S. Appl. No. 13/305,634, 12 pages.
European Patent Office, Extended European Search Report—Application No. 13164551.7-1659 dated Jul. 31, 2014, 7 pages.
Buechel, "Meniscal-Bearing Total Knee Arthroplasty", Chapter 10 of Surgical Techniques in Total Knee Arthroplasty, pp. 81-89, 2002.
Delp et al., "Computer Assisted Knee Replacement", Clinical Orthopaedics, pp. 49- 56, Sep. 1998.
Intergraph Corp. and Surgicad Corp., "Surgicad Design Combines 3-D Visualization with CAD Tools", Intergraph Corp. and Surgicad Corp. News Brief, 2 pages, Sep. 1993.
Keblish, Jr., MD, "Surgical Techniques in the Performance of Unicompartmental Arthroplasties", Operative Techniques in Orthopaedics, vol. 8, No. 3, pp. 134-145, Jul. 1998.
Rhodes et al., "An Application of Computer Graphics and Networks to Anatomic Model and Prosthesis Manufacturing", IEEE CG&A, pp. 12-25, Feb. 1987.
Wright Medical Technology, "Advantim Total Knee System—Total Condylar & Posterior Stabilized Surgical Technique" by Wright Medical Technology, 66 pages, 1995.
Wright Medical Technology, "Axiom Modular Knee System, Surgical Technique" by Wright Medical Technology, 16 pages, 1996.
Udupa et al., "3D Imaging in Medicine", Second Edition, pp. 84-86, 2000.
Proskauer Rose LLP et al., Counsel for ConforMIS, Inc., United States District Court of Massachusetts, Civil Action No. 13-12312—Document No. 1—Plaintiff's Complaint for Patent Infringement—ConforMIS, Inc., 406 pages, 2013.
Duane Morris LLP et al., Counsel for Wright Medical Technology, Inc. et al., United States District Court of Massachusetts, Civil Action No. 13-12312—Document No. 18—Defendant's Answer, Affirmative Defenses and Counterclaims to Plaintiff's Complaint—Wright Medical Technology, Inc. et al., 17 pages, 2013.
Proskauer Rose LLP et al., Counsel for ConforMIS, Inc., United States District Court of Massachusetts, Civil Action No. 13-12312—Document No. 31—Plaintiff's First Amended Complaint for Patent Infringement—ConforMIS, Inc., 543 pages, 2014.
Keker & Van Nest LLP et al., Counsel for ConforMIS, Inc., United States District Court of Massachusetts, Civil Action No. 13-12312—Document No. 34—Plaintiff and Counterclaim Defendant's Answer to Counterclaims—ConforMIS, Inc., 5 pages, 2014.
Duane Morris LLP et al., Counsel for Wright Medical Technology, Inc. et al., United States District Court of Massachusetts, Civil Action No. 13-12312—Document No. 35—Defendant's Answer, Affirmative Defenses and Counterclaims to Plaintiff's First Amended Complaint for Patent Infringement—Wright Medical Technology, Inc. et al., 24 pages, 2014.
Proskauer Rose LLP et al., Counsel for ConforMIS, Inc., United States District Court of Massachusetts, Civil Action No. 13-12312—Document No. 44—Plaintiff and Counterclaim Defendant's Answer to Amended Counterclaims—ConforMIS, Inc. 6 pages, 2014.
Posternak Blankstein & Lund LLP, Counsel for MicroPort Orthopedics Inc., United States District Court of Massachusetts, Civil Action No. 13-12312—Document No. 52—Defendant MicroPort Orthopedics, Inc.'s Answer, Affirmative Defenses, and Counterclaims to Plaintiff's First Amended Complaint for Patent Infringement—MicroPort Orthopedics, Inc., 22 pages, 2014.
Proskauer Rose LLP et al., Counsel for ConforMIS, Inc., United States District Court of Massachusetts, Civil Action No. 13-12312—Document No. 53—Plaintiff and Counterclaim Defendant's Answer to MicroPort Orthopedics Inc.'s Counterclaims—ConforMIS, Inc., 5 pages, 2014.
Duane Morris LLP et al., Counsel for Wright Medical Technology, Inc. et al., United States District Court of Massachusetts, Civil Action No. 13-1231—Document No. 55—Defendants' Preliminary Invalidity and Non-Infringement Disclosures—Wright Medical Technology, Inc. et al. 22 pages, 2014.

\* cited by examiner

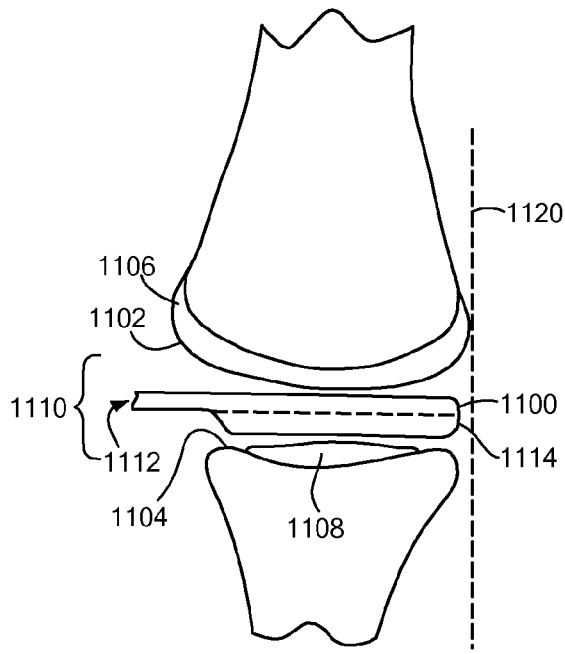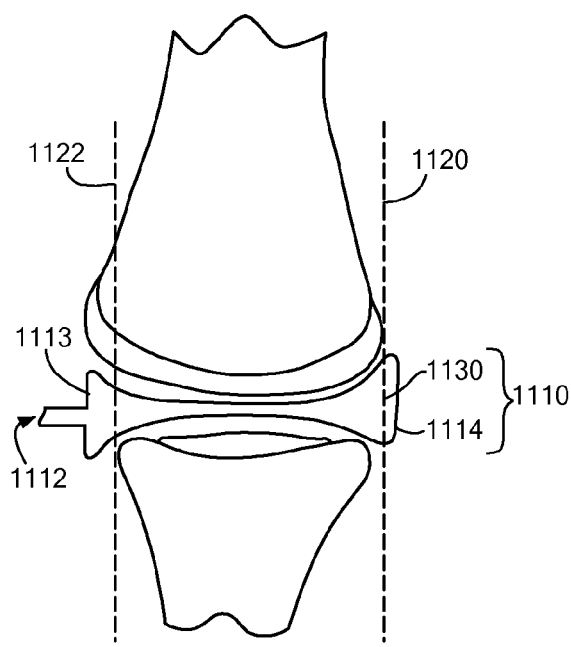
*FIG. 11A*                    *FIG. 11B*
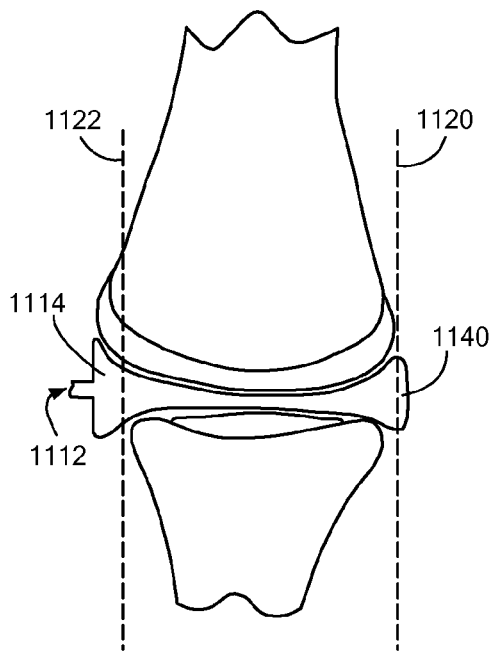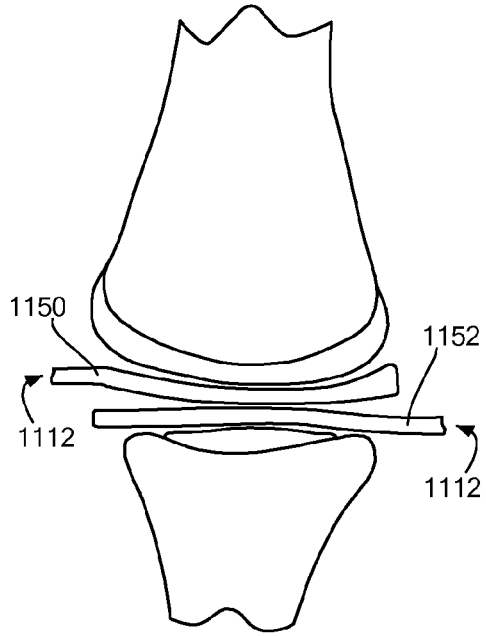
*FIG. 11C*                    *FIG. 11D*

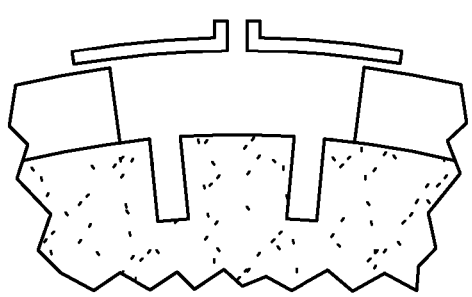
*FIG. 14G(1)*
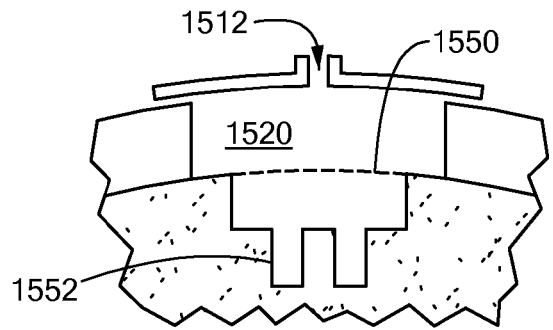
*FIG. 14G(2)*
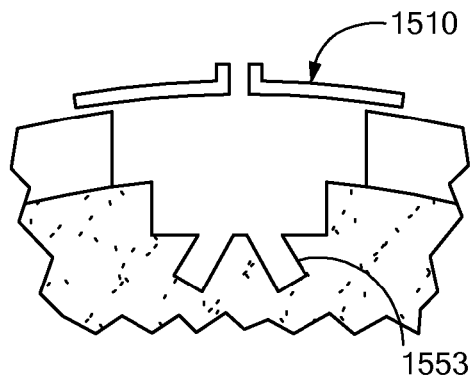
*FIG. 14G(3)*
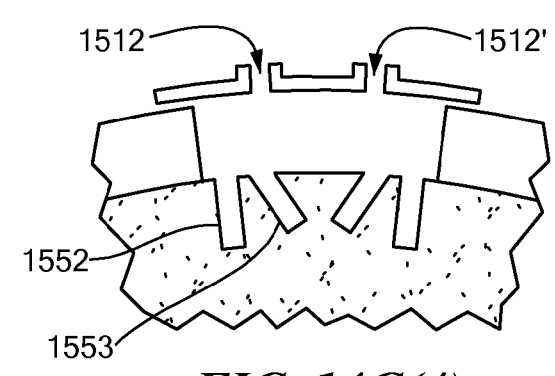
*FIG. 14G(4)*
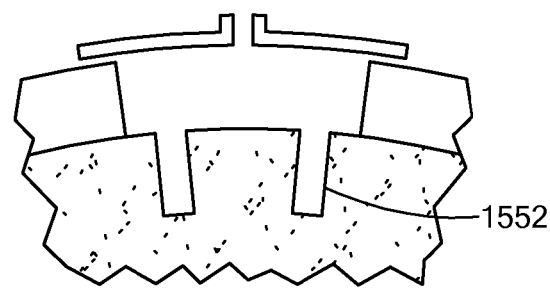
*FIG. 14G(5)*
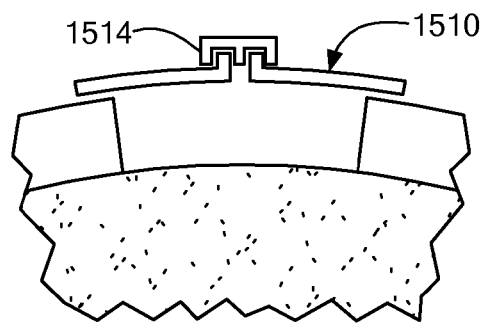
*FIG. 14G(6)*
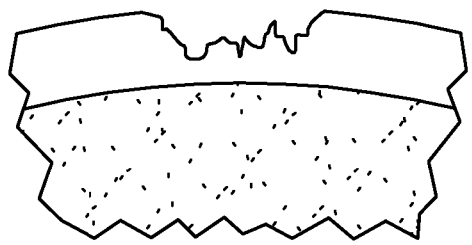
*FIG. 14G(7)*

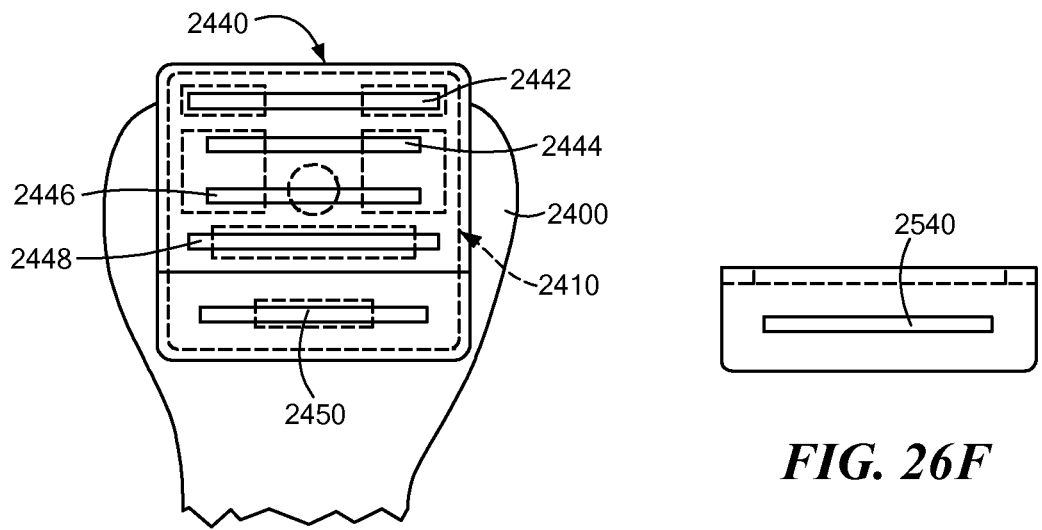
*FIG. 26E*
*FIG. 26F*
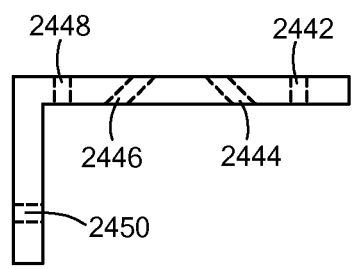
*FIG. 26G*
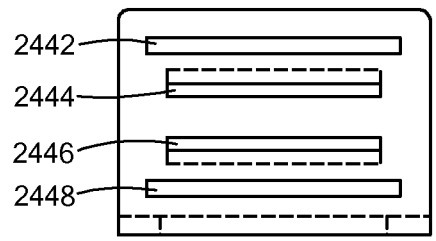
*FIG. 26H*
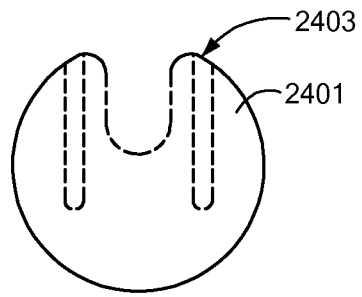
*FIG. 26I*

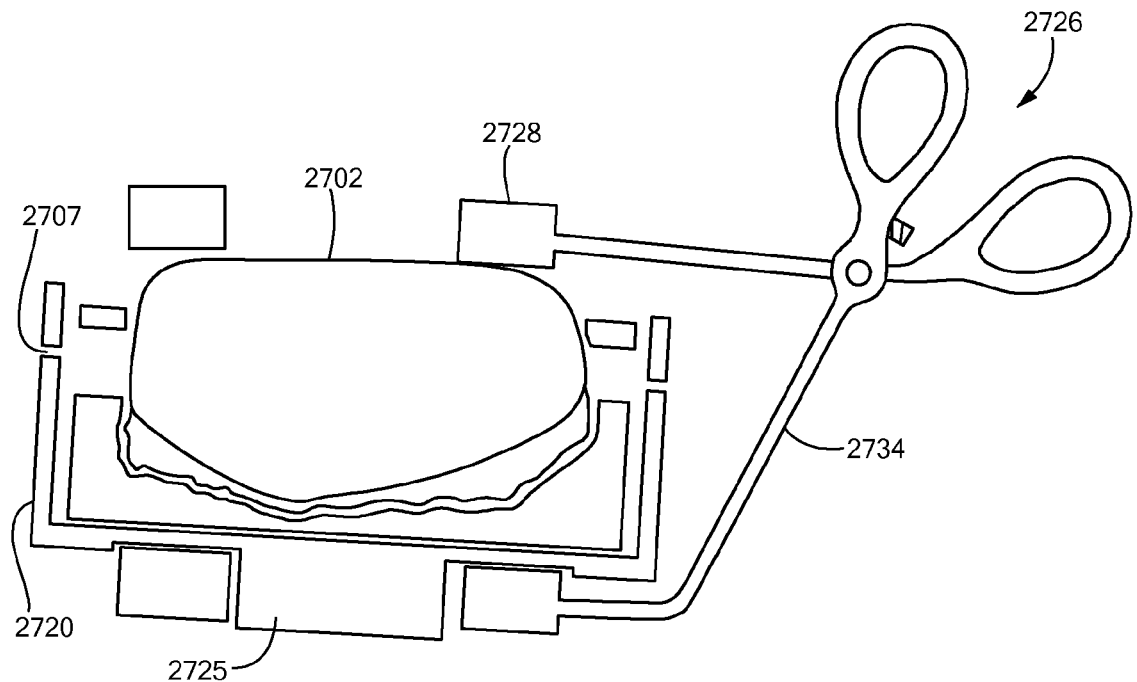
FIG. 27E
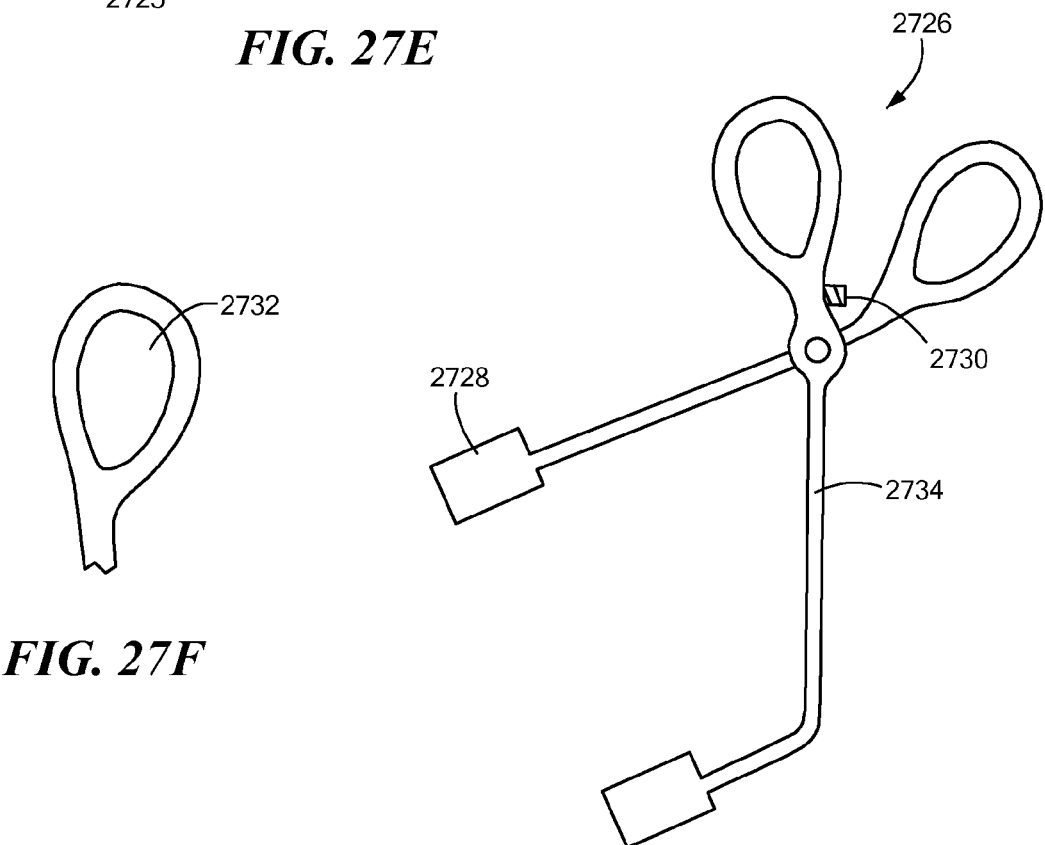
FIG. 27F
FIG. 27G

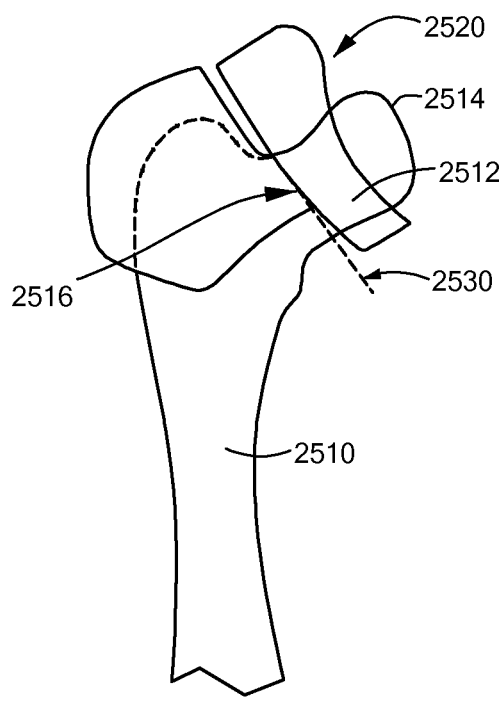
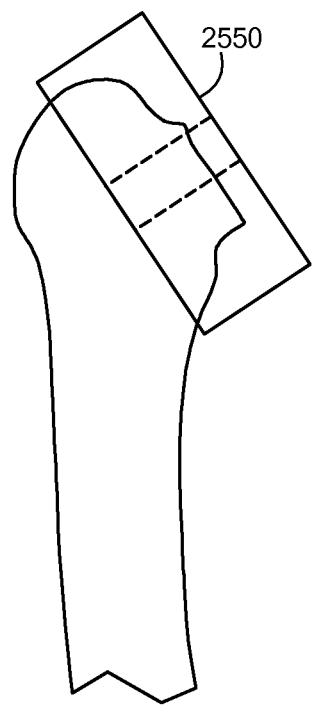
FIG. 28A   FIG. 28C
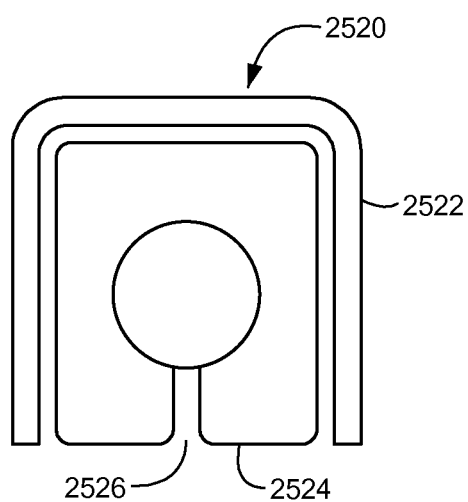
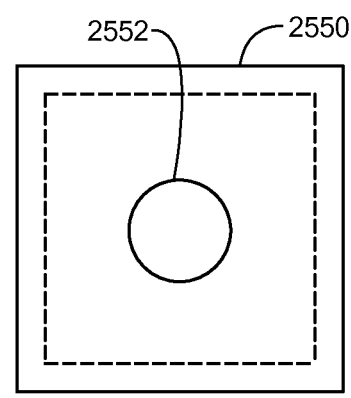
FIG. 28B   FIG. 28D

JOINT ARTHROPLASTY DEVICES AND SURGICAL TOOLS

CROSS-REFERENCE TO RELATED APPLICATIONS

This application is a continuation of U.S. Ser. No. 12/606,830, entitled "Joint Arthroplasty Devices and Surgical Tools," filed Oct. 27, 2009, which is a continuation of U.S. Ser. No. 10/724,010, entitled "Patient Selectable Joint Arthroplasty Devices and Surgical Tools Facilitating Increased Accuracy, Speed and Simplicity in Performing Total and Partial Joint Arthroplasty," filed Nov. 25, 2003, which is a continuation-in-part of U.S. Ser. No. 10/305,652 entitled "METHODS AND COMPOSITIONS FOR ARTICULAR REPAIR," filed Nov. 27, 2002, which is a continuation-in-part of U.S. Ser. No. 10/160,667, filed May 28, 2002, which in turn claims the benefit of U.S. Ser. No. 60/293,488 entitled "METHODS TO IMPROVE CARTILAGE REPAIR SYSTEMS", filed May 25, 2001, U.S. Ser. No. 60/363,527, entitled "NOVEL DEVICES FOR CARTILAGE REPAIR, filed Mar. 12, 2002 and U.S. Ser. Nos. 60/380,695 and 60/380,692, entitled "METHODS AND COMPOSITIONS FOR CARTILAGE REPAIR," and "METHODS FOR JOINT REPAIR,", filed May 14, 2002, all of which applications are each hereby incorporated by reference in their entirety.

FIELD OF THE INVENTION

The present invention relates to orthopedic methods, systems and prosthetic devices and more particularly relates to methods, systems and devices for articular resurfacing. The present invention also includes surgical molds designed to achieve optimal cut planes in a joint in preparation for installation of a joint implant.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on joint and site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. One approach includes the use of matrices, tissue scaffolds or other carriers implanted with cells (e.g., chondrocytes, chondrocyte progenitors, stromal cells, mesenchymal stem cells, etc.). These solutions have been described as a potential treatment for cartilage and meniscal repair or replacement. See, also, International Publications WO 99/51719 to Fofonoff, published Oct. 14, 1999; WO01/91672 to Simon et al., published Dec. 6, 2001; and WO01/17463 to Mannsmann, published Mar. 15, 2001; U.S. Pat. No. 6,283,980 B1 to Vibe-Hansen et al., issued Sep. 4, 2001, U.S. Pat. No. 5,842,477 to Naughton issued Dec. 1, 1998, U.S. Pat. No. 5,769,899 to Schwartz et al. issued Jun. 23, 1998, U.S. Pat. No. 4,609,551 to Caplan et al. issued Sep. 2, 1986, U.S. Pat. No. 5,041,138 to Vacanti et al. issued Aug. 29, 1991, U.S. Pat. No. 5,197,985 to Caplan et al. issued Mar. 30, 1993, U.S. Pat. No. 5,226,914 to Caplan et al. issued Jul. 13, 1993, U.S. Pat. No. 6,328,765 to Hardwick et al. issued Dec. 11, 2001, U.S. Pat. No. 6,281,195 to Rueger et al. issued Aug. 28, 2001, and U.S. Pat. No. 4,846,835 to Grande issued Jul. 11, 1989. However, clinical outcomes with biologic replacement materials such as allograft and autograft systems and tissue scaffolds have been uncertain since most of these materials cannot achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g. for cosmetic repairs, or metal alloys. See, e.g., U.S. Pat. No. 6,383,228 to Schmotzer, issued May 7, 2002; U.S. Pat. No. 6,203,576 to Afriat et al., issued Mar. 20, 2001; U.S. Pat. No. 6,126,690 to Ateshian, et al., issued Oct. 3, 2000. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

Further, joint arthroplasties are highly invasive and require surgical resection of the entire or the majority of the articular surface of one or more bones. With these procedures, the marrow space is reamed in order to fit the stem of the prosthesis. The reaming results in a loss of the patient's bone stock. U.S. Pat. No. 5,593,450 to Scott et al. issued Jan. 14, 1997 discloses an oval domed shaped patella prosthesis. The prosthesis has a femoral component that includes two condyles as articulating surfaces. The two condyles meet to form a second trochlear groove and ride on a tibial component that articulates with respect to the femoral component. A patella component is provided to engage the trochlear groove. U.S. Pat. No. 6,090,144 to Letot et al. issued Jul. 18, 2000 discloses a knee prosthesis that includes a tibial component and a meniscal component that is adapted to be engaged with the tibial component through an asymmetrical engagement.

Another joint subject to invasive joint procedures is the hip. U.S. Pat. No. 6,262,948 to Storer et al. issued Sep. 30, 2003 discloses a femoral hip prosthesis that replaces the natural femoral head. U.S. Patent Publications 2002/0143402 A1 and 2003/0120347 to Steinberg published Oct. 3, 2002 and Jun. 26, 2003, respectively, also disclose a hip prosthesis that replaces the femoral head and provides a member for communicating with the ball portion of the socket within the hip joint.

A variety of materials can be used in replacing a joint with a prosthetic, for example, silicone, e.g. for cosmetic repairs, or suitable metal alloys are appropriate. See, e.g., U.S. Pat. No. 6,443,991 B1 to Running issued Sep. 3, 2002, U.S. Pat. No. 6,387,131 B1 to Miehlke et al. issued May 14, 2002; U.S. Pat. No. 6,383,228 to Schmotzer issued May 7, 2002; U.S. Pat. No. 6,344,059 B1 to Krakovits et al. issued Feb. 5, 1002; U.S. Pat. No. 6,203,576 to Afriat et al. issued Mar. 20, 2001; U.S. Pat. No. 6,126,690 to Ateshian et al. issued Oct. 3, 2000; U.S. Pat. No. 6,013,103 to Kaufman et al. issued Jan. 11, 2000. Implantation of these prosthetic devices is usually associated with loss of underlying tissue and bone without recovery of the full function allowed by the original cartilage and, with some devices, serious long-term complications associated with the loss of significant amounts of tissue and bone can cause loosening of the implant. One such complication is osteolysis. Once the prosthesis becomes loosened from the joint, regardless of the cause, the prosthesis will then need to be replaced. Since the patient's bone stock is limited, the number of possible replacement surgeries is also limited for joint arthroplasty.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, non-functional joint.

A variety of tools are available to assist surgeons in performing joint surgery. In the knee, for example, U.S. Pat. No. 4,501,266 to McDaniel issued Feb. 26, 1985 discloses a knee distraction device that facilitates knee arthroplasty. The device has an adjustable force calibration mechanism that enables the device to accommodate controlled selection of the ligament-tensioning force to be applied to the respective, opposing sides of the knee. U.S. Pat. No. 5,002,547 to Poggie et al. issued Mar. 26, 1991 discloses a modular apparatus for use in preparing the bone surface for implantation of a modular total knee prosthesis. The apparatus has cutting guides, templates, alignment devices along with a distractor and clamping instruments that provide modularity and facilitate bone resection and prosthesis implantation. U.S. Pat. No. 5,250,050 to Poggie et al. issued Oct. 5, 1993 is also directed to a modular apparatus for use in preparing a bone surface for the implantation of a modular total knee prosthesis. U.S. Pat. No. 5,387,216 to Thornhill et al. issued Feb. 7, 1995 discloses instrumentation for use in knee revision surgery. A bearing sleeve is provided that is inserted into the damaged canal in order to take up additional volume. The rod passes through the sleeve and is positioned to meet the natural canal of the bone. The rod is then held in a fixed position by the bearing sleeve. A cutting guide can then be mounted on the rod for cutting the bone and to provide a mounting surface for the implant. U.S. Pat. No. 6,056,756 to Eng et al. issued May 2, 2000 discloses a tool for preparing the distal femoral end for a prosthetic implant. The tool lays out the resection for prosthetic replacement and includes a jack for pivotally supporting an opposing bone such that the jack raises the opposing bone in flexion to the spacing of the intended prosthesis. U.S. Pat. No. 6,106,529 to Techiera issued Aug. 22, 2000 discloses an epicondylar axis referencing drill guide for use in resection to prepare a bone end for prosthetic joint replacement. U.S. Pat. No. 6,296,646 to Williamson issued Oct. 2, 2001 discloses a system that allows a practitioner to position the leg in the alignment that is directed at the end of the implant procedure and to cut both the femur and tibia while the leg is fixed in alignment. U.S. Pat. No. 6,620,168 to Lombardi et al. issued Sep. 16, 2003 discloses a tool for intermedullary revision surgery along with tibial components.

U.S. Pat. No. 5,578,037 to Sanders et al. issued Nov. 26, 1996 discloses a surgical guide for femoral resection. The guide enables a surgeon to resect a femoral neck during a hip arthroplasty procedure so that the femoral prosthesis can be implanted to preserve or closely approximate the anatomic center of rotation of the hip.

U.S. Pat. No. 6,206,927 to Fell, et al., issued Mar. 27, 2001, and U.S. Pat. No. 6,558,421 to Fell, et al., issued May 6, 2003, disclose a surgically implantable knee prosthesis that does not require bone resection. This prosthesis is described as substantially elliptical in shape with one or more straight edges. Accordingly, these devices are not designed to substantially conform to the actual shape (contour) of the remaining cartilage in vivo and/or the underlying bone. Thus, integration of the implant can be extremely difficult due to differences in thickness and curvature between the patient's surrounding cartilage and/or the underlying subchondral bone and the prosthesis.

Interpositional knee devices that are not attached to both the tibia and femur have been described. For example, Platt et al. (1969) "Mould Arthroplasty of the Knee," Journal of Bone and Joint Surgery 51B(1):76-87, describes a hemi-arthroplasty with a convex undersurface that was not rigidly attached to the tibia. Devices that are attached to the bone have also been described. Two attachment designs are commonly used. The McKeever design is a cross-bar member, shaped like a "t" from a top perspective view, that extends from the bone mating surface of the device such that the "t" portion penetrates the bone surface while the surrounding surface from which the "t" extends abuts the bone surface. See McKeever, "Tibial Plateau Prosthesis," Chapter 7, p. 86. An alternative attachment design is the Macintosh design, which replaces the "t" shaped fin for a series of multiple flat serrations or teeth. See Potter, "Arthroplasty of the Knee with Tibial Metallic implants of the McKeever and Macintosh Design," Surg. Clins. Of North Am. 49(4): 903-915 (1969).

U.S. Pat. No. 4,502,161 to Wall issued Mar. 5, 1985, describes a prosthetic meniscus constructed from materials such as silicone rubber or Teflon with reinforcing materials of stainless steel or nylon strands. U.S. Pat. No. 4,085,466 to Goodfellow et al. issued Mar. 25, 1978, describes a meniscal component made from plastic materials. Reconstruction of meniscal lesions has also been attempted with carbon-fiber-polyurethane-poly (L-lactide). Leeslag, et al., Biological and Biomechanical Performance of Biomaterials (Christel et al., eds.) Elsevier Science Publishers B.V., Amsterdam. 1986. pp.

347-352. Reconstruction of meniscal lesions is also possible with bioresorbable materials and tissue scaffolds.

However, currently available devices do not always provide ideal alignment with the articular surfaces and the resultant joint congruity. Poor alignment and poor joint congruity can, for example, lead to instability of the joint. In the knee joint, instability typically manifests as a lateral instability of the joint.

Thus, there remains a need for compositions for joint repair, including methods and compositions that facilitate the integration between the cartilage replacement system and the surrounding cartilage. There is also a need for tools that increase the accuracy of cuts made to the bone in a joint in preparation for surgical implantation of, for example, an artificial joint.

SUMMARY OF THE INVENTION

The present invention provides novel devices and methods for replacing a portion (e.g., diseased area and/or area slightly larger than the diseased area) of a joint (e.g., cartilage and/or bone) with a non-pliable, non-liquid (e.g., hard) implant material, where the implant achieves a near anatomic fit with the surrounding structures and tissues. In cases where the devices and/or methods include an element associated with the underlying articular bone, the invention also provides that the bone-associated element achieves a near anatomic alignment with the subchondral bone. The invention also provides for the preparation of an implantation site with a single cut, or a few relatively small cuts.

In one aspect, the invention includes a method for providing articular replacement material, the method comprising the step of producing articular replacement (e.g., cartilage replacement material) of selected dimensions (e.g., size, thickness and/or curvature).

In another aspect, the invention includes a method of making cartilage repair material, the method comprising the steps of (a) measuring the dimensions (e.g., thickness, curvature and/or size) of the intended implantation site or the dimensions of the area surrounding the intended implantation site; and (b) providing cartilage replacement material that conforms to the measurements obtained in step (a). In certain aspects, step (a) comprises measuring the thickness of the cartilage surrounding the intended implantation site and measuring the curvature of the cartilage surrounding the intended implantation site. In other embodiments, step (a) comprises measuring the size of the intended implantation site and measuring the curvature of the cartilage surrounding the intended implantation site. In other embodiments, step (a) comprises measuring the thickness of the cartilage surrounding the intended implantation site, measuring the size of the intended implantation site, and measuring the curvature of the cartilage surrounding the intended implantation site. In other embodiments, step (a) comprises reconstructing the shape of healthy cartilage surface at the intended implantation site.

In any of the methods described herein, one or more components of the articular replacement material (e.g., the cartilage replacement material) can be non-pliable, non-liquid, solid or hard. The dimensions of the replacement material can be selected following intraoperative measurements. Measurements can also be made using imaging techniques such as ultrasound, MRI, CT scan, x-ray imaging obtained with x-ray dye and fluoroscopic imaging. A mechanical probe (with or without imaging capabilities) can also be used to select dimensions, for example an ultrasound probe, a laser, an optical probe and a deformable material or device.

In any of the methods described herein, the replacement material can be selected (for example, from a pre-existing library of repair systems), grown from cells and/or hardened from various materials. Thus, the material can be produced pre- or post-operatively. Furthermore, in any of the methods described herein the repair material can also be shaped (e.g., manually, automatically or by machine), for example using mechanical abrasion, laser ablation, radiofrequency ablation, cryoablation and/or enzymatic digestion.

In any of the methods described herein, the articular replacement material can comprise synthetic materials (e.g., metals, liquid metals, polymers, alloys or combinations thereof) or biological materials such as stem cells, fetal cells or chondrocyte cells.

In another aspect, the invention includes a method of repairing a cartilage in a subject, the method of comprising the step of implanting cartilage repair material prepared according to any of the methods described herein.

In yet another aspect, the invention provides a method of determining the curvature of an articular surface, the method comprising the step of intraoperatively measuring the curvature of the articular surface using a mechanical probe. The articular surface can comprise cartilage and/or subchondral bone. The mechanical probe (with or without imaging capabilities) can include, for example an ultrasound probe, a laser, an optical probe and/or a deformable material.

In a still further aspect, the invention provides a method of producing an articular replacement material comprising the step of providing an articular replacement material that conforms to the measurements obtained by any of the methods of described herein.

In a still further aspect, the invention includes a partial or full articular prosthesis comprising a first component comprising a cartilage replacement material; and an optional second component comprising one or more metals, wherein said second component can have a curvature similar to subchondral bone, wherein said prosthesis comprises less than about 80% of the articular surface. In certain embodiments, the first and/or second component comprises a non-pliable material (e.g., a metal, a polymer, a metal alloy, a solid biological material). Other materials that can be included in the first and/or second components include polymers, biological materials, metals, metal alloys or combinations thereof. Furthermore, one or both components can be smooth or porous (or porous coated) using any methods or mechanisms to achieve in-growth of bone known in the art. In certain embodiments, the first component exhibits biomechanical properties (e.g., elasticity, resistance to axial loading or shear forces) similar to articular cartilage. The first and/or second component can be bioresorbable and, in addition, the first or second components can be adapted to receive injections.

In another aspect, an articular prosthesis comprising an external surface located in the load bearing area of an articular surface, wherein the dimensions of said external surface achieve a near anatomic fit with the adjacent, underlying or opposing cartilage is provided. The prosthesis can comprise one or more metals or metal alloys.

In yet another aspect, an articular repair system comprising (a) cartilage replacement material, wherein said cartilage replacement material has a curvature similar to surrounding, adjacent, underlying or opposing cartilage; and (b) at least one non-biologic material, wherein said articular surface repair system comprises a portion of the articular surface equal to, smaller than, or greater than, the weight-bearing surface that is provided. In certain embodiments, the cartilage replacement material is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components can be adapted to receive injections.

In a still further aspect of the invention, an articular surface repair system comprising a first component comprising a cartilage replacement material, wherein said first component has dimensions similar to that of adjacent, surrounding, underlying or opposing cartilage; and a second component, wherein said second component has a curvature similar to subchondral bone, wherein said articular surface repair system comprises less than about 80% of the articular surface (e.g., a single femoral condyle, tibia, etc.) is provided. In certain embodiments, the first component is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components can be adapted to receive injections. In certain embodiments, the first component has a curvature and thickness similar to that of adjacent, underlying, opposing or surrounding cartilage. The thickness and/or curvature can vary across the implant material.

In a still further embodiment, a partial articular prosthesis comprising (a) a metal or metal alloy; and (b) an external surface located in the load bearing area of an articular surface, wherein the external surface designed to achieve a near anatomic fit with the adjacent surrounding, underlying or opposing cartilage is provided.

Any of the repair systems or prostheses described herein (e.g., the external surface) can comprise a polymeric material, for example attached to said metal or metal alloy. Any of the repair systems can be entirely composed of polymer. Further, any of the systems or prostheses described herein can be adapted to receive injections, for example, through an opening in the external surface of said cartilage replacement material (e.g., an opening in the external surface terminates in a plurality of openings on the bone surface). Bone cement, polymers, Liquid Metal, therapeutics, and/or other bioactive substances can be injected through the opening(s). In certain embodiments, bone cement is injected under pressure in order to achieve permeation of portions of the marrow space with bone cement. In addition, any of the repair systems or prostheses described herein can be anchored in bone marrow or in the subchondral bone itself. One or more anchoring extensions (e.g., pegs, pins, etc.) can extend through the bone and/or bone marrow.

In any of the embodiments and aspects described herein, the joint can be a knee, shoulder, hip, vertebrae, elbow, ankle, wrist etc.

In another aspect, a method of designing an articular implant comprising the steps of obtaining an image of a joint, wherein the image includes both normal cartilage and diseased cartilage; reconstructing dimensions of the diseased cartilage surface to correspond to normal cartilage; and designing the articular implant to match the dimensions of the reconstructed diseased cartilage surface or to match an area slightly greater than the diseased cartilage surface is provided. The image can be, for example, an intraoperative image including a surface detection method using any techniques known in the art, e.g., mechanical, optical ultrasound, and known devices such as MRI, CT, ultrasound, digital tomosynthesis and/or optical coherence tomography images. In certain embodiments, reconstruction is performed by obtaining a surface that follows the contour of the normal cartilage. The surface can be parametric and include control points that extend the contour of the normal cartilage to the diseased cartilage and/or a B-spline surface. In other embodiments, the reconstruction is performed by obtaining a binary image of cartilage by extracting cartilage from the image, wherein diseased cartilage appears as indentations in the binary image; and performing, for example, a morphological closing operation (e.g., performed in two or three dimensions using a structuring element and/or a dilation operation followed by an erosion operation) to determine the shape of an implant to fill the areas of diseased cartilage.

In yet another aspect, described herein are systems for evaluating the fit of an articular repair system into a joint, the systems comprising one or more computing means capable of superimposing a three-dimensional (e.g., three-dimensional representations of at least one articular structure and of the articular repair system) or a two-dimensional cross-sectional image (e.g., cross-sectional images reconstructed in multiple planes) of a joint and an image of an articular repair system to determine the fit of the articular repair system. The computing means can be: capable of merging the images of the joint and the articular repair system into a common coordinate system; capable of selecting an articular repair system having the best fit; capable of rotating or moving the images with respect to each other; and/or capable of highlighting areas of poor alignment between the articular repair system and the surrounding articular surfaces. The three-dimensional representations can be generated using a parametric surface representation.

In yet another aspect, surgical tools for preparing a joint to receive an implant are described, for example a tool comprising one or more surfaces or members that conform at least partially to the shape of the articular surfaces of the joint (e.g., a femoral condyle and/or tibial plateau of a knee joint). In certain embodiments, the tool comprises Lucite silastic and/or other polymers or suitable materials. The tool can be re-useable or single-use. The tool can be comprised of a single component or multiple components. In certain embodiments, the tool comprises an array of adjustable, closely spaced pins. In any embodiments described herein, the surgical tool can be designed to further comprise an aperture therein, for example one or more apertures having dimensions (e.g., diameter, depth, etc.) smaller or equal to one or more dimensions of the implant and/or one or more apertures adapted to receive one or more injectables. Any of the tools described herein can further include one or more curable (hardening) materials or compositions, for example that are injected through one or more apertures in the tool and which solidify to form an impression of the articular surface.

In still another aspect, a method of evaluating the fit of an articular repair system into a joint is described herein, the method comprising obtaining one or more three-dimensional images (e.g., three-dimensional representations of at least one articular structure and of the articular repair system) or two-dimensional cross-sectional images (e.g., cross-sectional images reconstructed in multiple planes) of a joint, wherein the joint includes at least one defect or diseased area; obtaining one or more images of one or more articular repair systems designed to repair the defect or diseased area; and evaluating the images to determine the articular repair system that best fits the defect (e.g., by superimposing the images to determine the fit of the articular repair system into the joint). In certain embodiments, the images of the joint and the articular repair system are merged into a common coordinate system. The three-dimensional representations can be generated using a parametric surface representation. In any of these methods, the evaluation can be performed by manual visual inspection and/or by computer (e.g., automated). The images can be obtained, for example, using a C-arm system and/or radiographic contrast.

In yet another aspect, described herein is a method of placing an implant into an articular surface having a defect or diseased area, the method comprising the step of imaging the joint using a C-arm system during placement of the implant, thereby accurately placing the implant into a defect or diseased area.

Also disclosed is a customizable, or patient specific, implant configured for placement between joint surfaces formed by inserting a hollow device having an aperture and a lumen into a target joint, and injecting material into the hollow device to form an implant.

A customizable, or patient specific, implant configured for placement between joint surfaces is also disclosed wherein the implant is formed by inserting a retaining device that engages at least a portion of one joint surface in a joint and injecting material into an aperture of the retaining device to form an implant.

The invention is also directed to tools. A is disclosed that tool comprises: a mold having a surface for engaging a joint surface; a block that communicates with the mold; and at least one guide aperture in the block. Another tool is disclosed that is formed at least partially in situ and comprises: a mold formed in situ using at least one of an inflatable hollow device or a retaining device to conform to the joint surface on at least one surface having a surface for engaging a joint surface; a block that communicates with the mold; and at least one guide aperture in the block.

A method of placing an implant into a joint is also provided. The method comprises the steps of imaging the joint using a C-arm system, obtaining a cross-sectional image with the C-arm system, and utilizing the image for placing the implant into a joint.

BRIEF DESCRIPTION OF THE DRAWINGS

FIG. 7A shows an example of normal thickness cartilage and a cartilage defect. FIG. 7B shows an imaging technique or a mechanical, optical, laser or ultrasound device measuring the thickness and detecting a sudden change in thickness indicating the margins of a cartilage defect. FIG. 7C shows a weight-bearing surface mapped onto the articular cartilage. FIG. 7D shows an intended implantation site and cartilage defect. FIG. 7E depicts placement of an exemplary single component articular surface repair system. FIG. 7F shows an exemplary multi-component articular surface repair system. FIG. 7G shows an exemplary single component articular surface repair system. FIG. 7H shows an exemplary multi-component articular surface repair system.

FIG. 8A shows a magnified view of an area of diseased cartilage. FIG. 8B shows a measurement of cartilage thickness adjacent to the defect. FIG. 8C depicts placement of a multi-component mini-prosthesis for articular resurfacing. FIG. 8D is a schematic depicting placement of a single component mini-prosthesis utilizing stems or pegs. FIG. 8E depicts placement of a single component mini-prosthesis utilizing stems and an opening for injection of bone cement.

FIG. 9A depicts normal thickness cartilage in the anterior and central and posterior portion of a femoral condyle and a large area of diseased cartilage in the posterior portion of the femoral condyle. FIG. 9B depicts placement of a single component articular surface repair system. FIG. 9C depicts a multi-component articular surface repair system.

FIGS. 11A-G illustrate, in cross-section, the use of an inflation device to form an implant. FIG. 11A illustrates a single lumen balloon inserted between two joint surfaces where the inflation occurs within the bounds of the joint. FIG. 11B illustrates another single lumen balloon inserted between two joint surfaces where the inflatable surfaces extend beyond a first and second edge of a joint. FIG. 11C illustrates another single lumen balloon between two joint surfaces. FIG. 11D illustrates a multi-balloon solution using two balloons where the balloons are adjacent to each other within the joint. FIG. 11E illustrates an alternative multi-balloon solution wherein a first balloon is comprised within a second balloon. FIG. 11F illustrates another multi-balloon solution where a first balloon lies within the lumen of a second balloon and further wherein the second balloon is adjacent a third balloon. FIG. 11G illustrates a 3 balloon configuration wherein a first balloon lies adjacent a second balloon and a third balloon fits within the lumen of one of the first or second balloon.

In FIG. 12A the inflation device enables the implant to achieve a surface conforming to the irregularities of the joint surface. In FIG. 12B the inflation device enables the implant to achieve a surface that sits above the irregular joint surface; FIG. 12C illustrates a device formed where a central portion of the device sits above the joint surface irregularities while the proximal and distal ends illustrated form a lateral abutting surface to the joint defects. FIG. 12D illustrates a device formed using a first inflation device within a second inflation device, with an exterior configuration similar to that shown in FIG. 12A; while FIG. 12E illustrates an alternative device formed using at least two different inflation devices having an exterior shape similar to the device shown in FIG. 12C.

FIGS. 14A-J illustrate the use of a retaining device to form an implant in situ.

FIG. 15A shows an exemplary single component articular surface repair system with varying curvature and radii. FIG. 15B depicts a multi-component articular surface repair system with a second component that mirrors the shape of the subchondral bone and a first component closely matches the shape and curvature of the surrounding normal cartilage.

FIG. 18B-D show various cross-sectional representations of the pegs: FIG. 18B shows a peg having a groove; FIG. 18C shows a peg with radially-extending arms that help anchor the device in the underlying bone; and FIG. 18D shows a peg with multiple grooves or flanges.

FIGS. 20B-E are overhead views of the implant showing that the shape of the peg need not be conical.

FIG. 27A-G illustrate patellar cutting blocks and molds used to prepare the patella for receiving a portion of a knee implant.

FIG. 28A-H illustrate femoral head cutting blocks and molds used to create a surface for receiving the femoral portion of a knee implant.

DETAILED DESCRIPTION OF THE INVENTION

Figure 1:
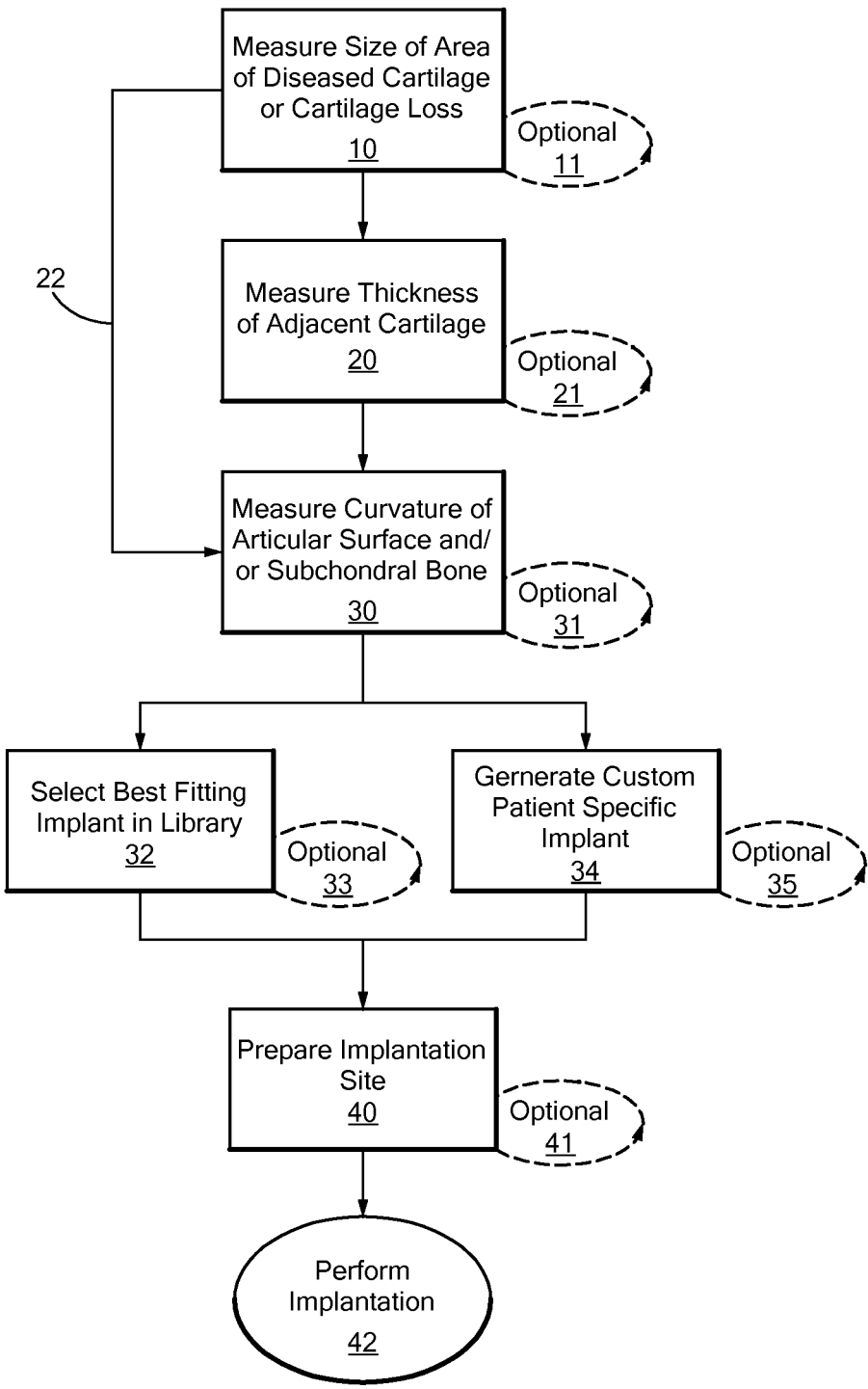
FIG. 1 is a flowchart depicting various methods of the present invention including, measuring the size of an area of diseased cartilage or cartilage loss, measuring the thickness of the adjacent cartilage, and measuring the curvature of the articular surface and/or subchondral bone. Based on this information, a best-fitting implant can be selected from a library of implants or a patient specific custom implant can be generated. The implantation site is subsequently prepared and the implantation is performed.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging ($2^{nd}$ Ed.), Jerrold T. Bushberg, et al.

The present invention provides methods and compositions for repairing joints, particularly for repairing articular cartilage and for facilitating the integration of a wide variety of cartilage repair materials into a subject. Among other things, the techniques described herein allow for the customization of cartilage repair material to suit a particular subject, for example in terms of size, cartilage thickness and/or curvature. When the shape (e.g., size, thickness and/or curvature) of the articular cartilage surface is an exact or near anatomic fit with the non-damaged cartilage or with the subject's original cartilage, the success of repair is enhanced. The repair material can be shaped prior to implantation and such shaping can be based, for example, on electronic images that provide information regarding curvature or thickness of any "normal" cartilage surrounding the defect and/or on curvature of the bone underlying the defect. Thus, the current invention provides, among other things, for minimally invasive methods for partial joint replacement. The methods will require only minimal or, in some instances, no loss in bone stock. Additionally, unlike with current techniques, the methods described herein will help to restore the integrity of the articular surface by achieving an exact or near anatomic match between the implant and the surrounding or adjacent cartilage and/or subchondral bone.

Advantages of the present invention can include, but are not limited to, (i) customization of joint repair, thereby enhancing the efficacy and comfort level for the patient following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; and (vi) improving postoperative joint congruity.

Thus, the methods described herein allow for the design and use of joint repair material that more precisely fits the defect (e.g., site of implantation) and, accordingly, provides improved repair of the joint.

I. Assessment of Joints and Alignment

The methods and compositions described herein can be used to treat defects resulting from disease of the cartilage (e.g., osteoarthritis), bone damage, cartilage damage, trauma, and/or degeneration due to overuse or age. The invention allows, among other things, a health practitioner to evaluate and treat such defects. The size, volume and shape of the area of interest can include only the region of cartilage that has the defect, but preferably will also include contiguous parts of the cartilage surrounding the cartilage defect.

As will be appreciated by those of skill in the art, size, curvature and/or thickness measurements can be obtained using any suitable technique. For example, one-dimensional, two-dimensional, and/or three-dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated by those of skill in the art, the thickness of the repair device can vary at any given point depending upon the depth of the damage to the cartilage and/or bone to be corrected at any particular location on an articular surface.

As illustrated in FIG. 1, typically the process begins by first measuring the size of the area of diseased cartilage or cartilage loss 10. Thereafter the user can optionally measure the thickness of adjacent cartilage 20. Once these steps are performed, the curvature of the articular surface is measured 30. Alternatively, the curvature of subchondral bone can be measured.

Once the size of the defect is known, either an implant can be selected from a library 32 or an implant can be generated based on the patient specific parameters obtained in the measurements and evaluation 34. Prior to installing the implant in the joint, the implantation site is prepared 40 and then the implant is installed 42. One or more of these steps can be repeated as necessary or desired as shown by the optional repeat steps 11, 21, 31, 33, 35, and 41.

A. Imaging Techniques

I. Thickness and Curvature

As will be appreciated by those of skill in the art, imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, ultrasound imaging techniques, and optical imaging techniques. (See, also, International Patent Publication WO 02/22014 to Alexander, et al., published Mar. 21, 2002; U.S. Pat. No. 6,373,250 to Tsoref et al., issued Apr. 16, 2002; and Vandeberg et al. (2002) *Radiology* 222:430-436). Contrast or other enhancing agents can be employed using any route of administration, e.g. intravenous, intra-articular, etc.

In certain embodiments, CT or MRI is used to assess tissue, bone, cartilage and any defects therein, for example cartilage lesions or areas of diseased cartilage, to obtain information on subchondral bone or cartilage degeneration and to provide morphologic or biochemical or biomechanical information about the area of damage. Specifically, changes such as fissuring, partial or full thickness cartilage loss, and signal changes within residual cartilage can be detected using one or more of these methods. For discussions of the basic NMR principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement (RARE) imaging, gradient echo acquisition in the steady state (GRASS), and driven equilibrium Fourier transform (DEFT) imaging, to obtain information on cartilage, see Alexander, et al., WO 02/22014. Other techniques include steady state free precision, flexible equilibrium MRI and DESS. Thus, in preferred embodiments, the measurements produced are based on three-dimensional images of the joint obtained as described in Alexander, et al., WO 02/22014 or sets of two-dimensional images ultimately yielding 3D information. Two-dimensional, and three-dimensional images, or maps, of the cartilage alone or in combination with a movement pattern of the joint, e.g. flexion—extension, translation and/or rotation, can be obtained. Three-dimensional images can include information on movement patterns, contact points, contact zone of two or more opposing articular surfaces, and movement of the contact point or zone during joint motion. Two- and three-dimensional images can include information on biochemical composition of the articular cartilage. In addition, imaging techniques can be compared over time, for example to provide up-to-date information on the shape and type of repair material needed.

As will be appreciated by those of skill in the art, imaging techniques can be combined, if desired. For example, C-arm imaging or x-ray fluoroscopy can be used for motion imaging, while MRI can yield high resolution cartilage information. C-arm imaging can be combined with intra-articular contrast to visualize the cartilage.

Figure 2:
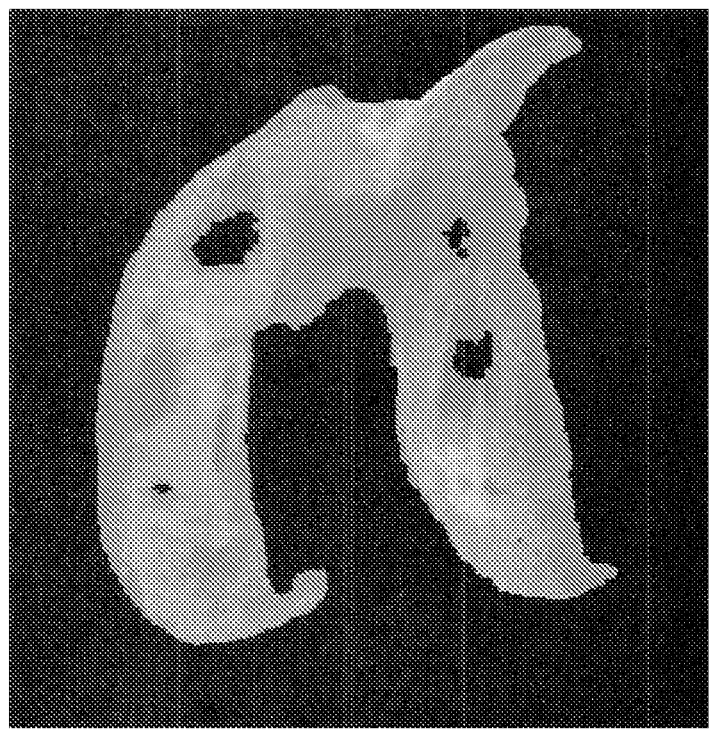
FIG. 2 is a reproduction of a three-dimensional thickness map of the articular cartilage of the distal femur. Three-dimensional thickness maps can be generated, for example, from ultrasound, CT or MRI data. Dark holes within the substances of the cartilage indicate areas of full thickness cartilage loss.

Any of the imaging devices described herein can also be used intra-operatively (see, also below), for example using a hand-held ultrasound and/or optical probe to image the articular surface intra-operatively. FIG. 2 illustrates a reproduction of a three-dimensional thickness map of the articular surface on the distal femur. The dark holes within the cartilage indicate areas of full cartilage loss.

ii. Anatomical and Mechanical Axes

Imaging can be used to determine the anatomical and biomechanical axes of an extremity associated with a joint. Suitable tests include, for example, an x-ray, or an x-ray combined with an MRI. Typically, anatomical landmarks are identified on the imaging test results (e.g., the x-ray film) and those landmarks are then utilized to directly or indirectly determine the desired axes. Thus, for example, if surgery is contemplated in a hip joint, knee joint, or ankle joint, an x-ray can be obtained. This x-ray can be a weight-bearing film of the extremity, for example, a full-length leg film taken while the patient is standing. This film can be used to determine the femoral and tibial anatomical axes and to estimate the biomechanical axes. As will be appreciated by those of skill in the art, these processes for identifying, e.g., anatomical and biomechanical axis of the joint can be applied to other joints without departing from the scope of the invention.

Anatomical and biomechanical axes can also be determined using other imaging modalities, including but not limited to, computed tomography and MRI. For example, a CT scan can be obtained through the hip joint, the knee joint, and the ankle joint. Optionally, the scan can be reformatted in the sagittal, coronal, or other planes. The CT images can then be utilized to identify anatomical landmarks and to determine the anatomical and biomechanical axes of the hip joint, knee joint, and/or ankle joint. Similarly, an MRI scan can be obtained for this purpose. For example, an MRI scan of the thigh and pelvic region can be obtained using a body coil or a torso phased array coil. A high resolution scan of the knee joint can be obtained using a dedicated extremity coil. A scan of the calf/tibia region and the ankle joint can be obtained again using a body coil or a torso phased array coil. Anatomical landmarks can be identified in each joint on these scans and the anatomical and biomechanical axes can be estimated using this information.

An imaging test obtained during weight-bearing conditions has some inherent advantages, in that it demonstrates normal as well as pathological loading and load distribution. A cross-sectional imaging study such as a CT scan or MRI scan has some advantages because it allows one to visualize and demonstrate the anatomical landmarks in three, rather than two, dimensions, thereby adding accuracy. Moreover, measurements can be performed in other planes, such as the sagittal or oblique planes, that may not be easily accessible in certain anatomical regions using conventional radiography. In principle, any imaging test can be utilized for this purpose.

The biomechanical axis can be defined as the axis going from the center of the femoral head, between the condylar surfaces and through the ankle joint.

Computed Tomography imaging has been shown to be highly accurate for the determination of the relative anatomical and biomechanical axes of the leg (Testi Debora, Zannoni Cinzia, Cappello Angelo and Viceconti Marco. "Border tracing algorithm implementation for the femoral geometry reconstruction." Comp. Meth. and Programs in Biomed., Feb. 14, 2000; Farrar M J, Newman R J, Mawhinney R R, King R. "Computed tomography scan scout film for measurement of femoral axis in knee arthroplasty." J. Arthroplasty. 1999 December; 14(8): 1030-1; Kim J S, Park T S, Park S B, Kim J S, Kim I Y, Kim S I. "Measurement of femoral neck anteversion in 3D. Part 1: 3D imaging method." Med. and Biol. Eng. and Computing. 38(6): 603-609, November 2000; Akagi M, Yamashita E, Nakagawa T, Asano T, Nakamura T. "Relationship between frontal knee alignment and reference axis in the distal femur." Clin. Ortho. and Related Res. No. 388, 147-156, 2001; Mahaisavariya B, Sitthiseripratip K, Tongdee T, Bohez E, Sloten J V, Oris P. "Morphological study of the proximal femur: a new method of geometrical assessment using 3 dimensional reverse engineering." Med. Eng. and Phys. 24 (2002) 617-622; Lam Li On, Shakespeare D. "Varus/Valgus alignment of the femoral component in total knee arthroplasty." The Knee, 10 (2003) 237-241).

The angles of the anatomical structures of the proximal and distal femur also show a certain variability level (i.e. standard deviation) comparable with the varus or valgus angle or the angle between the anatomical femoral axis and the biomechanical axis (Mahaisavariya B, Sitthiseripratip K, Tongdee T, Bohez E, Sloten J V, Oris P. "Morphological study of the proximal femur: a new method of geometrical assessment using 3 dimensional reverse engineering." Med. Eng. and Phys. 24 (2002) 617-622). Thus, a preferred approach for assessing the axes is based on CT scans of the hip, knee and ankle joint or femur rather than only of the knee region.

CT has been shown to be efficient in terms of the contrast of the bone tissue with respect to surrounding anatomical tissue so the bone structures corresponding to the femur and tibia can be extracted very accurately with semi automated computerized systems (Mahaisavariya B, Sitthiseripratip K, Tongdee T, Bohez E, Sloten J V, Oris P. "Morphological study of the proximal femur: a new method of geometrical assessment using 3 dimensional reverse engineering." Med. Eng. and Phys. 24 (2002) 617-622; Testi Debora, Zannoni Cinzia, Cappello Angelo and Viceconti Marco. "Border tracing algorithm implementation for the femoral geometry reconstruction." Comp. Meth. and Programs in Biomed., Feb. 14, 2000).

While 2-D CT has been shown to be accurate in the estimation of the biomechanical axis (Mahaisavariya B, Sitthiseripratip K, Tongdee T, Bohez E, Sloten J V, Oris P. "Morphological study of the proximal femur: a new method of geometrical assessment using 3 dimensional reverse engineering." Med. Eng. and Phys. 24 (2002) 617-622; Testi Debora, supra.; Lam Li On, Supra, 3-D CT has been shown to be more accurate for the estimation of the femoral anteversion angle (Kim J S, Park T S, Park S B, Kim J S, Kim I Y, Kim S I. Measurement of femoral neck anteversion in 3D. Part 1: 3D imaging method. Medical and Biological engineering and computing. 38(6): 603-609, November 2000; Kim J S, Park T S, Park S B, Kim J S, Kim I Y, Kim S I. Measurement of femoral neck anteversion in 3D. Part 1: 3D modeling method. Medical and Biological engineering and computing. 38(6): 610-616, November 2000). Farrar used simple CT 2-D scout views to estimate the femoral axis (Farrar M J, Newman R J, Mawhinney R R, King R. Computed tomography scan scout film for measurement of femoral axis in knee arthroplasty. J. Arthroplasty. 1999 December; 14(8): 1030-1).

In one embodiment, 2-D sagittal and coronal reconstructions of CT slice images are used to manually estimate the biomechanical axis. One skilled in the art can easily recognize many different ways to automate this process. For example, a CT scan covering at least the hip, knee and ankle region is acquired. This results in image slices (axial) which can be interpolated to generate the sagittal and coronal views.

Preprocessing (filtering) of the slice images can be used to improve the contrast of the bone regions so that they can be extracted accurately using simple thresholding or a more involved image segmentation tool like LiveWire or active contour models.

Identification of landmarks of interest like the centroid of the tibial shaft, the ankle joint, the intercondylar notch and the centroid of the femoral head can be performed. The biomechanical axis can be defined as the line connecting the proximal and the distal centroids, i.e. the femoral head centroid, the tibial or ankle joint centroid. The position of the intercondylar notch can be used for evaluation of possible deviations, errors or deformations including varus and valgus deformity.

In one embodiment, multiple imaging tests can be combined. For example, the anatomical and biomechanical axes can be estimated using a weight-bearing x-ray of the extremity or portions of the extremity. The anatomical information derived in this fashion can then be combined with a CT or MRI scan of one or more joints, such as a hip, knee, or ankle joint. Landmarks seen on radiography can then, for example, be cross-referenced on the CT or MRI scan. Axis measurements performed on radiography can be subsequently applied to the CT or MRI scans or other imaging modalities. Similarly, the information obtained from a CT scan can be compared with that obtained with an MRI or ultrasound scan. In one embodiment, image fusion of different imaging modalities can be performed. For example, if surgery is contemplated in a knee joint, a full-length weight-bearing x-ray of the lower extremity can be obtained. This can be supplemented by a spiral CT scan, optionally with intra-articular contrast of the knee joint providing high resolution three-dimensional anatomical characterization of the knee anatomy even including the menisci and cartilage. This information, along with the axis information provided by the radiograph can be utilized to select or derive therapies, such as implants or surgical instruments.

In certain embodiments, it may be desirable to characterize the shape and dimension of intra-articular structures, including subchondral bone or the cartilage. This can be done using a CT scan, preferably a spiral CT scan of one or more joints. The spiral CT scan can optionally be performed using intra-articular contrast. Alternatively, an MRI scan can be performed. If CT is utilized, a full spiral scan, or a few selected slices, can be obtained through neighboring joints. Typically, a full spiral scan providing full three-dimensional characterization would be obtained in the joint for which therapy is contemplated. If implants, or molds, for surgical instruments are selected or shaped, using this scan, the subchondral bone shape can be accurately determined from the resultant image data. A standard cartilage thickness and, similarly, a standard cartilage loss can be assumed in certain regions of the articular surface. For example, a standard thickness of 2 mm of the articular cartilage can be applied to the subchondral bone in the anterior third of the medial and lateral femoral condyles. Similarly, a standard thickness of 2 mm of the articular cartilage can be applied to the subchondral bone in the posterior third of the medial and lateral femoral condyles. A standard thickness of 0 mm of the articular cartilage can be applied in the central weight-bearing zone of the medial condyle, and a different value can be applied to the lateral condyle. The transition between these zones can be gradual, for example, from 2 mm to 0 mm. These standard values of estimated cartilage thickness and cartilage loss in different regions of the joint can optionally be derived from a reference database. The reference database can include categories such as age, body mass index ("BMI"), severity of disease, pain, severity of varus deformity, severity of valgus deformity, Kellgren-Lawrence score, along with other parameters that are determined to be relative and useful. Use of a standard thickness for the articular cartilage can facilitate the imaging protocols required for pre-operative planning.

Alternatively, however, the articular cartilage can be fully characterized by performing a spiral CT scan of the joint in the presence of intra-articular contrast or by performing an MRI scan using cartilage sensitive pulse sequences.

The techniques described herein can be used to obtain an image of a joint that is stationary, either weight bearing or not, or in motion or combinations thereof. Imaging studies that are obtained during joint motion can be useful for assessing the load bearing surface. This can be advantageous for designing or selecting implants, e.g. for selecting reinforcements in high load areas, for surgical tools and for implant placement, e.g. for optimizing implant alignment relative to high load areas.

B. Intraoperative Measurements

Alternatively, or in addition to, non-invasive imaging techniques described above, measurements of the size of an area of diseased cartilage or an area of cartilage loss, measurements of cartilage thickness and/or curvature of cartilage or bone can be obtained intraoperatively during arthroscopy or open arthrotomy. Intraoperative measurements can, but need not, involve actual contact with one or more areas of the articular surfaces.

Devices suitable for obtaining intraoperative measurements of cartilage or bone or other articular structures, and to generate a topographical map of the surface include but are not limited to, Placido disks and laser interferometers, and/or deformable materials or devices. (See, for example, U.S. Pat. No. 6,382,028 to Wooh et al., issued May 7, 2002; U.S. Pat. No. 6,057,927 to Levesque et al., issued May 2, 2000; U.S. Pat. No. 5,523,843 to Yamane et al. issued Jun. 4, 1996; U.S. Pat. No. 5,847,804 to Sarver et al. issued Dec. 8, 1998; and U.S. Pat. No. 5,684,562 to Fujieda, issued Nov. 4, 1997).

Figure 3A:
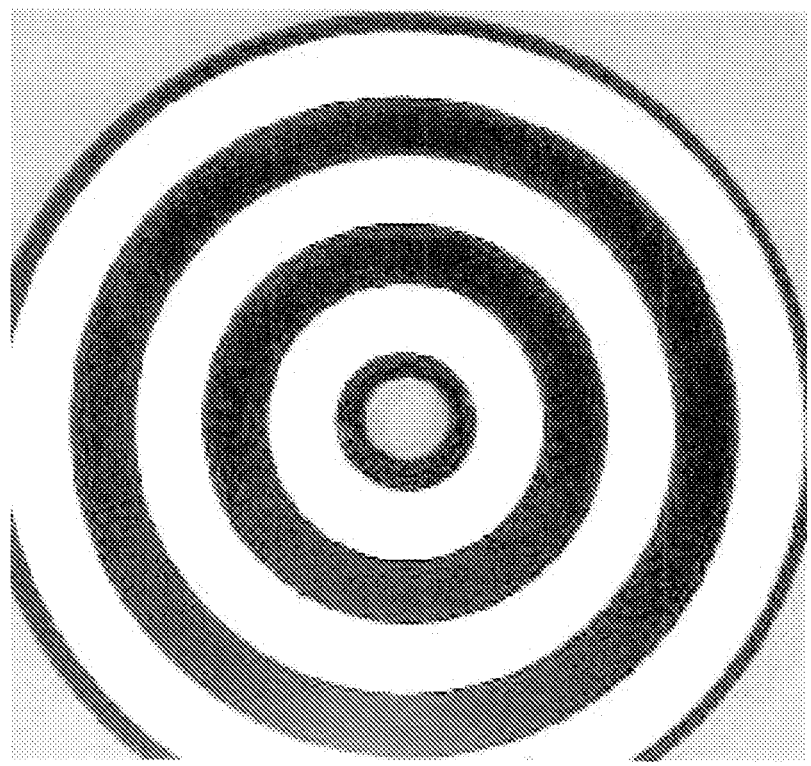
FIG. 3A shows an example of a Placido disc of concentrically arranged circles of light.
Figure 3B:
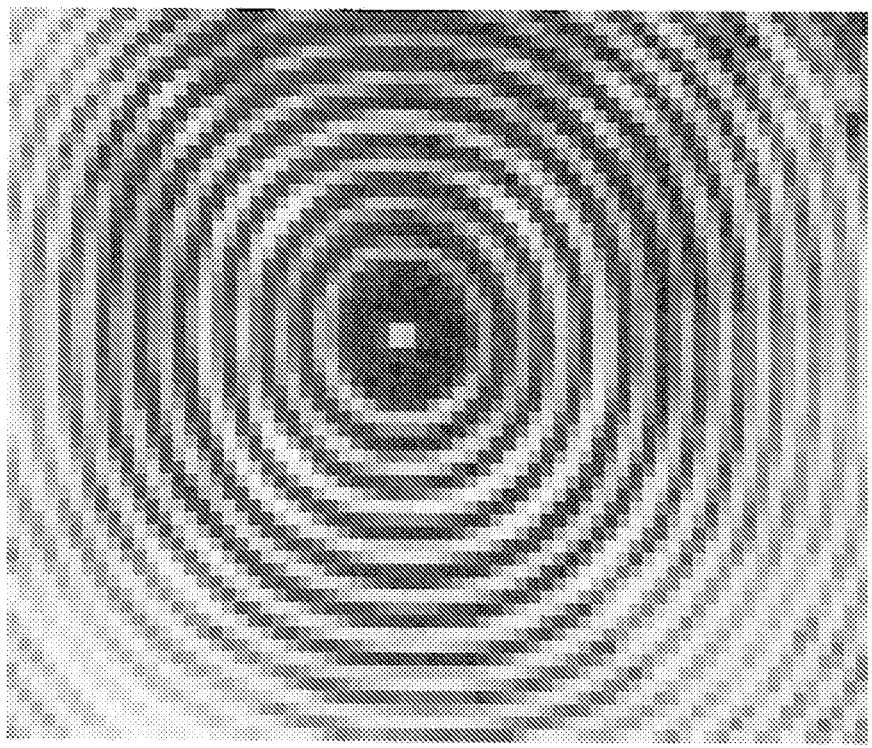
FIG. 3B shows an example of a projected Placido disc on a surface of fixed curvature.

FIG. 3A illustrates a Placido disk of concentrically arranged circles of light. The concentric arrays of the Placido disk project well-defined circles of light of varying radii, generated either with laser or white light transported via optical fiber. The Placido disk can be attached to the end of an endoscopic device (or to any probe, for example a hand-held probe) so that the circles of light are projected onto the cartilage surface. FIG. 3B illustrates an example of a Placido disk projected onto the surface of a fixed curvature. One or more imaging cameras can be used (e.g., attached to the device) to capture the reflection of the circles. Mathematical analysis is used to determine the surface curvature. The curvature can then, for example, be visualized on a monitor as a color-coded, topographical map of the cartilage surface. Additionally, a mathematical model of the topographical map can be used to determine the ideal surface topography to replace any cartilage defects in the area analyzed.

Figure 4:
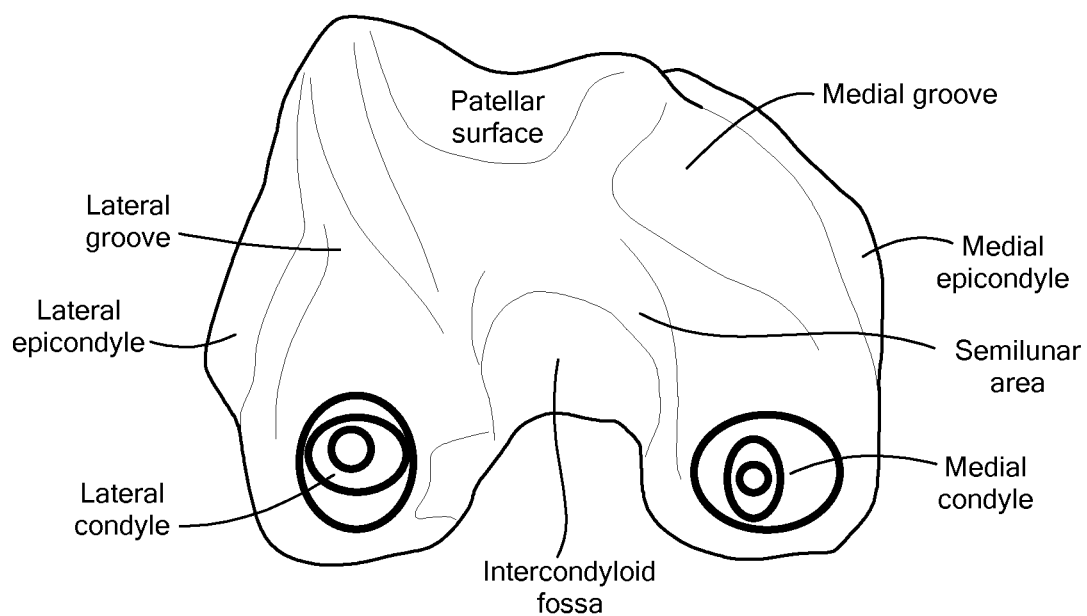
FIG. 4 shows a reflection resulting from a projection of concentric circles of light (Placido Disk) on each femoral condyle, demonstrating the effect of variation in surface contour on the reflected circles.

FIG. 4 shows a reflection resulting from the projection of concentric circles of light (Placido disk) on each femoral condyle, demonstrating the effect of variation in surface contour on reflected circles.

Similarly a laser interferometer can also be attached to the end of an endoscopic device. In addition, a small sensor can be attached to the device in order to determine the cartilage surface or bone curvature using phase shift interferometry, producing a fringe pattern analysis phase map (wave front) visualization of the cartilage surface. The curvature can then be visualized on a monitor as a color coded, topographical map of the cartilage surface. Additionally, a mathematical model of the topographical map can be used to determine the ideal surface topography to replace any cartilage or bone defects in the area analyzed. This computed, ideal surface, or surfaces, can then be visualized on the monitor, and can be used to select the curvature, or curvatures, of the replacement cartilage.

Figure 5:
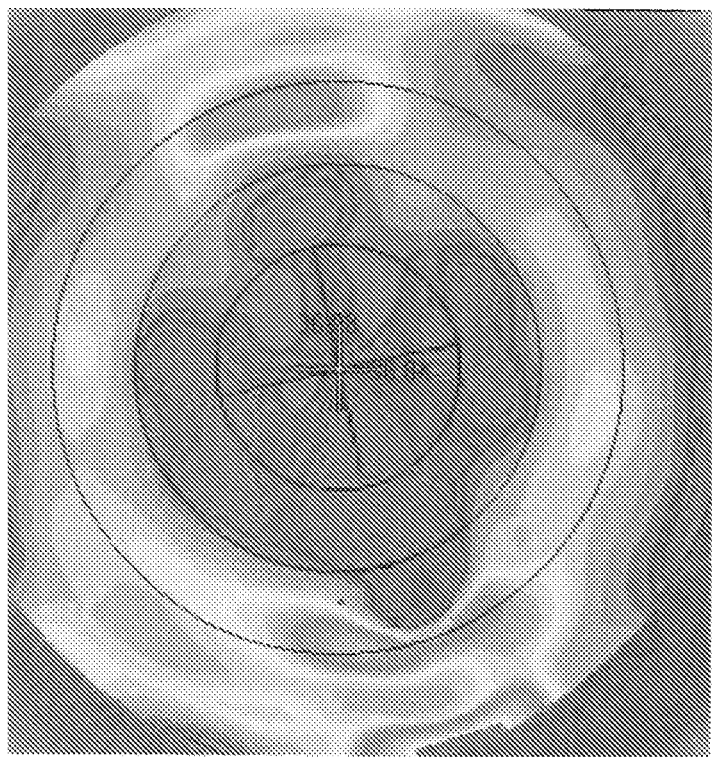
FIG. 5 shows an example of a 2D topographical map of an irregularly curved surface.
Figure 6:
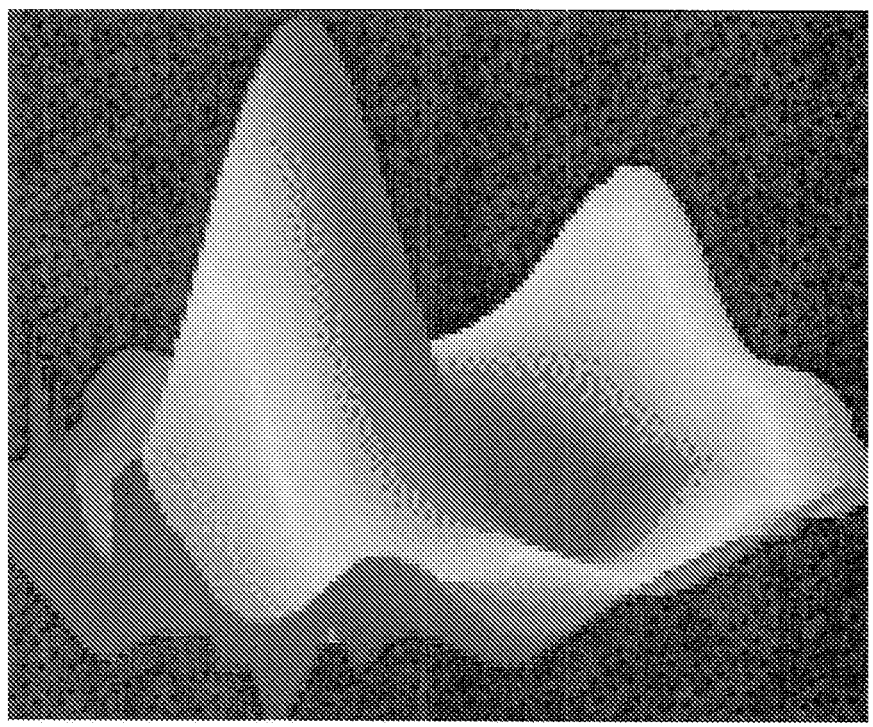
FIG. 6 shows an example of a 3D topographical map of an irregularly curved surface.

One skilled in the art will readily recognize that other techniques for optical measurements of the cartilage surface curvature can be employed without departing from the scope of the invention. For example, a 2-dimentional or 3-dimensional map, such as that shown in FIG. 5 and FIG. 6, can be generated.

Mechanical devices (e.g., probes) can also be used for intraoperative measurements, for example, deformable materials such as gels, molds, any hardening materials (e.g., materials that remain deformable until they are heated, cooled, or otherwise manipulated). See, e.g., WO 02/34310 to Dickson et al., published May 2, 2002. For example, a deformable gel can be applied to a femoral condyle. The side of the gel pointing towards the condyle can yield a negative impression of the surface contour of the condyle. The negative impression can then be used to determine the size of a defect, the depth of a defect and the curvature of the articular surface in and adjacent to a defect. This information can be used to select a therapy, e.g. an articular surface repair system. In another example, a hardening material can be applied to an articular surface, e.g. a femoral condyle or a tibial plateau. The hardening material can remain on the articular surface until hardening has occurred. The hardening material can then be removed from the articular surface. The side of the hardening material pointing towards the articular surface can yield a negative impression of the articular surface. The negative impression can then be used to determine the size of a defect, the depth of a defect and the curvature of the articular surface in and adjacent to a defect. This information can then be used to select a therapy, e.g. an articular surface repair system. In some embodiments, the hardening system can remain in place and form the actual articular surface repair system.

In certain embodiments, the deformable material comprises a plurality of individually moveable mechanical elements. When pressed against the surface of interest, each element can be pushed in the opposing direction and the extent to which it is pushed (deformed) can correspond to the curvature of the surface of interest. The device can include a brake mechanism so that the elements are maintained in the position that conforms to the surface of the cartilage and/or bone. The device can then be removed from the patient and analyzed for curvature. Alternatively, each individual moveable element can include markers indicating the amount and/or degree it is deformed at a given spot. A camera can be used to intra-operatively image the device and the image can be saved and analyzed for curvature information. Suitable markers include, but are not limited to, actual linear measurements (metric or empirical), different colors corresponding to different amounts of deformation and/or different shades or hues of the same color(s). Displacement of the moveable elements can also be measured using electronic means.

Other devices to measure cartilage and subchondral bone intraoperatively include, for example, ultrasound probes. An ultrasound probe, preferably handheld, can be applied to the cartilage and the curvature of the cartilage and/or the subchondral bone can be measured. Moreover, the size of a cartilage defect can be assessed and the thickness of the articular cartilage can be determined. Such ultrasound measurements can be obtained in A-mode, B-mode, or C-mode. If A-mode measurements are obtained, an operator can typically repeat the measurements with several different probe orientations, e.g. mediolateral and anteroposterior, in order to derive a three-dimensional assessment of size, curvature and thickness.

One skilled in the art will easily recognize that different probe designs are possible using the optical, laser interferometry, mechanical and ultrasound probes. The probes are preferably handheld. In certain embodiments, the probes or at least a portion of the probe, typically the portion that is in contact with the tissue, can be sterile. Sterility can be achieved with use of sterile covers, for example similar to those disclosed in WO 99/08598A1 to Lang, published Feb. 25, 1999.

Analysis on the curvature of the articular cartilage or subchondral bone using imaging tests and/or intraoperative measurements can be used to determine the size of an area of diseased cartilage or cartilage loss. For example, the curvature can change abruptly in areas of cartilage loss. Such abrupt or sudden changes in curvature can be used to detect the boundaries of diseased cartilage or cartilage defects.

As described above, measurements can be made while the joint is stationary, either weight bearing or not, or in motion.

II. Repair Materials

A wide variety of materials find use in the practice of the present invention, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage replacement or regenerating material having a curvature that will fit into a particular cartilage defect, will follow the contour and shape of the articular surface, and will match the thickness of the surrounding cartilage. The repair material can include any combination of materials, and typically include at least one non-pliable material, for example materials that are not easily bent or changed.

A. Metal and Polymeric Repair Materials

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat, et al. issued Mar. 20, 2001 and U.S. Pat. No. 6,322,588 to Ogle, et al. issued Nov. 27, 2001, and references cited therein. A wide-variety of metals are useful in the practice of the present invention, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl)methacrylamide], poly(hydroxy acids), poly(epsilon-caprolactone), polylactic acid, polyglycolic acid, poly(dimethyl glycolic acid), poly (hydroxy butyrate), and similar copolymers can also be used.

Other materials would also be appropriate, for example, the polyketone known as polyetheretherketone (PEEK™). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The implant can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof) or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

B. Biological Repair Material

Repair materials can also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. No. 5,478,739 to Slivka et al. issued Dec. 26, 1995; U.S. Pat. No. 5,842,477 to Naughton et al. issued Dec. 1, 1998; U.S. Pat. No. 6,283,980 to Vibe-Hansen et al., issued Sep. 4, 2001, and U.S. Pat. No. 6,365,405 to Salzmann et al. issued Apr. 2, 2002. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers can be bioresorbable.

Biological materials used in the methods described herein can be autografts (from the same subject); allografts (from another individual of the same species) and/or xenografts (from another species). See, also, International Patent Publications WO 02/22014 to Alexander et al. published Mar. 21, 2002 and WO 97/27885 to Lee published Aug. 7, 1997. In certain embodiments autologous materials are preferred, as they can carry a reduced risk of immunological complications to the host, including re-absorption of the materials, inflammation and/or scarring of the tissues surrounding the implant site.

In one embodiment of the invention, a probe is used to harvest tissue from a donor site and to prepare a recipient site. The donor site can be located in a xenograft, an allograft or an autograft. The probe is used to achieve a good anatomic match between the donor tissue sample and the recipient site. The probe is specifically designed to achieve a seamless or near seamless match between the donor tissue sample and the recipient site. The probe can, for example, be cylindrical. The distal end of the probe is typically sharp in order to facilitate tissue penetration. Additionally, the distal end of the probe is typically hollow in order to accept the tissue. The probe can have an edge at a defined distance from its distal end, e.g. at 1 cm distance from the distal end and the edge can be used to achieve a defined depth of tissue penetration for harvesting. The edge can be external or can be inside the hollow portion of the probe. For example, an orthopedic surgeon can take the probe and advance it with physical pressure into the cartilage, the subchondral bone and the underlying marrow in the case of a joint such as a knee joint. The surgeon can advance the probe until the external or internal edge reaches the cartilage surface. At that point, the edge will prevent further tissue penetration thereby achieving a constant and reproducible tissue penetration. The distal end of the probe can include one or more blades, saw-like structures, or tissue cutting mechanism. For example, the distal end of the probe can include an iris-like mechanism consisting of several small blades. The blade or blades can be moved using a manual, motorized or electrical mechanism thereby cutting through the tissue and separating the tissue sample from the underlying tissue. Typically, this will be repeated in the donor and the recipient. In the case of an iris-shaped blade mechanism, the individual blades can be moved so as to close the iris thereby separating the tissue sample from the donor site.

In another embodiment of the invention, a laser device or a radiofrequency device can be integrated inside the distal end of the probe. The laser device or the radiofrequency device can be used to cut through the tissue and to separate the tissue sample from the underlying tissue.

In one embodiment of the invention, the same probe can be used in the donor and in the recipient. In another embodiment, similarly shaped probes of slightly different physical dimensions can be used. For example, the probe used in the recipient can be slightly smaller than that used in the donor thereby achieving a tight fit between the tissue sample or tissue transplant and the recipient site. The probe used in the recipient can also be slightly shorter than that used in the donor thereby correcting for any tissue lost during the separation or cutting of the tissue sample from the underlying tissue in the donor material.

Any biological repair material can be sterilized to inactivate biological contaminants such as bacteria, viruses, yeasts, molds, mycoplasmas and parasites. Sterilization can be performed using any suitable technique, for example radiation, such as gamma radiation.

Any of the biological materials described herein can be harvested with use of a robotic device. The robotic device can use information from an electronic image for tissue harvesting.

In certain embodiments, the cartilage replacement material has a particular biochemical composition. For instance, the biochemical composition of the cartilage surrounding a defect can be assessed by taking tissue samples and chemical analysis or by imaging techniques. For example, WO 02/22014 to Alexander describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations. Biochemical composition of the cartilage replacement or regenerating material can, for example, be influenced by controlling concentrations and exposure times of certain nutrients and growth factors.

III. Devices Design

A. Cartilage Models

Using information on thickness and curvature of the cartilage, a physical model of the surfaces of the articular cartilage and of the underlying bone can be created. This physical model can be representative of a limited area within the joint or it can encompass the entire joint. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. As will be apparent, some, but not all, defects will include less than the entire cartilage. Thus, in one embodiment of the invention, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy (e.g., articular repair system) can be selected such that as much as possible of the healthy, surrounding tissue is preserved.

In other embodiments, the curvature of the articular surface can be measured to design and/or shape the repair material. Further, both the thickness of the remaining cartilage and the curvature of the articular surface can be measured to design and/or shape the repair material. Alternatively, the curvature of the subchondral bone can be measured and the resultant measurement(s) can be used to either select or shape a cartilage replacement material. For example, the contour of the subchondral bone can be used to re-create a virtual cartilage surface: the margins of an area of diseased cartilage can be identified. The subchondral bone shape in the diseased areas can be measured. A virtual contour can then be created by copying the subchondral bone surface into the cartilage surface, whereby the copy of the subchondral bone surface connects the margins of the area of diseased cartilage.

Figure 7A:
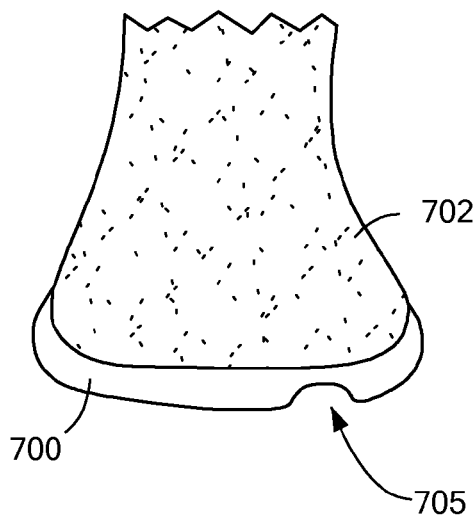
FIGS. 7A-H illustrate, in cross-section, various stages of knee resurfacing.
Figure 7B:
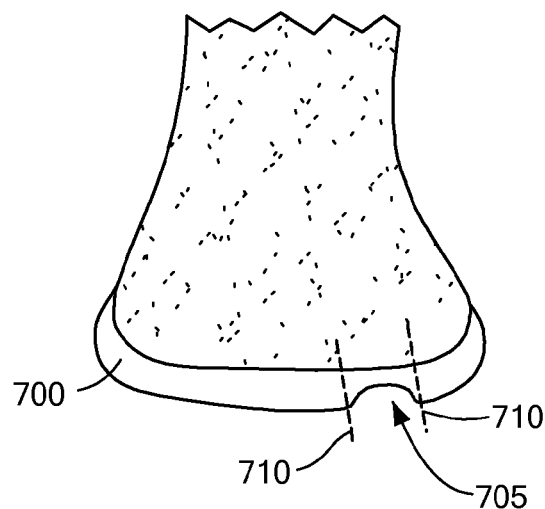
Figure 7C:
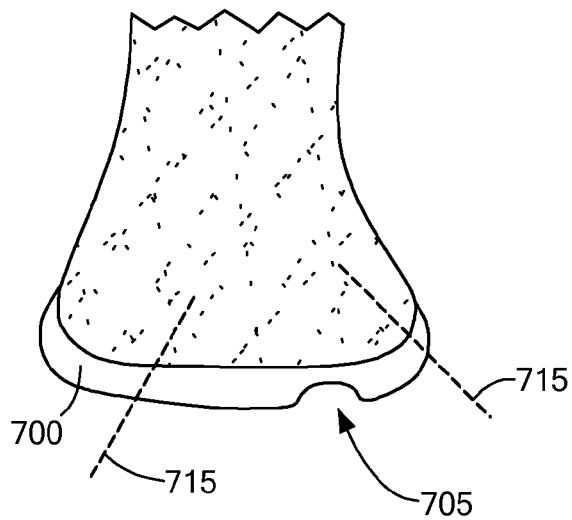

Turning now to FIGS. 7A-H, various stages of knee resurfacing steps are shown. FIG. 7A illustrates an example of normal thickness cartilage 700 in the anterior, central and posterior portion of a femoral condyle 702 with a cartilage defect 705 in the posterior portion of the femoral condyle. FIG. 7B shows the detection of a sudden change in thickness indicating the margins of a cartilage defect 710 that would be observed using the imaging techniques or the mechanical, optical, laser or ultrasound techniques described above. FIG. 7C shows the margins of a weight-bearing surface 715 mapped onto the articular cartilage 700. Cartilage defect 705 is located within the weight-bearing surface 715.

Figure 7D:
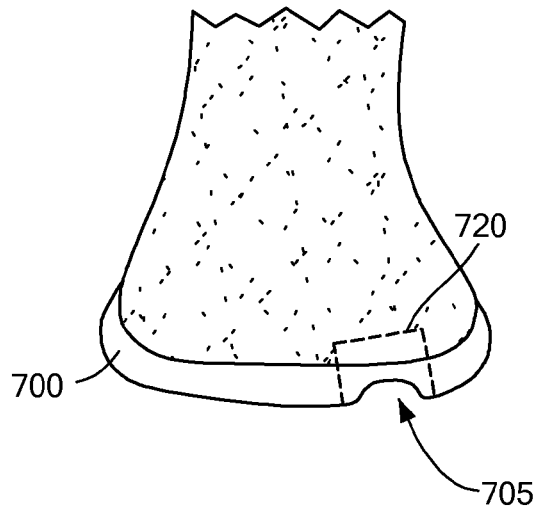
Figure 7E:
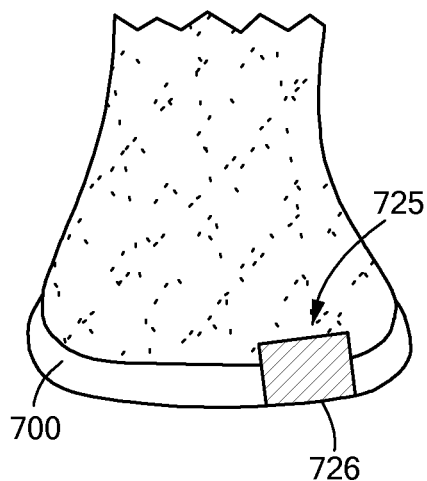

FIG. 7D shows an intended implantation site (stippled line) 720 and cartilage defect 705. In this depiction, the implantation site 720 is slightly larger than the area of diseased cartilage 705. FIG. 7E depicts placement of a single component articular surface repair system 725. The external surface of the articular surface repair system 726 has a curvature that seamlessly extends from the surrounding cartilage 700 resulting in good postoperative alignment between the surrounding normal cartilage 700 and the articular surface repair system 725.

Figure 7F:
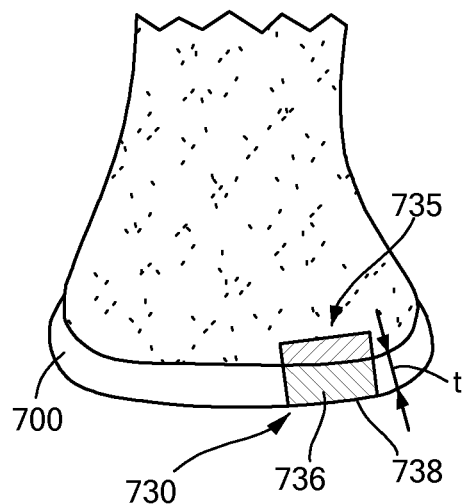

FIG. 7F shows an exemplary multi-component articular surface repair system 730. The distal surface 733 of the second component 732 has a curvature that extends from that of the adjacent subchondral bone 735. The first component 736 has a thickness t and surface curvature 738 that extends from the surrounding normal cartilage 700. In this embodiment, the second component 732 could be formed from a material with a Shore or Rockwell hardness that is greater than the material forming the first component 736, if desired. Thus it is contemplated that the second component 732 having at least portion of the component in communication with the bone of the joint is harder than the first component 736 which extends from the typically naturally softer cartilage material. Other configurations, of course, are possible without departing from the scope of the invention.

By providing a softer first component 736 and a firmer second component 732, the overall implant can be configured so that its relative hardness is analogous to that of the bone-cartilage or bone-meniscus area that it abuts. Thus, the softer material first component 736, being formed of a softer material, could perform the cushioning function of the nearby meniscus or cartilage.

Figure 7G:
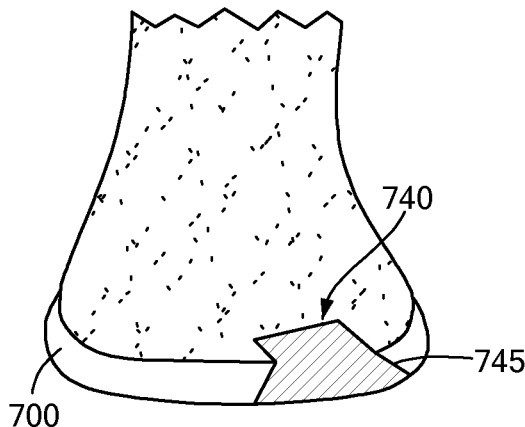
Figure 7H:
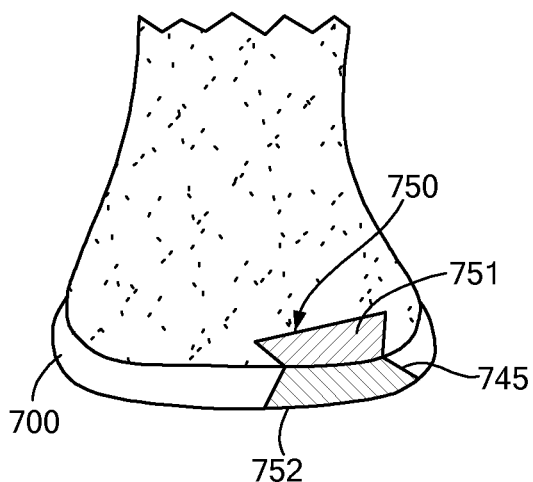

FIG. 7G shows another single component articular surface repair system 740 with a peripheral margin 745 which is configured so that it is substantially non-perpendicular to the surrounding or adjacent normal cartilage 700. FIG. 7H shows a multi-component articular surface repair system 750 with a first component 751 and a second component 752 similar to that shown in FIG. 7G with a peripheral margin 745 of the second component 745 substantially non-perpendicular to the surrounding or adjacent normal cartilage 700.

Figure 8A:
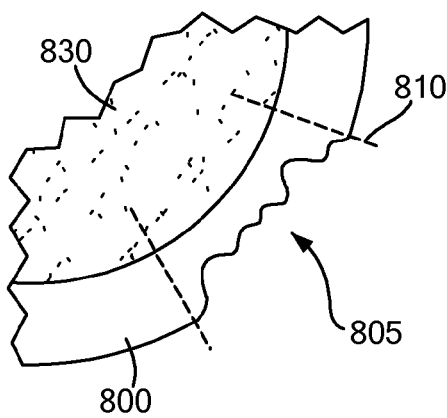
FIGS. 8A-E, illustrate, in cross-section, exemplary knee imaging and resurfacing.
Figure 8B:
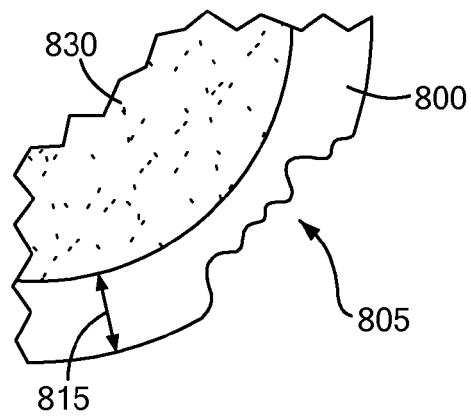
Figure 8C:
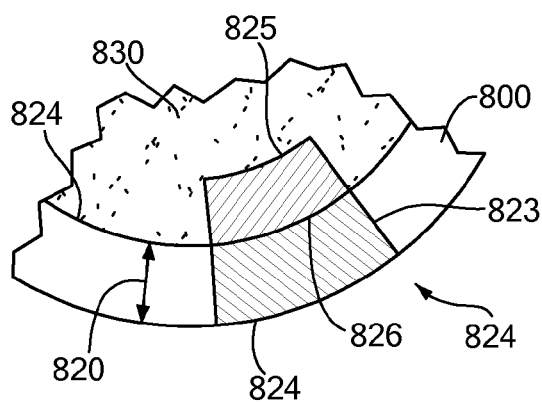

Now turning to FIGS. 8A-E, these figures depict exemplary knee imaging and resurfacing processes. FIG. 8A depicts a magnified view of an area of diseased cartilage 805 demonstrating decreased cartilage thickness when compared to the surrounding normal cartilage 800. The margins 810 of the defect have been determined. FIG. 8B depicts the measurement of cartilage thickness 815 adjacent to the defect 805. FIG. 8C depicts the placement of a multi-component mini-prosthesis 824 for articular resurfacing. The thickness 820 of the first component 823 closely approximates that of the adjacent normal cartilage 800. The thickness can vary in different regions of the prosthesis. The curvature of the distal portion 824 of the first component 823 closely approximates an extension of the normal cartilage 800 surrounding the defect. The curvature of the distal portion 826 of the second component 825 is a projection of the surface 827 of the adjacent subchondral bone 830 and can have a curvature that is the same, or substantially similar, to all or part of the surrounding subchondral bone.

Figure 8D:
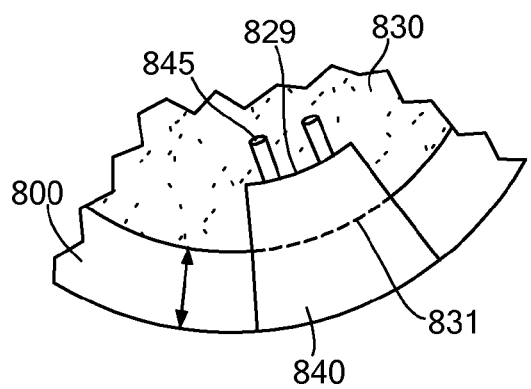

FIG. 8D is a schematic depicting placement of a single component mini-prosthesis 840 utilizing anchoring stems 845. As will be appreciated by those of skill in the art, a variety of configurations, including stems, posts, and nubs can be employed. Additionally, the component is depicted such that its internal surface 829 is located within the subchondral bone 830. In an alternative construction, the interior surface 829 conforms to the surface of the subchondral bone 831.

Figure 8E:
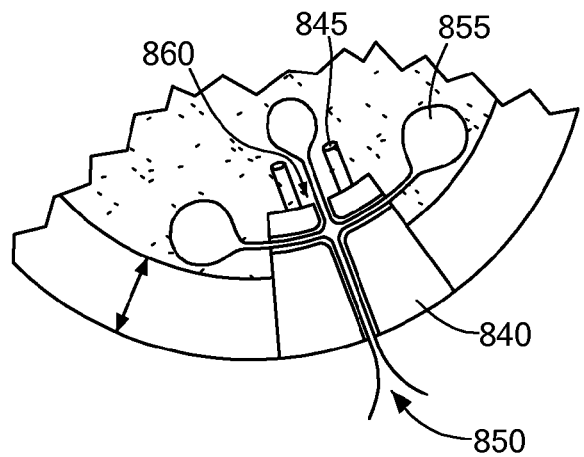

FIG. 8E depicts placement of a single component mini-prosthesis 840 utilizing anchoring stems 845 and an opening at the external surface 850 for injection of bone cement 855 or other suitable material. The injection material 855 can freely extravasate into the adjacent bone and marrow space from several openings at the undersurface of the mini-prosthesis 860 thereby anchoring the mini-prosthesis.

Figure 9A:
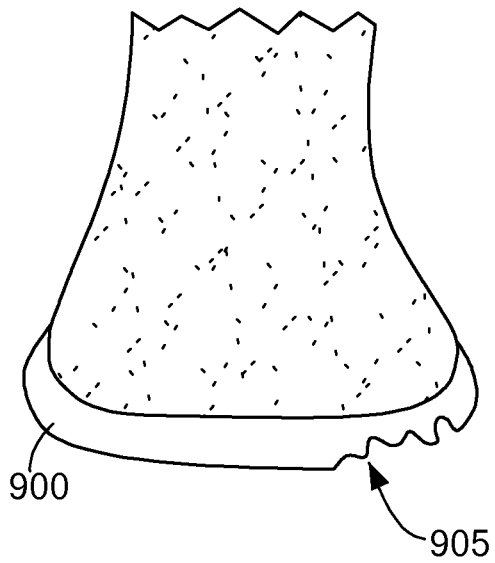
FIGS. 9A-C, illustrate, in cross-section, other exemplary knee resurfacing devices and methods.
Figure 9B:
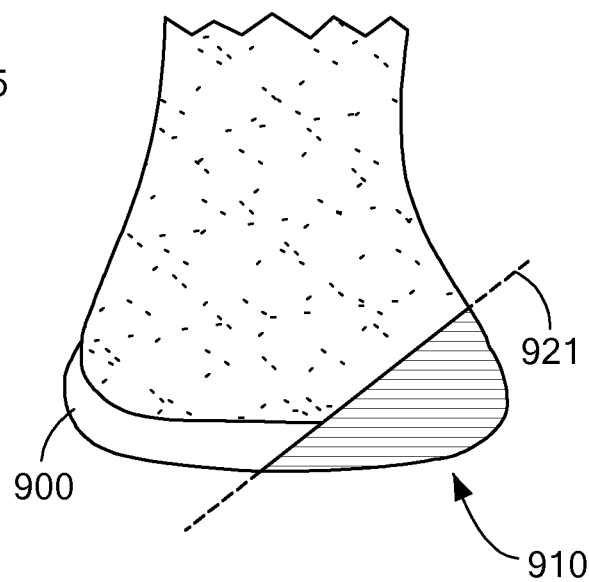
Figure 9C:
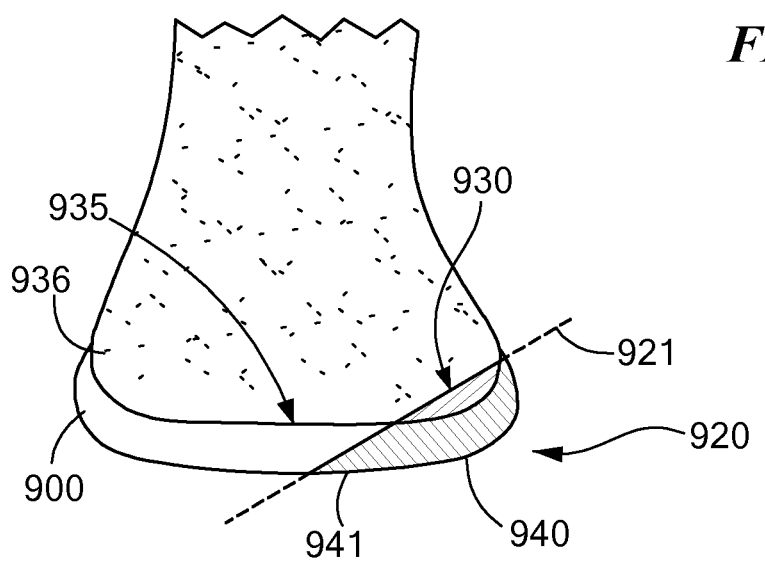

FIGS. 9A-C, depict an alternative knee resurfacing device. FIG. 9A depicts a normal thickness cartilage in the anterior, central and posterior portion of a femoral condyle 900 and a large area of diseased cartilage 905 toward the posterior portion of the femoral condyle. FIG. 9B depicts placement of a single component articular surface repair system 910. Again, the implantation site has been prepared with a single cut 921, as illustrated. However, as will be appreciated by those of skill in the art, the repair system can be perpendicular to the adjacent normal cartilage 900 without departing from the scope of the invention. The articular surface repair system is not perpendicular to the adjacent normal cartilage 900. FIG. 9C depicts a multi-component articular surface repair system 920. Again, the implantation site has been prepared with a single cut (cut line shown as 921). The second component 930 has a curvature similar to the extended surface 930 adjacent subchondral bone 935. The first component 940 has a curvature that extends from the adjacent cartilage 900.

B. Device Modeling In Situ

Figure 10A:
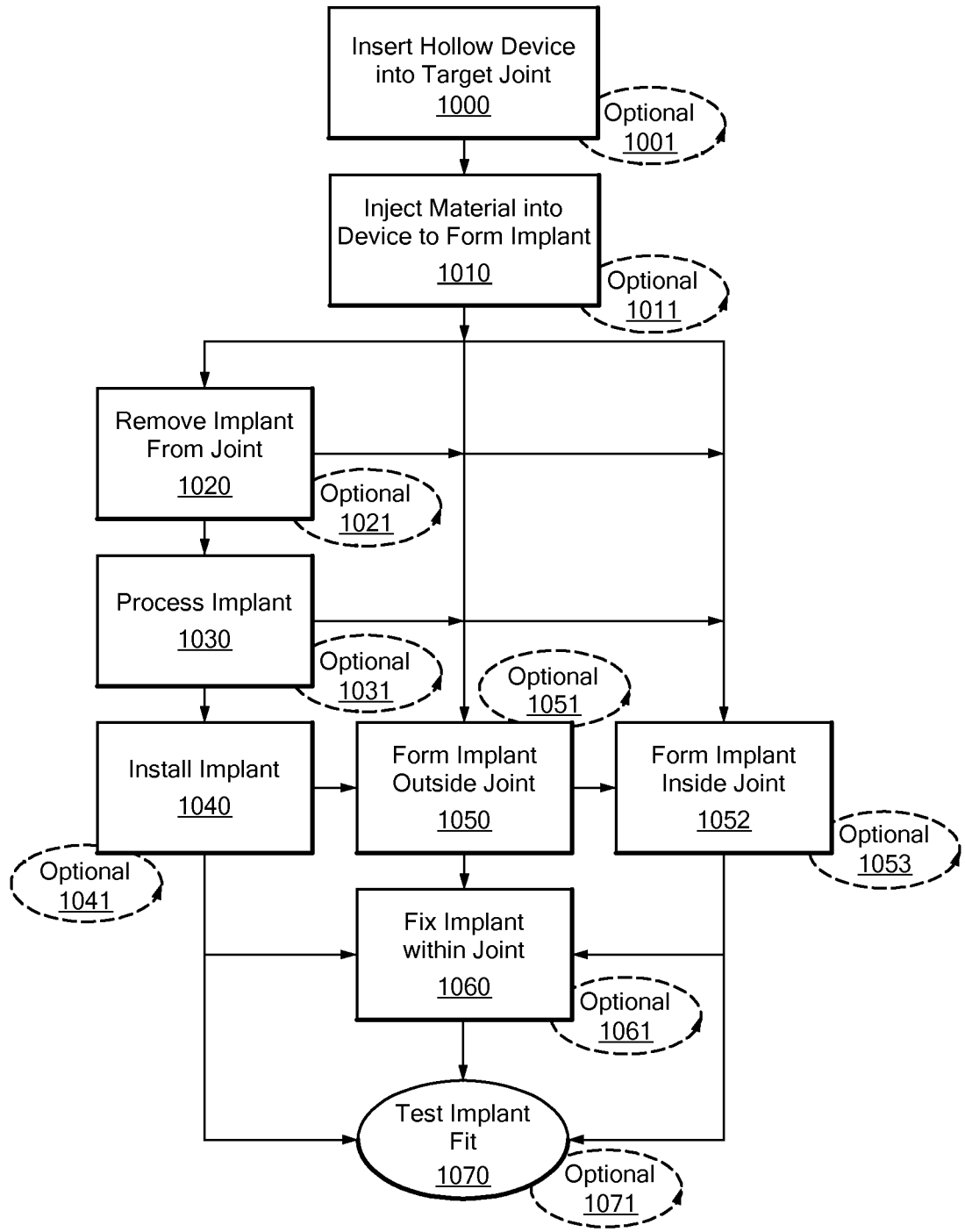
FIGS. 10A-B are flow charts illustrating steps for forming a device in situ.
Figure 10B:
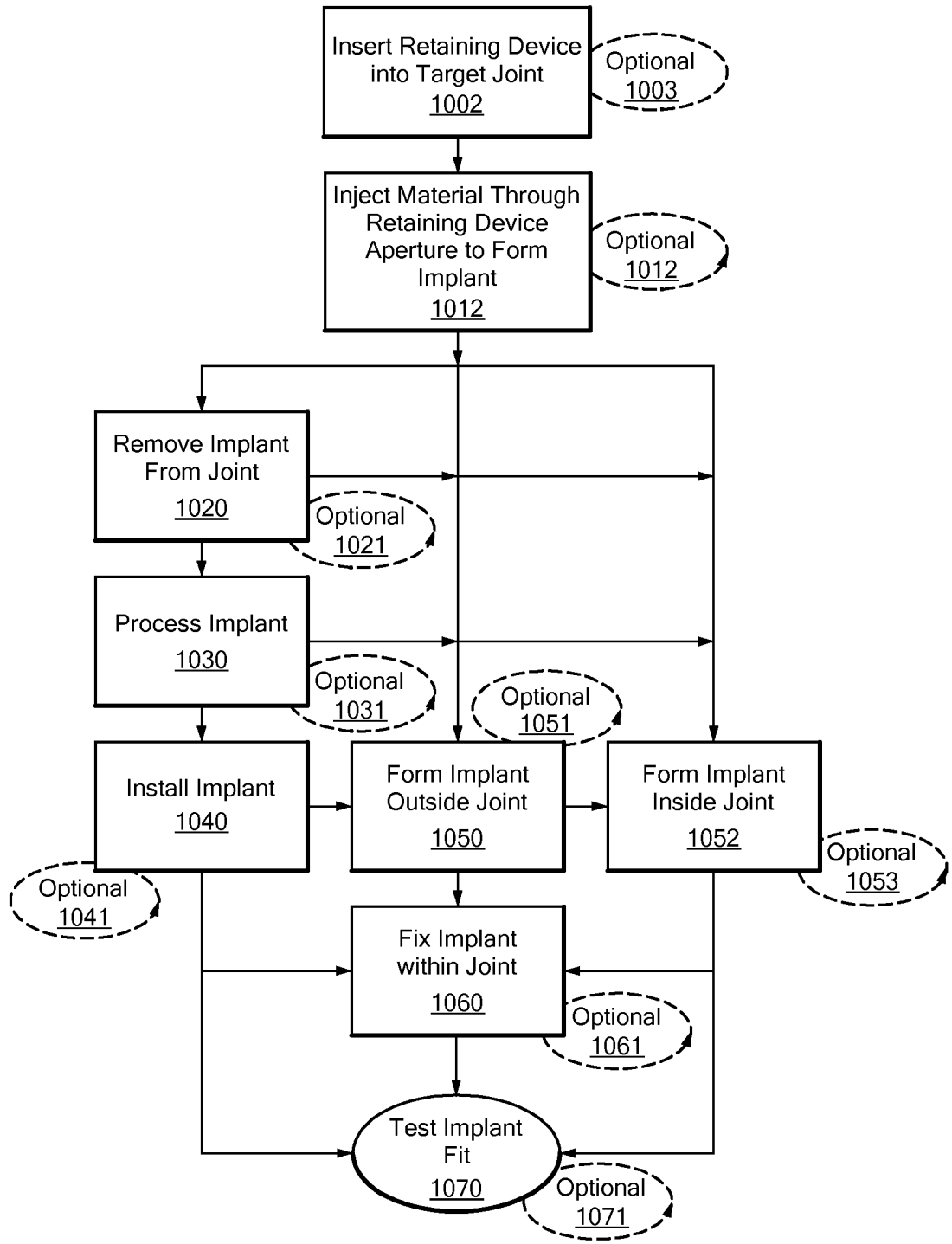
Figure 11E:
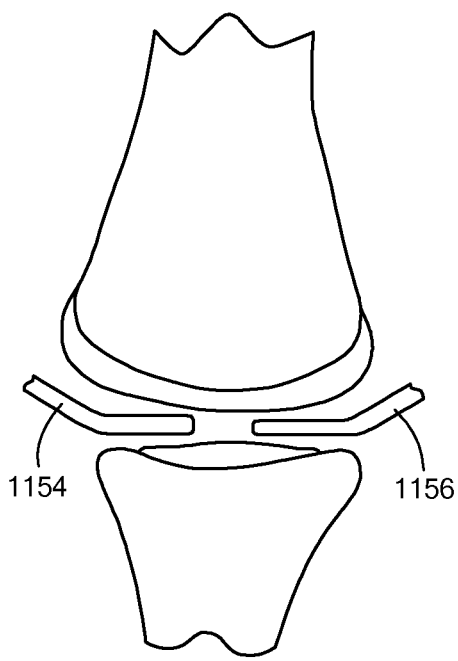
Figure 11F:
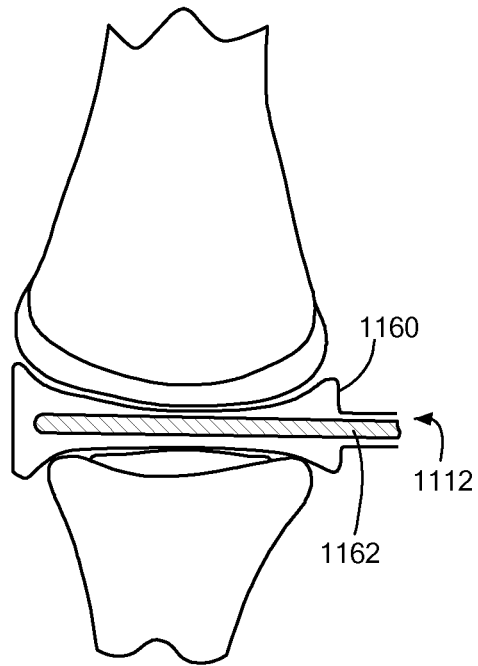
Figure 11G:
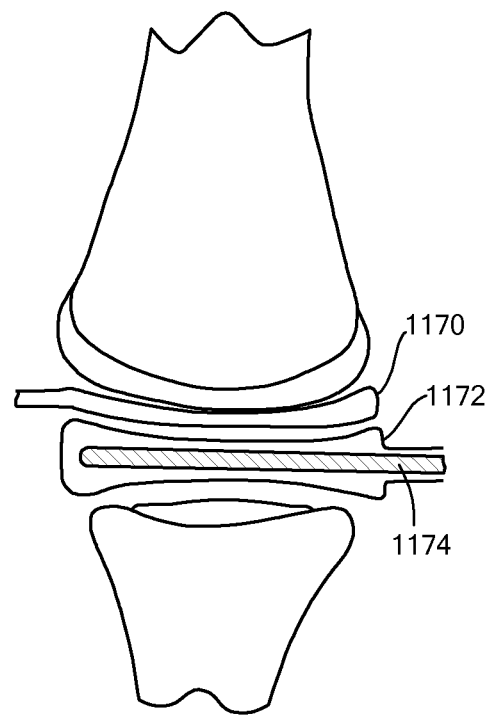

Another approach to repairing a defect is to model defect repair system in situ, as shown in FIGS. 10A-B. As shown in FIG. 10A, one approach would be to insert a hollow device, such as a balloon, into the target joint 1000. Any device capable of accepting, for example, injections of material would be suitable. Suitable injection materials include, for example, polymers and other materials discussed in Section II, above, can be used without departing from the scope of the invention.

In one embodiment it is contemplated that an insertion device has a substantially fixed shape that matches at least one articular surface or subchondral bone of the joint. After inserting the insertion device 1000, material is injected into the joint through the insertion device 1010 where it then hardens in situ, forming an implant 1052. The injection material can optionally bond to the device while hardening.

Alternatively, the implant can be removed after hardening 1020 for further processing 1030, such as polishing, e.g. as described Section IV.

Where the implant is removable after hardening in situ, it can be preferable to have the implant be formed so that it is collapsible, foldable or generally changeable in shape to facilitate removal. After processing, the implant can be reinstalled 1040.

One or more molds can be applied to one or more articular surfaces. The mold can have an internal surface facing the articular surface that substantially conforms to the shape of the articular cartilage and/or the shape of the subchondral bone. A hardening material including a polymer or metals can then be injected through an opening in the mold. The opening can include a membrane that allows insertion of an injection device such as a needle. The membrane helps to avoid reflux of the injected material into the joint cavity. Alternatively, the mold can be made of a material that provides sufficient structural rigidity to allow hardening of the injected substance with the proper shape while allowing for placement of needles and other devices through the mold.

Additionally, the implant device can be composed of a plurality of subcomponents, where the volume or size of each of the subcomponents is smaller than the volume of the implant. The different subcomponents can be connected or assembled prior to insertion into the joint 1050 (whether outside the body or adjacent the joint but within or substantially within the body), or, in some instances, can be assembled after insertion to the joint 1052. The subcomponents can be disassembled inside the joint, or adjacent the joint, once hardening of the injectable material has occurred.

Additionally, the implant can be fixed to the surface of the bone after implantation 1060 For example, fixation mechanisms can include mechanical structures such as fins, keels, teeth and pegs or non-mechanical means, such as bone cement, etc. Typically after the device is implanted and/or fixed within the joint, the functionality of the implant is tested 1070 to determine whether it enables the joint to engage in a desired range of motion. As will be appreciated by those of skill in the art, one or more of these steps can be repeated without departing from the scope of the invention, as shown by the optional repeat steps 1001, 1011, 1021, 1031, 1041, 1051, 1053, 1061 and 1071.

As shown in FIG. 10B, another approach would be to insert a retaining device into the target joint 1002. Any device capable of accepting, for example, injections of material would be suitable. Suitable materials include, for example, polymers and other materials discussed in Section II, above, can be used without departing from the scope of the invention.

In one embodiment it is contemplated that an insertion device has a substantially fixed shape that matches at least one articular surface or subchondral bone of the joint. After inserting the retaining device 1002, material is injected into a hollow area formed between the retaining device and the joint surface through an aperture 1012 where it then hardens in situ, forming an implant 1052. The injection material can optionally bond to the device while hardening.

Alternatively, the implant can be removed after hardening 1020 for further processing 1030, such as polishing, e.g. as described Section IV.

Where the implant is removable after hardening in situ, it can be preferable to have the implant be formed so that it is collapsible, foldable or generally changeable in shape to facilitate removal. After processing, the implant can be reinstalled 1040.

Additionally, the implant device can be composed of a plurality of subcomponents, where the volume or size of each of the subcomponents is smaller than the volume of the implant. The different subcomponents can be connected or assembled prior to insertion into the joint 1050 (whether outside the body or adjacent the joint but within or substantially within the body), or, in some instances, can be assembled after insertion to the joint 1052. The subcomponents can be disassembled inside the joint, or adjacent the joint, once hardening of the injectable material has occurred.

Additionally, the implant can be fixed to the surface of the bone after implantation 1060 For example, fixation mechanisms can include mechanical structures such as fins, keels, teeth and pegs or non-mechanical means, such as bone cement, etc. Typically after the device is implanted and/or fixed within the joint, the functionality of the implant is tested 1070 to determine whether it enables the joint to engage in a desired range of motion. As will be appreciated by those of skill in the art, one or more of these steps can be repeated without departing from the scope of the invention, as shown by the optional repeat steps 1003, 1013, 1021, 1031, 1041, 1051, 1053, 1061 and 1071.

Prior to performing the method shown in FIG. 10B, one or more holes or apertures can be drilled into the surface of the bone at an angle either perpendicular to the bone surface or set at an angle. Upon injecting material underneath the retaining device, the material embeds within the holes and form pegs upon hardening.

In one contemplated embodiment, at least a portion of the implantation device remains in situ after hardening of the injection material. In this scenario, the implantation device can be formed from a bio-resorbable material. In this instance, the container forming the implantation device can be resorbed, typically some time after hardening of the injection material.

The shape of the implantation device can be fixed. Where the shape is fixed, an imaging test or intraoperative measurement can be used to either shape or select the best fitting device for a particular patient, for example, using the imaging techniques and intraoperative measurement techniques described in SECTIONS IA-B, above.

In other embodiments, portions of the device can be rigid, or substantially rigid, while other portions of the device are deformable or malleable. Alternatively, a portion of the device can be relatively more rigid than another portion, without any requirement that any section be rigid, deformable or malleable, but that sections vary in hardness relative to another section. In this manner the shape of the rigid, substantially rigid, or relatively more rigid section can be determined, for example, using an imaging test. In contrast, it is possible that the malleable, deformable, or relatively more deformable portion of the implantation device can then take the shape of one or more articular surface in situ. This occurs particularly after the implantation material has been injected and while the material is hardening in situ. In still other embodiments, the entire device can be deformable.

In other embodiments, the implantation device can be expandable or collapsible. For example, a support structure such as a Nitinol™ mesh can be inserted into the joint. Insertion can occur via, for example, a catheter or an arthroscopy portal. Once inside the joint, the implantation device can then be expanded. The implantation device can include a receptacle, such as a bag, to receive the injection of hardening material, such as polyethylene or other liquid including metal preparations. The receptacle portion of the implantation device can be bio-resorbable and/or can bond with the injected material. Alternatively, the implantation device can be removed subsequent to injecting the material. Where a supporting material is used, the supporting material can be removed concurrently or subsequent to the removal of the implantation device, either via an incision or by collapsing the implantation device and removing it via, for example, the catheter or arthroscopy portal.

In another embodiment, a balloon such as that shown in FIGS. 11A-E, can be used as the implantation device. Different balloon shapes and sizes can be made available. A detailed description of all possible shapes and sizes for the balloons is not included to avoid obscuring the invention, but would be apparent to those of skill in the art. Where a balloon is used, it can be inserted into a joint and inflated. The size, height, shape and position of the balloon can be evaluated arthroscopically or via an open incision or using, for example, an imaging test relative to the articular surface and the other articular strictures. Range of motion testing can be performed in order to ensure adequate size, shape and position of the device during the full range of motion.

After insertion, the balloon can be slowly injected with, for example, a self-hardening material, or material that hardens upon activation. Suitable materials are described below and would be apparent to those of skill in the art. Typically, upon injection, the material is in a fluid or semi-fluid state. The material expands the balloon as it is injected which results in the balloon taking on the shape of the articular surface, for example as shown in FIG. 11A, and other articular structures such that it fills the defect.

The balloon can be slowly injected with a self hardening or hardening material such as a polymer and even metals. The material is initially in a fluid or semi-fluid state. The material expands the balloon whereby the shape of the balloon will take substantially the shape of the articular surface(s) and other articular structures. The polymer will subsequently harden inside the balloon thereby substantially taking the shape of the articular cavity and articular surface(s)/structures. The balloon can also be composed of a bio-resorbable material. The balloon can also be removed after the procedure.

Comparing, for example, the embodiments illustrated in FIGS. 11A-C, FIG. 11A illustrates a single balloon 1100 inserted between two joint surfaces 1102, 1104 of a joint 1110. In this figure, the joint surfaces are illustrated with associated cartilage 1106, 1108. The proximal end 1112 of the balloon is configured to communicate with a device that enables the balloon to be inflated, e.g. by filling the balloon 1100 with a substance. Substances include, but are not limited to, air, polymers, crystal free metals, or any other suitable material, such as those discussed in Section II above. The balloon 1100 of FIG. 11A is configured such that the distal end of the balloon 1114 does not extend beyond distal end of the joint 1120 (where the distal end of the joint is defined relative to the area of the joint where the balloon entered the joint).

FIG. 11B illustrates an alternative balloon 1130 wherein the distal end 1114 of the balloon 1130 and the proximal end 1113 of the balloon 1130 extends beyond the distal 1120 and proximal 1122 end of the joint. This extension can be optimized for flexion and extension by using different balloon sizes. FIG. 11C illustrates a balloon 1140 wherein the balloon 1140 is configured such that the distal end 1114 of the balloon 1140 extends beyond the distal 1120 of the joint while the proximal end 1114 of the balloon 1140 does not extend beyond the end of the joint. As will be appreciated by those of skill in the art, other permutations are possible without departing from the scope of the invention.

Additionally, a sharp instrument such as a scalpel can be inserted into the balloon or adjacent to the balloon and the balloon can be cut or slit. The balloon can then be pulled back from the hardened material and removed from the joint, preferably through a catheter or an arthroscopy portal.

More than one balloon can be used as illustrated in FIGS. 11D-G. Where a plurality of balloons used, the balloons can be configured such that the balloons are inserted side-by-side as shown by 1150, 1152 in FIG. 11D, inserted in different compartments as shown by 1154, 1156 in FIG. 11E, one or more balloons are encompassed within the lumen of another balloon, as shown by 1160, 1162 and 1170, 1172, 1174 in FIGS. 11F-G, in a top-bottom relationship, and/or combinations thereof.

Each balloon can have the same or different wall thickness or can be composed of the same or different materials. As a result of differences in material, a person of skill in the art will appreciate that the amount of pressure required to expand each of the balloons can vary either uniformly or in a non-uniform fashion. These pressures would be known to a person of skill in the art and are not discussed at length herein to avoid obscuring the invention.

For example, in one scenario the superior and inferior surface of a first, inner balloon, can have a low inflation pressure relative to a second balloon. Thus, as the material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant. This embodiment can be useful in areas within or bordering the contact zone of the articular surface.

A second outer or peripheral balloon can be provided that requires a higher inflation pressure relative to the first balloon. The inner, low inflation pressure balloon can be placed in the weight-bearing zone. The same balloon can also have different wall properties in different regions of the balloon, e.g. a rigid wall with high inflation pressures in the periphery and a less rigid wall with intermediate or low inflation pressures in the center.

Alternatively, a first balloon, having a low inflation pressure relative to a second balloon is provided in an area bordering the contact zone of the articular surface. Again, as material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant.

A second balloon can be provided at an area where there is relatively more weight bearing. This balloon can be configured to require a higher inflation pressure relative to the first balloon.

Differences in wall thickness, pressure tolerances and expandability of balloons can also be used to influence the resulting shape of the injected material.

Figure 12A:
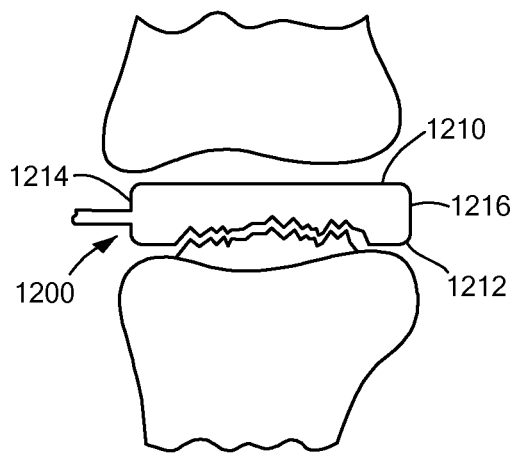
FIGS. 12A-E illustrate a variety of cross-sectional shapes achieved using balloons with variable wall thicknesses or material compositions.

The results of using inflation devices, or balloons, with differing wall thicknesses or pressure tolerances is shown in FIGS. 12A-F. As shown in FIG. 12A the balloon 1200 has an upper surface 1210 and a lower surface 1212 along with a proximal end 1214 and a distal end 1216. The relative pressure tolerance of the balloon or inflation device 1200 is lower on the lower surface 1212 than the upper surface 1210. As a result, the upper surface of the balloon 1210 has a relatively flat configuration relative to its corresponding joint surface while the lower surface 1212 has a relatively conforming shape relative to its corresponding joint surface.

Figure 12B:
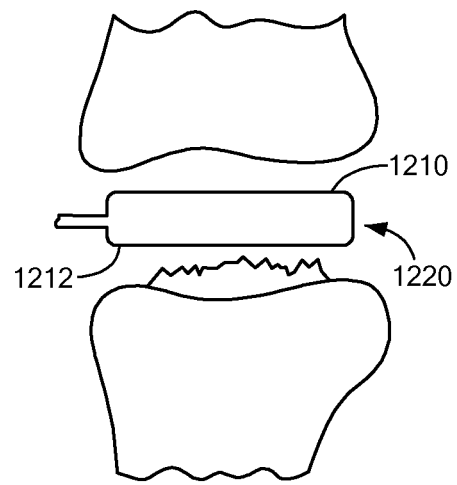

Turning now to FIG. 12B, the inflation device used 1220 has a relatively constant pressure tolerance that is relatively high which results in both the upper surface 1210 and the lower surface 1212 having relatively flat configurations relative to each of its corresponding joint surfaces, regardless of the joint surface anatomy.

Figure 12C:
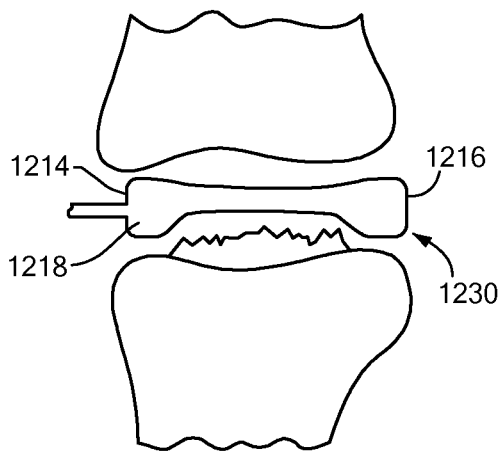

FIG. 12C illustrates a balloon 1230 having a low inflation pressure at its proximal 1214 and distal 1216 ends, with a higher inflation pressure at a central region 1218. The result of this configuration is that when the balloon is inflated, the proximal and distal ends inflate to a greater profile (e.g., height) than the central region. The inflation pressure of the central region, although higher than the proximal and distal ends, can be set such that the central region has a relatively flat configuration relative to the corresponding joint surfaces, as shown, or can be configured to achieve the result shown in FIG. 12A.

As will be appreciated by those of skill in the art, any of these balloons can be configured to have varying properties resulting in portions of the wall being less rigid than other portions, within the same balloon, e.g. a rigid wall with high inflation pressures in the periphery and a less rigid wall with intermediate or low inflation pressures in the center. Where there is more than one thickness to the balloon, it could, for example, have less stiffness anteriorly; greater stiffness centrally, and less stiffness posteriorly. The wall thickness variability will enable the device to accommodate shape formation. Central thickness will help prevent the device from fully conforming to the irregular surface of the joint, which may be important where there are irregularities to the joint surface, such as bone spurs. Alternatively, if the central portion is of less stiffness than the anterior and posterior sections, the device would be configured to conform more closely to the shape of the joint surface, including any irregularities. The closer the device conforms to the joint shape, the more the device seats within the joint.

Optionally, the surgeon can elect to remove surface irregularities, including bone spurs. This can be done using known techniques such as arthroscopy or open arthrotomy.

Where more than one balloon is used, the different balloons can have different shapes and sizes. Shape and size can be adjusted or selected for a given patient and joint. In addition to size and shape differences of the balloons, each of the balloons can also be configured to have different and/or varying wall thicknesses. For example, one balloon could be configured with a central portion that is less stiff than the anterior and posterior sections while a second balloon could be configured so that the central portion is of greater stiffness than the anterior and posterior section.

Figure 12D:
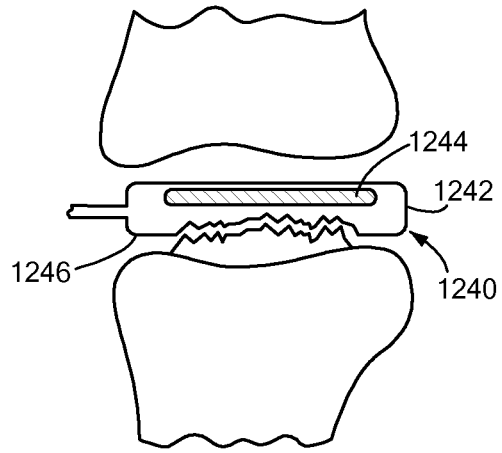
Figure 12E:
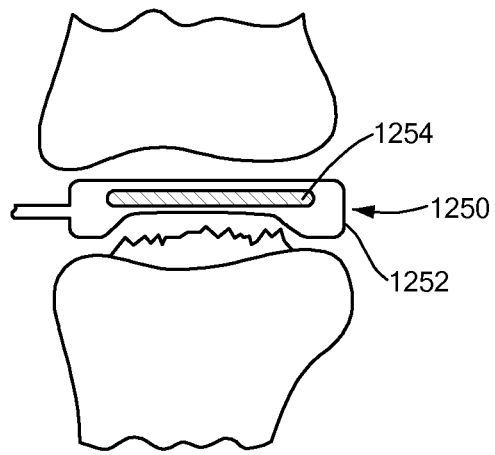

FIGS. 12D-E illustrate configurations using two balloons. As shown in FIG. 12D the first balloon 1244 sits within a second balloon 1242 to form an inflation device 1240. In this embodiment, the inferior surface 1246 of the external second balloon 1242 is configured with an inflation pressure that enables at least one surface of the device to conform, or substantially conform, to the corresponding joint surface. FIG. 12E also illustrates a two balloon configuration 1250 with a first balloon 1254 and a second balloon 1252. In this embodiment, the inflation pressure of the device is configured such that the surface does not substantially conform to the corresponding joint surface.

FIGS. 13A-J(1-3) illustrate a variety of cross-sections possible for the embodiments shown in FIGS. 11-12. These embodiments illustrate possible profiles achieved with a single balloon (FIGS. 13A(1-3)); a dual balloon embodiment wherein one balloon fits within a second balloon in approximately a central position (FIG. 13B(1-3)) or in an off-centered position within a second balloon (FIGS. 13D(1-3)); a tri-balloon set-up where two balloons fit within a first balloon (FIGS. 13C(1-3)), three balloons are positioned next to each other (FIGS. 13 H(1-3)), or two balloons are adjacent each other while one balloon has another balloon within its lumen (FIGS. 13E(2-3), F(2), G(2)); a four balloon set-up where two balloons are adjacent each other and each one has a balloon within its lumen (FIG. 13G(3)) or three balloons are adjacent each other with at least one of the three balloons having another balloon within its lumen (FIGS. 13I(2-3)), or a five balloon set up where three balloons are positioned adjacent each other and two of the three balloons have balloons within its lumen (FIG. 13J(1)). As will be appreciated by those of skill in the art, other combinations and profiles are achievable using the teachings of the invention without departing from the scope of the invention. All possible combinations have not been illustrated in order to avoid obscuring the invention.

In another embodiment, a probe can be inserted into the balloon or the device. The probe can be utilized for measuring the device thickness (e.g. minima and maxima). In this and other embodiments, the balloon can be initially injected with a test material that is typically not hardening. Once inside the balloon or the device, the thickness of the device or the balloon can be measured, e.g. for a given inflation pressure. In this manner, a sufficient minimum implant thickness can be ensured. Probes to measure the thickness of the device or the balloon include, but are not limited to ultrasound, including A-, B- or C-scan.

Figure 14A:
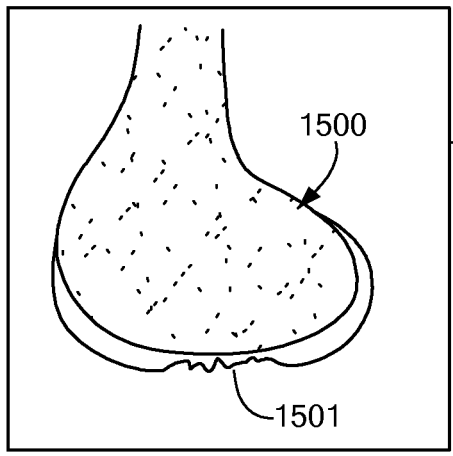
Figure 14D:
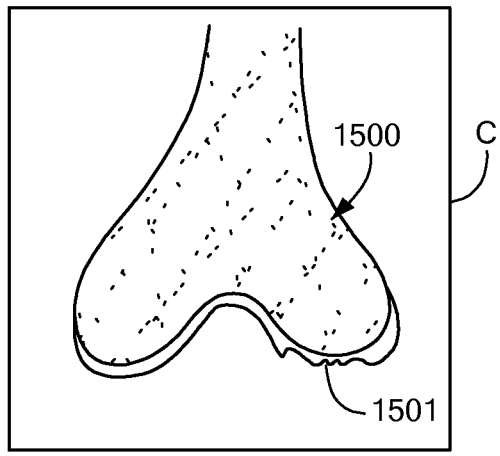
Figure 14B:
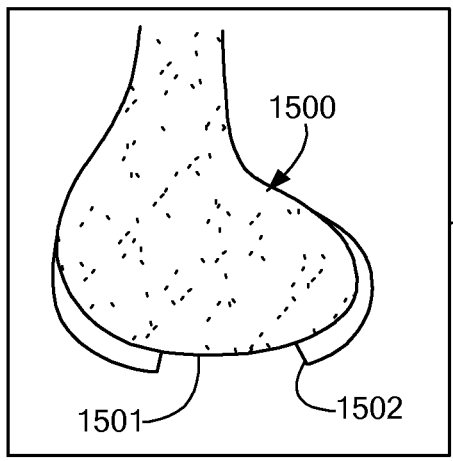
Figure 14E:
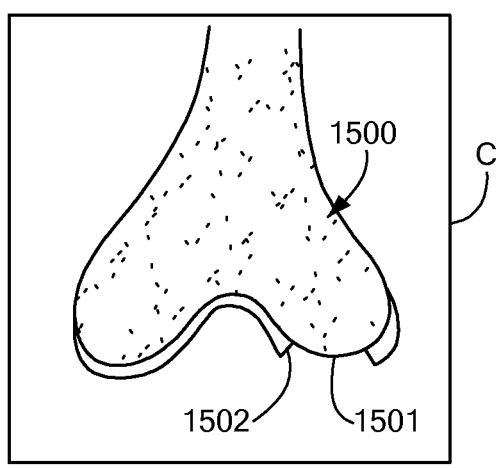
Figure 14C:
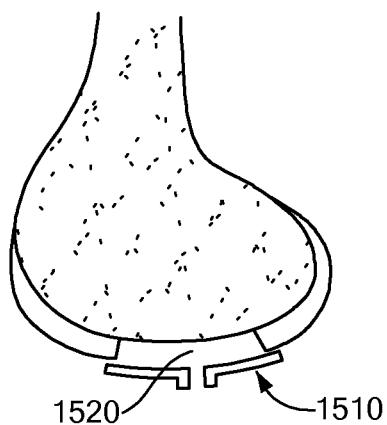
Figure 14F:
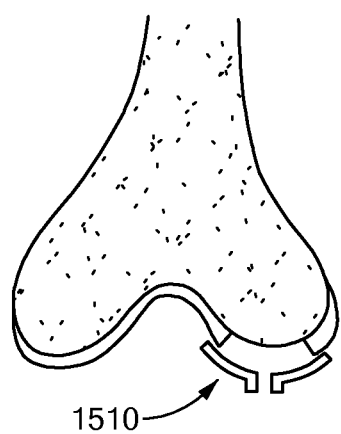

Turning now to FIGS. 14A-J which illustrate the cartilage repair system described in FIG. 10B utilizing the retaining device. FIGS. 14A and D illustrate a cartilage defect 1501 on an articular surface 1500 in the sagittal plane S and the coronal plane C. The surgeon debrides the defect thereby optionally creating smooth margins 1502.

A retaining device 1510 is applied to the defect 1501 to define a cavity 1520. A hardening material can be injected into an aperture 1512 in the retaining device 1510. Suitable materials include, but not limited to, a polymer or a crystal free metal. Additionally, as will be appreciated by those of skill in the art, the material injected can be initially in powder form with a liquid catalyst or hardening material injected thereafter.

As illustrated in FIG. 14G, the surface of the bone 1550 can be prepared, e.g. by curette or drill, so that the surface of the bone 1550 defines small teeth, holes, or anchoring members, 1552 that help anchor the resulting device to the articular surface 1550. As shown in FIGS. 14G(2) and (5) the drill holes can be drilled parallel in relation to one another, where there are more than two, and perpendicular to the surface of the subchondral bone 1552. Alternatively, the drill holes can be drilled at an angle in relationship to each other and at a angle that is not perpendicular to the subchondral bone 1553 as illustrated in FIG. 15G(3-4). As will be appreciated by those of skill in the art, one or more pegs can be created on the surface of the bone. For example FIG. 14G(2) illustrates a two peg set-up while FIG. 14G(8) illustrates a single peg scenario and FIG. 14G(4) illustrates a four peg scenario where some pegs are in parallel relationship while others are not. As shown in FIG. 14G(9), the aperture (1552 or 1553) can be formed so that the bore does not form a cylinder, but rather has channel protrusions 1572 into the bone that, when filled, form the turning channel for a screw, thus resulting in the filled aperture forming a screw that enables the anchored device to be removed by turning in a clockwise or counter-clockwise direction.

Figure 14H:
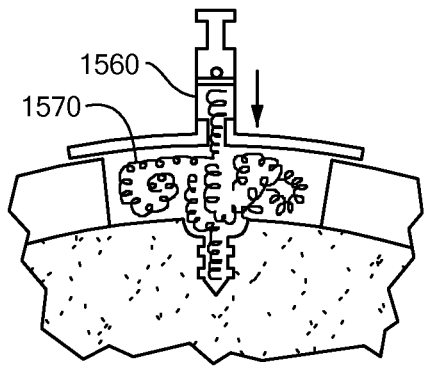
Figure 14H:
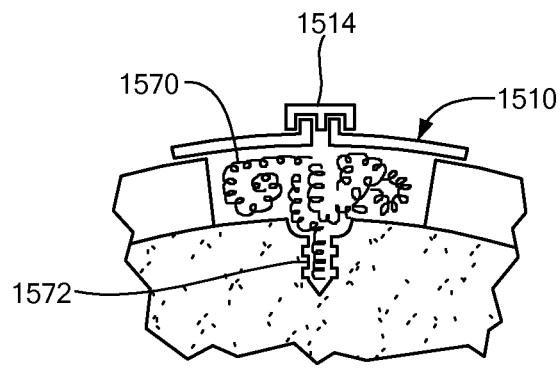
Figure 14H:
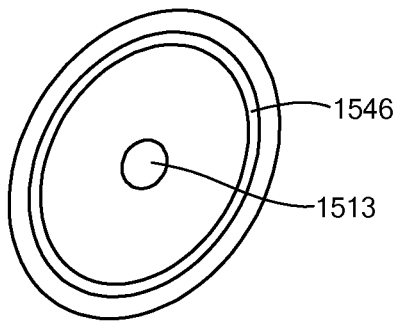

As shown in FIG. 14H, a ridge 1546, typically circumferential, can be used. The circumferential ridge can help achieve a tight seal between the detaining device and the cartilage in order to avoid spillage of the injected material in the joint cavity. Alternatively, the periphery of the mold can include a soft, compressible material that helps achieve a tight seal between the mold and the surrounding cartilage.

Figure 14I:
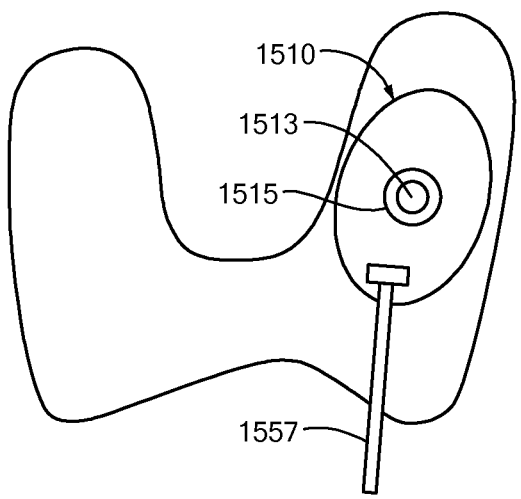

FIG. 14I illustrates the retaining mold with a handle placed on the surface of a bone.

Figure 14J:
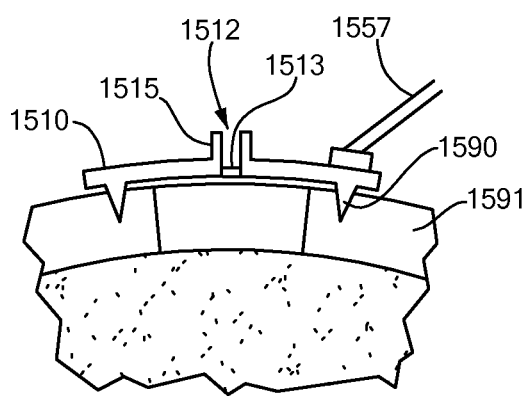

As shown in FIG. 14J, the retaining device 1510 can have one or more handles 1547 attached to it. The handle can facilitate the surgeon maintaining the retaining device in position while the injected material hardens. The aperture 1512 of the retaining device accepts injections and can include a membrane 1513 as shown in FIG. 14J. The configuration assists in creating a tight seal after a needle 1560 or injection instrument used to inject the material 1570 into the cavity 1520 is removed. Additionally, or inplace of the membrane 1513, a cap 1514 can be provided that seals the aperture 1512 after the material 1570 is injected. Additionally, anchoring teeth 1590 can be provided that communicate with the meniscus 1591 or cartilage surrounding a defect. The anchoring teeth 1590 help keep the device stable when placed over the defect.

As illustrated in FIG. 14G(4) more than one aperture 1512, 1512' can be provided without departing from the scope of the invention.

The retaining device system can be designed to inject an area equal to or slightly greater than the area of diseased cartilage. Alternatively, the retaining device system can be designed for the entire weight-bearing surface or the entire articular surface of a compartment. Retaining devices can be used on opposing articular surfaces, e.g. on a femoral condyle and a tibial plateau, thereby recreating a smooth gliding surface on both articular surfaces.

The retaining device can be designed to allow for light exposure including UV light. For example, the retaining device can be made using a transparent plastic. The retaining device can also be made to allow for passage of ultrasound waves.

C. Customized Containers

In another embodiment of the invention, a container or well can be formed to the selected specifications, for example to match the material needed for a particular subject or to create a stock of repair materials in a variety of sizes. The size and shape of the container can be designed using the thickness and curvature information obtained from the joint and from the cartilage defect. More specifically, the inside of the container can be shaped to follow any selected measurements, for example as obtained from the cartilage defect(s) of a particular subject. The container can be filled with a cartilage replacement or regenerating material, for example, collagen-containing materials, plastics, bioresorbable materials and/or any suitable tissue scaffold. The cartilage regenerating or replacement material can also consist of a suspension of stem cells or fetal or immature or mature cartilage cells that subsequently develop to more mature cartilage inside the container. Further, development and/or differentiation can be enhanced with use of certain tissue nutrients and growth factors.

The material is allowed to harden and/or grow inside the container until the material has the desired traits, for example, thickness, elasticity, hardness, biochemical composition, etc. Molds can be generated using any suitable technique, for example computer devices and automation, e.g. computer assisted design (CAD) and, for example, computer assisted modeling (CAM). Because the resulting material generally follows the contour of the inside of the container it will better fit the defect itself and facilitate integration.

D. Designs Encompassing Multiple Component Repair Materials

The articular repair system or implants described herein can include one or more components.

Figure 15A:
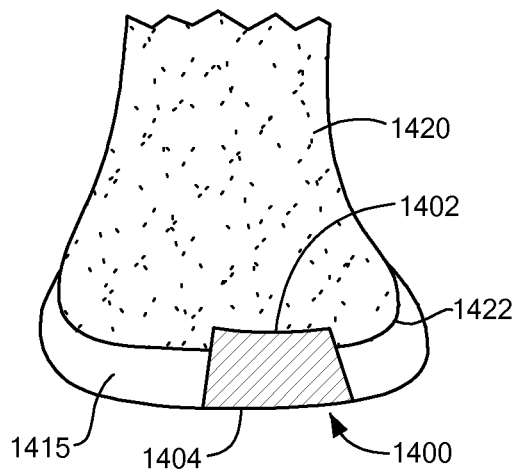
FIGS. 15A-B show single and multiple component devices.
Figure 15B:
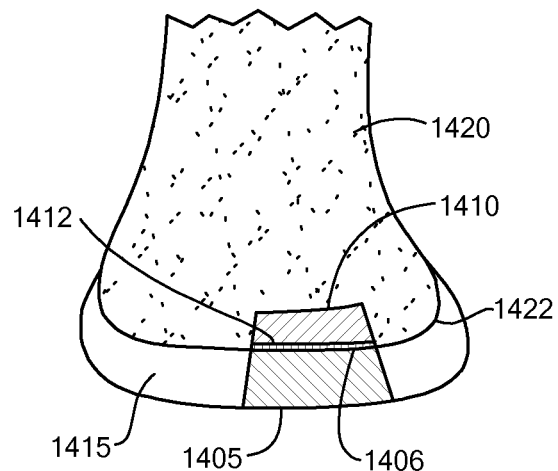

FIGS. 15A-B shows single and multiple component devices. FIG. 15A illustrates an example of a single component articular surface repair system 1400 with varying curvature and radii that fits within the subchondral bone 1420 such that the interior surface 1402 of the system 1400 does not form an extension of the surface of the subchondral bone 1422. The articular surface repair system is chosen to include convex 1402 and concave 1404 portions. Such devices can be preferable in a lateral femoral condyle or small joints such as the elbow joint. FIG. 15B depicts a multi-component articular surface repair system with a second component 1410 with a surface 1412 that forms an extension of the surface 1422 of the subchondral bone 1420 and a first component 1405 with an interior surface 1406 that forms an extension of the curvature and shape of the surrounding normal cartilage 1415. The second component 1410 and the first component 1405 demonstrate varying curvatures and radii with convex and concave portions that correspond to the curvature of the subchondral bone 1420 and/or the normal cartilage 1415. As will be appreciated by those of skill in the art, these two components can be formed such that the parts are integrally formed with each other, or can be formed such that each part abuts the other. Additionally, the relationship between the parts can be by any suitable mechanism including adhesives and mechanical means.

Figure 16A:
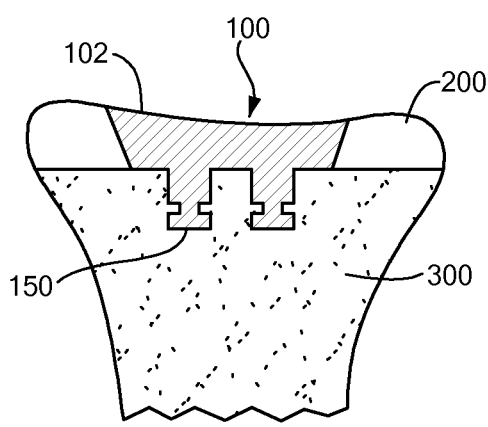
FIGS. 16A-B show exemplary articular repair systems having an outer contour matching the surrounding normal cartilage. The systems are implanted into the underlying bone using one or more pegs.
Figure 16B:
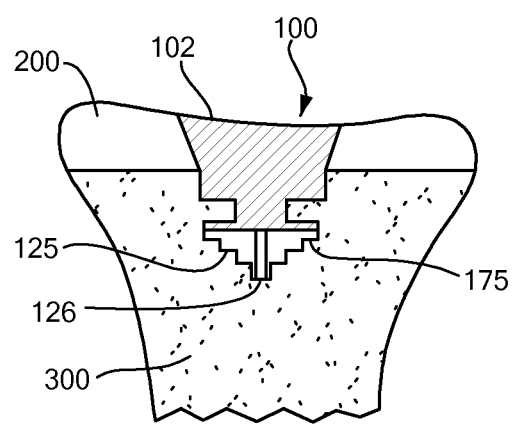

FIGS. 16A-B show articular repair systems 100 having an outer contour 102 forming an extension of the surrounding normal cartilage 200. The systems are implanted into the underlying bone 300 using one or more pegs 150, 175. The pegs, pins, or screws can be porous-coated and can have flanges 125 as shown in FIG. 15B.

Figure 17:
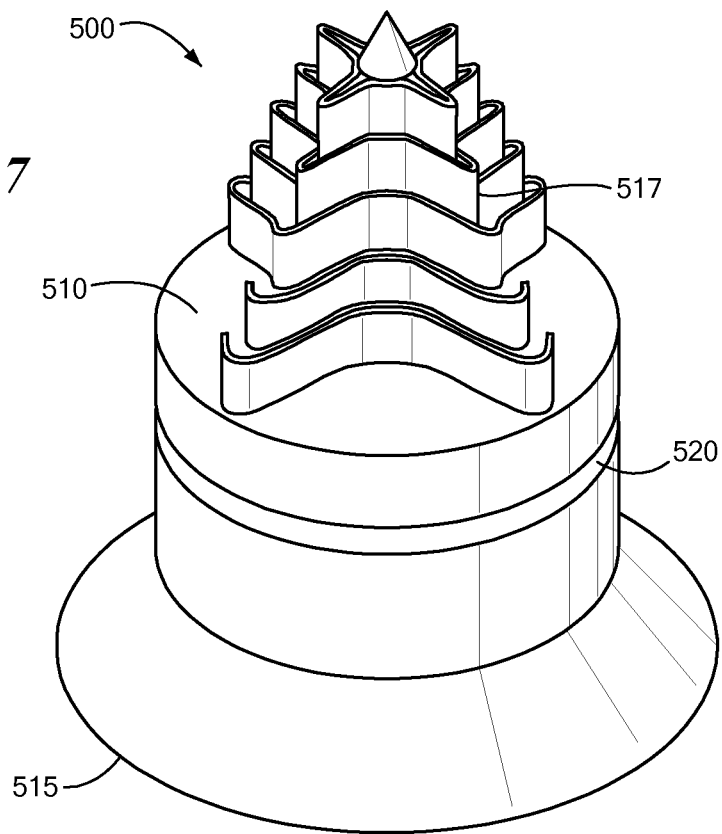
FIG. 17 shows a perspective view of an exemplary articular repair device including a flat surface to control depth and prevent toggle; an exterior surface having the contour of normal cartilage; flanges to prevent rotation and control toggle; a groove to facilitate tissue in-growth.

FIG. 17 shows an exemplary articular repair device 500 including a flat surface 510 to control depth and prevent toggle; an exterior surface 515 having the contour of normal cartilage; flanges 517 to prevent rotation and control toggle; a groove 520 to facilitate tissue in-growth.

Figure 18A:
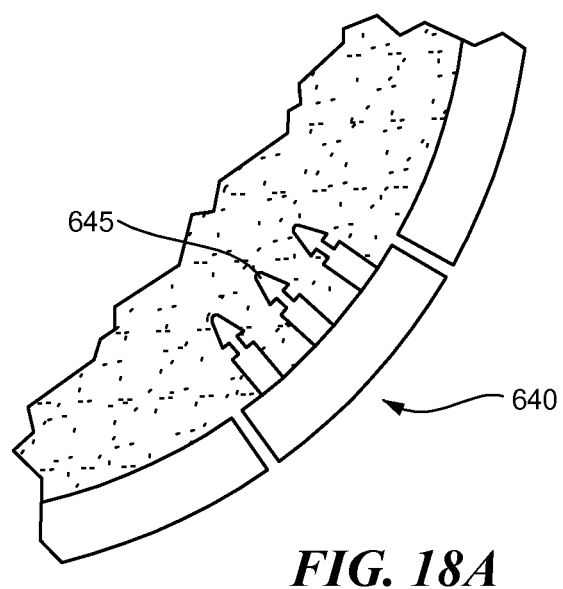
FIGS. 18A-D depict, in cross-section, another example of an implant with multiple anchoring pegs.
Figure 18B:
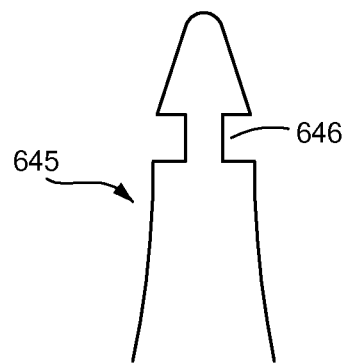
Figure 18C:
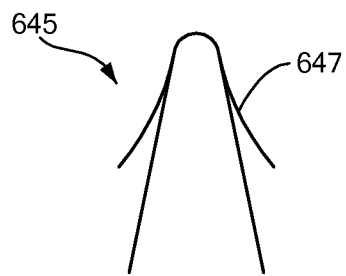
Figure 18D:
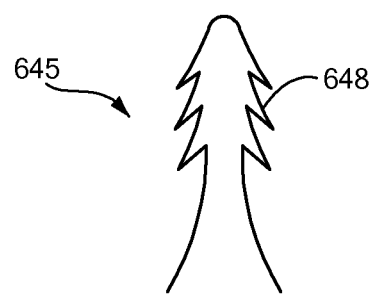

FIGS. 18A-D depict, in cross-section, another example of an implant 640 with multiple anchoring pegs, stems, or screws 645. FIG. 18B-D show various cross-sectional representations of various possible embodiments of the pegs, or anchoring stems. FIG. 18B shows a peg 645 having a notch 646 or groove around its circumference; FIG. 18C shows a peg 645 with radially-extending arms 647 that help anchor the device in the underlying bone; and FIG. 18D shows a peg 645 with multiple grooves or flanges 648.

Figure 19A:
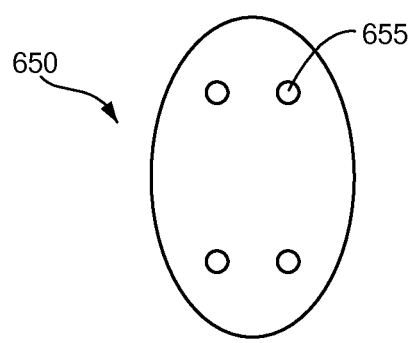
FIG. 19A-B depict an overhead view of an exemplary implant with multiple anchoring pegs and depict how the pegs are not necessarily linearly aligned along the longitudinal axis of the device.
Figure 19B:
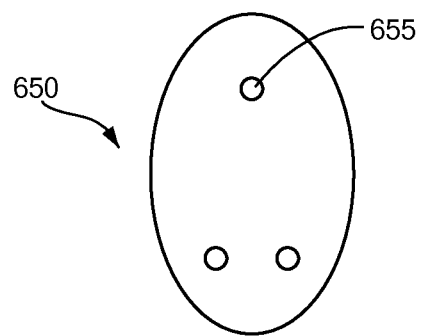

FIGS. 19A-B depict an overhead view of an exemplary implant 650 with multiple anchoring pegs 655 which illustrates that the pegs are not necessarily linearly aligned along the longitudinal axis of the device.

Figure 20A:
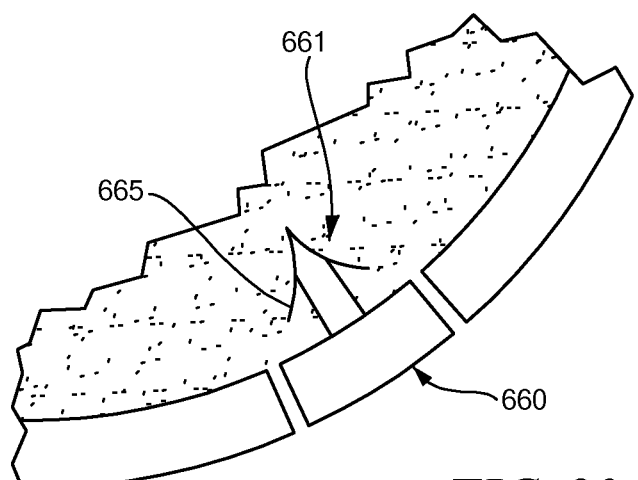
FIGS. 20A-E depict an exemplary implant having radially extending arms.
Figure 20B:
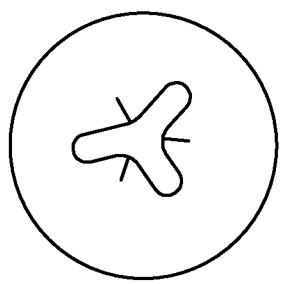
Figure 20C:
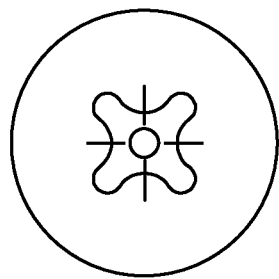
Figure 20D:
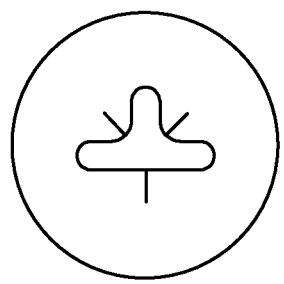
Figure 20E:
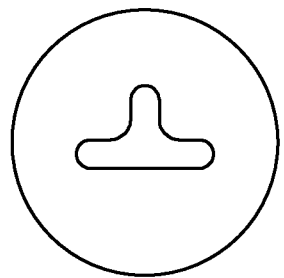

FIG. 20A depicts an implant 660 with a peg 661 having radially extending arms 665. FIGS. 20B-E are top views of the implant pegs illustrating a variety of suitable alternative shapes.

Examples of one-component systems include, but are not limited to, a plastic, a polymer, a metal, a metal alloy, crystal free metals, a biologic material or combinations thereof. In certain embodiments, the surface of the repair system facing the underlying bone can be smooth. In other embodiments, the surface of the repair system facing the underlying bone can be porous or porous-coated. In another aspect, the surface of the repair system facing the underlying bone is designed with one or more grooves, for example to facilitate the in-growth of the surrounding tissue. The external surface of the device can have a step-like design, which can be advantageous for altering biomechanical stresses. Optionally, flanges can also be added at one or more positions on the device (e.g., to prevent the repair system from rotating, to control toggle and/or prevent settling into the marrow cavity). The flanges can be part of a conical or a cylindrical design. A portion or all of the repair system facing the underlying bone can also be flat which can help to control depth of the implant and to prevent toggle.

Non-limiting examples of multiple-component systems include combinations of metal, plastic, metal alloys, crystal free metals, and one or more biological materials. One or more components of the articular surface repair system can be composed of a biologic material (e.g. a tissue scaffold with cells such as cartilage cells or stem cells alone or seeded within a substrate such as a bioresorable material or a tissue scaffold, allograft, autograft or combinations thereof) and/or a non-biological material (e.g., polyethylene or a chromium alloy such as chromium cobalt).

Thus, the repair system can include one or more areas of a single material or a combination of materials, for example, the articular surface repair system can have a first and a second component. The first component is typically designed to have size, thickness and curvature similar to that of the cartilage tissue lost while the second component is typically designed to have a curvature similar to the subchondral bone. In addition, the first component can have biomechanical properties similar to articular cartilage, including but not limited to similar elasticity and resistance to axial loading or shear forces. The first and the second component can consist of two different metals or metal alloys. One or more components of the system (e.g., the second portion) can be composed of a biologic material including, but not limited to bone, or a non-biologic material including, but not limited to hydroxyapatite, tantalum, a chromium alloy, chromium cobalt or other metal alloys.

One or more regions of the articular surface repair system (e.g., the outer margin of the first portion and/or the second portion) can be bioresorbable, for example to allow the interface between the articular surface repair system and the patient's normal cartilage, over time, to be filled in with hyaline or fibrocartilage. Similarly, one or more regions (e.g., the outer margin of the first portion of the articular surface repair system and/or the second portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

The repair system (e.g., the second component in multiple component systems) can be attached to the patient's bone with use of a cement-like material such as methylmethacrylate, injectable hydroxy- or calcium-apatite materials and the like.

In certain embodiments, one or more portions of the articular surface repair system can be pliable or liquid or deformable at the time of implantation and can harden later. Hardening can occur, for example, within 1 second to 2 hours (or any time period therebetween), preferably with in 1 second to 30 minutes (or any time period therebetween), more preferably between 1 second and 10 minutes (or any time period therebetween).

One or more components of the articular surface repair system can be adapted to receive injections. For example, the external surface of the articular surface repair system can have one or more openings therein. The openings can be sized to receive screws, tubing, needles or other devices which can be inserted and advanced to the desired depth, for example, through the articular surface repair system into the marrow space. Injectables such as methylmethacrylate and injectable hydroxy- or calcium-apatite materials can then be introduced through the opening (or tubing inserted therethrough) into the marrow space thereby bonding the articular surface repair system with the marrow space. Similarly, screws or pins, or other anchoring mechanisms. can be inserted into the openings and advanced to the underlying subchondral bone and the bone marrow or epiphysis to achieve fixation of the articular surface repair system to the bone. Portions or all components of the screw or pin can be bioresorbable, for example, the distal portion of a screw that protrudes into the marrow space can be bioresorbable. During the initial period after the surgery, the screw can provide the primary fixation of the articular surface repair system. Subsequently, ingrowth of bone into a porous coated area along the undersurface of the articular cartilage repair system can take over as the primary stabilizer of the articular surface repair system against the bone.

The articular surface repair system can be anchored to the patient's bone with use of a pin or screw or other attachment mechanism. The attachment mechanism can be bioresorbable. The screw or pin or attachment mechanism can be inserted and advanced towards the articular surface repair system from a non-cartilage covered portion of the bone or from a non-weight-bearing surface of the joint.

The interface between the articular surface repair system and the surrounding normal cartilage can be at an angle, for example oriented at an angle of 90 degrees relative to the underlying subchondral bone. Suitable angles can be determined in view of the teachings herein, and in certain cases, non-90 degree angles can have advantages with regard to load distribution along the interface between the articular surface repair system and the surrounding normal cartilage.

The interface between the articular surface repair system and the surrounding normal cartilage and/or bone can be covered with a pharmaceutical or bioactive agent, for example a material that stimulates the biological integration of the repair system into the normal cartilage and/or bone. The surface area of the interface can be irregular, for example, to increase exposure of the interface to pharmaceutical or bioactive agents.

E. Pre-Existing Repair Systems

As described herein, repair systems, including surgical instruments, guides and molds, of various sizes, curvatures and thicknesses can be obtained. These repair systems, including surgical instruments, guides and molds, can be catalogued and stored to create a library of systems from which an appropriate system for an individual patient can then be selected. In other words, a defect, or an articular surface, is assessed in a particular subject and a pre-existing repair system, including surgical instruments, guides and molds, having a suitable shape and size is selected from the library for further manipulation (e.g., shaping) and implantation.

F. Mini-Prosthesis

As noted above, the methods and compositions described herein can be used to replace only a portion of the articular surface, for example, an area of diseased cartilage or lost cartilage on the articular surface. In these systems, the articular surface repair system can be designed to replace only the area of diseased or lost cartilage or it can extend beyond the area of diseased or lost cartilage, e.g., 3 or 5 mm into normal adjacent cartilage. In certain embodiments, the prosthesis replaces less than about 70% to 80% (or any value therebetween) of the articular surface (e.g., any given articular surface such as a single femoral condyle, etc.), preferably, less than about 50% to 70% (or any value therebetween), more preferably, less than about 30% to 50% (or any value therebetween), more preferably less than about 20% to 30% (or any value therebetween), even more preferably less than about 20% of the articular surface.

The prosthesis can include multiple components, for example a component that is implanted into the bone (e.g., a metallic device) attached to a component that is shaped to cover the defect of the cartilage overlaying the bone. Additional components, for example intermediate plates, meniscal repair systems and the like can also be included. It is contemplated that each component replaces less than all of the corresponding articular surface.

However, each component need not replace the same portion of the articular surface. In other words, the prosthesis can have a bone-implanted component that replaces less than 30% of the bone and a cartilage component that replaces 60% of the cartilage. The prosthesis can include any combination, provided each component replaces less than the entire articular surface.

The articular surface repair system can be formed or selected so that it will achieve a near anatomic fit or match with the surrounding or adjacent cartilage. Typically, the articular surface repair system is formed and/or selected so that its outer margin located at the external surface will be aligned with the surrounding or adjacent cartilage.

Thus, the articular repair system can be designed to replace the weight-bearing portion (or more or less than the weight bearing portion) of an articular surface, for example in a femoral condyle. The weight-bearing surface refers to the contact area between two opposing articular surfaces during activities of normal daily living (e.g., normal gait). At least one or more weight-bearing portions can be replaced in this manner, e.g., on a femoral condyle and on a tibia.

In other embodiments, an area of diseased cartilage or cartilage loss can be identified in a weight-bearing area and only a portion of the weight-bearing area, specifically the portion containing the diseased cartilage or area of cartilage loss, can be replaced with an articular surface repair system.

In another embodiment, the articular repair system can be designed or selected to replace substantially all of the articular surface, e.g. a condyle.

In another embodiment, for example, in patients with diffuse cartilage loss, the articular repair system can be designed to replace an area slightly larger than the weight-bearing surface.

In certain aspects, the defect to be repaired is located only on one articular surface, typically the most diseased surface. For example, in a patient with severe cartilage loss in the medial femoral condyle but less severe disease in the tibia, the articular surface repair system can only be applied to the medial femoral condyle. Preferably, in any methods described herein, the articular surface repair system is designed to achieve an exact or a near anatomic fit with the adjacent normal cartilage.

In other embodiments, more than one articular surface can be repaired. The area(s) of repair will be typically limited to areas of diseased cartilage or cartilage loss or areas slightly greater than the area of diseased cartilage or cartilage loss within the weight-bearing surface(s).

The implant and/or the implant site can be sculpted to achieve a near anatomic alignment between the implant and the implant site. In another embodiment of the invention, an electronic image is used to measure the thickness, curvature, or shape of the articular cartilage or the subchondral bone, and/or the size of a defect, and an articular surface repair system is selected using this information. The articular surface repair system can be inserted arthroscopically. The articular surface repair system can have a single radius. More typically, however, as shown in FIG. 15A, discussed above, the articular surface repair system 1500 has varying curvatures and radii within the same plane, e.g. anteroposterior or mediolateral or superoinferior or oblique planes, or within multiple planes. In this manner, the articular surface repair system can be shaped to achieve a near anatomic alignment between the implant and the implant site. This design allows not only allows for different degrees of convexity or concavity, but also for concave portions within a predominantly convex shape or vice versa 1500.

In another embodiment the articular surface repair system has an anchoring stem, used to anchor the device, for example, as described in U.S. Pat. No. 6,224,632 to Pappas et al issued May 1, 2001. The stem, or peg, can have different shapes including conical, rectangular, fin among others. The mating bone cavity is typically similarly shaped as the corresponding stem.

As shown in FIG. 16, discussed above, the articular surface repair system 100 can be affixed to the subchondral bone 300, with one or more stems, or pegs, 150 extending through the subchondral plate into the marrow space. In certain instances, this design can reduce the likelihood that the implant will settle deeper into the joint over time by resting portions of the implant against the subchondral bone. The stems, or pegs, can be of any shape suitable to perform the function of anchoring the device to the bone. For example, the pegs can be cylindrical or conical. Optionally, the stems, or pegs, can further include notches or openings to allow bone in-growth. In addition, the stems can be porous coated for bone in-growth. The anchoring stems or pegs can be affixed to the bone using bone cement. An additional anchoring device can also be affixed to the stem or peg. The anchoring device can have an umbrella shape (e.g., radially expanding elements) with the wider portion pointing towards the subchondral bone and away from the peg. The anchoring device can be advantageous for providing immediate fixation of the implant. The undersurface of the articular repair system facing the subchondral bone can be textured or rough thereby increasing the contact surface between the articular repair system and the subchondral bone. Alternatively, the undersurface of the articular repair system can be porous coated thereby allowing in-growth. The surgeon can support the in-growth of bone by treating the subchondral bone with a rasp, typically to create a larger surface area and/or until bleeding from the subchondral bone occurs.

In another embodiment, the articular surface repair system can be attached to the underlying bone or bone marrow using bone cement. Bone cement is typically made from an acrylic polymeric material. Typically, the bone cement is comprised of two components: a dry powder component and a liquid component, which are subsequently mixed together. The dry component generally includes an acrylic polymer, such as polymethylmethacrylate (PMMA). The dry component can also contain a polymerization initiator such as benzoylperoxide, which initiates the free-radical polymerization process that occurs when the bone cement is formed. The liquid component, on the other hand, generally contains a liquid monomer such as methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer. When the liquid component is mixed with the dry component, the dry component begins to dissolve or swell in the liquid monomer. The amine accelerator reacts with the initiator to form free radicals that begin to link monomer units to form polymer chains. In the next two to four minutes, the polymerization process proceeds changing the viscosity of the mixture from a syrup-like consistency (low viscosity) into a dough-like consistency (high viscosity). Ultimately, further polymerization and curing occur, causing the cement to harden and affix a prosthesis to a bone.

In certain aspects of the invention, as shown in FIG. 7E, above, bone cement 755 or another liquid attachment material such as injectable calciumhydroxyapatite can be injected into the marrow cavity through one or more openings 750 in the prosthesis. These openings in the prosthesis can extend from the articular surface to the undersurface of the prosthesis 760. After injection, the openings can be closed with a polymer, silicon, metal, metal alloy or bioresorbable plug.

In another embodiment, one or more components of the articular surface repair (e.g., the surface of the system that is pointing towards the underlying bone or bone marrow) can be porous or porous coated. A variety of different porous metal coatings have been proposed for enhancing fixation of a metallic prosthesis by bone tissue in-growth. Thus, for example, U.S. Pat. No. 3,855,638 to Pilliar issued Dec. 24, 2974, discloses a surgical prosthetic device, which can be used as a bone prosthesis, comprising a composite structure consisting of a solid metallic material substrate and a porous coating of the same solid metallic material adhered to and extending over at least a portion of the surface of the substrate. The porous coating consists of a plurality of small discrete particles of metallic material bonded together at their points of contact with each other to define a plurality of connected interstitial pores in the coating. The size and spacing of the particles, which can be distributed in a plurality of monolayers, can be such that the average interstitial pore size is not more than about 200 microns. Additionally, the pore size distribution can be substantially uniform from the substrate-coating interface to the surface of the coating. In another embodiment, the articular surface repair system can contain one or more polymeric materials that can be loaded with and release therapeutic agents including drugs or other pharmacological treatments that can be used for drug delivery. The polymeric materials can, for example, be placed inside areas of porous coating. The polymeric materials can be used to release therapeutic drugs, e.g. bone or cartilage growth stimulating drugs. This embodiment can be combined with other embodiments, wherein portions of the articular surface repair system can be bioresorbable. For example, the first layer of an articular surface repair system or portions of its first layer can be bioresorbable. As the first layer gets increasingly resorbed, local release of a cartilage growth-stimulating drug can facilitate in-growth of cartilage cells and matrix formation.

In any of the methods or compositions described herein, the articular surface repair system can be pre-manufactured with a range of sizes, curvatures and thicknesses. Alternatively, the articular surface repair system can be custom-made for an individual patient.

IV. Manufacturing

A. Shaping

In certain instances shaping of the repair material will be required before or after formation (e.g., growth to desired thickness), for example where the thickness of the required cartilage material is not uniform (e.g., where different sections of the cartilage replacement or regenerating material require different thicknesses).

The replacement material can be shaped by any suitable technique including, but not limited to, mechanical abrasion, laser abrasion or ablation, radiofrequency treatment, cryoablation, variations in exposure time and concentration of nutrients, enzymes or growth factors and any other means suitable for influencing or changing cartilage thickness. See, e.g., WO 00/15153 to Mansmann published Mar. 23, 2000; If enzymatic digestion is used, certain sections of the cartilage replacement or regenerating material can be exposed to higher doses of the enzyme or can be exposed longer as a means of achieving different thicknesses and curvatures of the cartilage replacement or regenerating material in different sections of said material.

The material can be shaped manually and/or automatically, for example using a device into which a pre-selected thickness and/or curvature has been input and then programming the device using the input information to achieve the desired shape.

In addition to, or instead of, shaping the cartilage repair material, the site of implantation (e.g., bone surface, any cartilage material remaining, etc.) can also be shaped by any suitable technique in order to enhance integration of the repair material.

B. Sizing

The articular repair system can be formed or selected so that it will achieve a near anatomic fit or match with the surrounding or adjacent cartilage or subchondral bone or menisci and other tissue. The shape of the repair system can be based on the analysis of an electronic image (e.g. MRI, CT, digital tomosynthesis, optical coherence tomography or the like). If the articular repair system is intended to replace an area of diseased cartilage or lost cartilage, the near anatomic fit can be achieved using a method that provides a virtual reconstruction of the shape of healthy cartilage in an electronic image.

In one embodiment of the invention, a near normal cartilage surface at the position of the cartilage defect can be reconstructed by interpolating the healthy cartilage surface across the cartilage defect or area of diseased cartilage. This can, for example, be achieved by describing the healthy cartilage by means of a parametric surface (e.g. a B-spline surface), for which the control points are placed such that the parametric surface follows the contour of the healthy cartilage and bridges the cartilage defect or area of diseased cartilage. The continuity properties of the parametric surface will provide a smooth integration of the part that bridges the cartilage defect or area of diseased cartilage with the contour of the surrounding healthy cartilage. The part of the parametric surface over the area of the cartilage defect or area of diseased cartilage can be used to determine the shape or part of the shape of the articular repair system to match with the surrounding cartilage.

In another embodiment, a near normal cartilage surface at the position of the cartilage defect or area of diseased cartilage can be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in the cartilage appear as indentations that can be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the cartilage defect or area of diseased cartilage creates a new surface over the area of the cartilage defect or area of diseased cartilage that can be used to determine the shape or part of the shape of the articular repair system to match with the surrounding cartilage or subchondral bone.

As described above, the articular repair system, including surgical tools and instruments, molds, in situ repair systems, etc. can be formed or selected from a library or database of systems of various sizes, curvatures and thicknesses so that it will achieve a near anatomic fit or match with the surrounding or adjacent cartilage and/or subchondral bone. These systems can be pre-made or made to order for an individual patient. In order to control the fit or match of the articular repair system with the surrounding or adjacent cartilage or subchondral bone or menisci and other tissues preoperatively, a software program can be used that projects the articular repair system over the anatomic position where it will be implanted. Suitable software is commercially available and/or readily modified or designed by a skilled programmer.

In yet another embodiment, the articular surface repair system can be projected over the implantation site using one or more 3-D images. The cartilage and/or subchondral bone and other anatomic structures are extracted from a 3-D electronic image such as an MRI or a CT using manual, semi-automated and/or automated segmentation techniques. A 3-D representation of the cartilage and/or subchondral bone and other anatomic structures as well as the articular repair system is generated, for example using a polygon or NURBS surface or other parametric surface representation. For a description of various parametric surface representations see, for example Foley, J. D. et al., Computer Graphics: Principles and Practice in C; Addison-Wesley, $2^{nd}$ edition, 1995).

The 3-D representations of the cartilage and/or subchondral bone and other anatomic structures and the articular repair system can be merged into a common coordinate system. The articular repair system, including surgical tools and instruments, molds, in situ repair systems, etc. can then be placed at the desired implantation site. The representations of the cartilage, subchondral bone, menisci and other anatomic structures and the articular repair system are rendered into a 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards or www.3diabs.com for 3Dlabs products, or as part of the system software for Unix workstations) or DirectX® (multimedia API for Microsoft Windows® based PC systems; available from www.microsoft.com). The 3-D image can be rendered showing the cartilage, subchondral bone, menisci or other anatomic objects, and the articular repair system from varying angles, e.g. by rotating or moving them interactively or non-interactively, in real-time or non-real-time.

The software can be designed so that the articular repair system, including surgical tools and instruments, molds, in situ repair systems, etc. with the best fit relative to the cartilage and/or subchondral bone is automatically selected, for example using some of the techniques described above. Alternatively, the operator can select an articular repair system, including surgical tools and instruments, molds, in situ repair systems, etc. and project it or drag it onto the implantation site using suitable tools and techniques. The operator can move and rotate the articular repair systems in three dimensions relative to the implantation site and can perform a visual inspection of the fit between the articular repair system and the implantation site. The visual inspection can be computer assisted. The procedure can be repeated until a satisfactory fit has been achieved. The procedure can be performed manually by the operator; or it can be computer-assisted in whole or in part. For example, the software can select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can then select another implant and test its alignment. One of skill in the art will readily be able to select, modify and/or create suitable computer programs for the purposes described herein.

In another embodiment, the implantation site can be visualized using one or more cross-sectional 2-D images. Typically, a series of 2-D cross-sectional images will be used. The 2-D images can be generated with imaging tests such as CT, MRI, digital tomosynthesis, ultrasound, or optical coherence tomography using methods and tools known to those of skill in the art. The articular repair system, including surgical tools and instruments, molds, in situ repair systems, etc. can then be superimposed onto one or more of these 2-D images. The 2-D cross-sectional images can be reconstructed in other planes, e.g. from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2-D images in any desired orientation in real time or near real time; the operator can rotate the imaged tissue volume while doing this. The articular repair system, including surgical tools and instruments, molds, in situ repair systems, etc. can be displayed in cross-section utilizing different display planes, e.g. sagittal, coronal or axial, typically matching those of the 2-D images demonstrating the cartilage, subchondral bone, menisci or other tissue. Alternatively, a three-dimensional display can be used for the articular repair system. The 2-D electronic image and the 2-D or 3-D representation of the articular repair system, including surgical tools and instruments, molds, in situ repair systems, etc. can be merged into a common coordinate system. The articular repair system can then be placed at the desired implantation site. The series of 2-D cross-sections of the anatomic structures, the implantation site and the articular repair system can be displayed interactively (e.g. the operator can scroll through a series of slices) or non-interactively (e.g. as an animation that moves through the series of slices), in real-time or non-real-time.

The software can be designed so that the articular repair system, including surgical tools and instruments, molds, in situ repair systems, etc. with the best fit relative to the cartilage and/or subchondral bone is automatically selected, for example using one or more of the techniques described above. Alternatively, the operator can select an articular repair system, including surgical tools and instruments, molds, in situ repair systems, etc. and project it or drag it onto the implantation site displayed on the cross-sectional 2-D images. The operator can then move and rotate the articular repair system relative to the implantation site and scroll through a cross-sectional 2-D display of the articular repair system and of the anatomic structures. The operator can perform a visual and/or computer-assisted inspection of the fit between the articular repair system and the implantation site. The procedure can be repeated until a satisfactory fit has been achieved. The procedure can be entirely manual by the operator; it can, however, also be computer-assisted. For example, the software can select a first trial implant that the operator can test (e.g., evaluate the fit). Software that highlights areas of poor alignment between the implant and the surrounding cartilage or subchondral bone or menisci or other tissues can also be designed and used. Based on this information, the software or the operator can select another implant and test its alignment.

C. Rapid Prototyping

Rapid protyping is a technique for fabricating a three-dimensional object from a computer model of the object. A special printer is used to fabricate the prototype from a plurality of two-dimensional layers. Computer software sections the representations of the object into a plurality of distinct two-dimensional layers and then a three-dimensional printer fabricates a layer of material for each layer sectioned by the software. Together the various fabricated layers form the desired prototype. More information about rapid prototyping techniques is available in US Patent Publication No 2002/0079601A1 to Russell et al., published Jun. 27, 2002. An advantage to using rapid prototyping is that it enables the use of free form fabrication techniques that use toxic or potent compounds safely. These compounds can be safely incorporated in an excipient envelope, which reduces worker exposure A powder piston and build bed are provided. Powder includes any material (metal, plastic, etc.) that can be made into a powder or bonded with a liquid. The power is rolled from a feeder source with a spreader onto a surface of a bed. The thickness of the layer is controlled by the computer. The print head then deposits a binder fluid onto the powder layer at a location where it is desired that the powder bind. Powder is again rolled into the build bed and the process is repeated, with the binding fluid deposition being controlled at each layer to correspond to the three-dimensional location of the device formation. For a further discussion of this process see, for example, US Patent Publication No 2003/017365A1 to Monkhouse et al. published Sep. 18, 2003.

The rapid prototyping can use the two dimensional images obtained, as described above in Section I, to determine each of the two-dimensional shapes for each of the layers of the prototyping machine. In this scenario, each two dimensional image slice would correspond to a two dimensional prototype slide. Alternatively, the three-dimensional shape of the defect can be determined, as described above, and then broken down into two dimensional slices for the rapid prototyping process. The advantage of using the three-dimensional model is that the two-dimensional slices used for the rapid prototyping machine can be along the same plane as the two-dimensional images taken or along a different plane altogether.

Rapid prototyping can be combined or used in conjunction with casting techniques. For example, a shell or container with inner dimensions corresponding to an articular repair system including surgical instruments, molds, alignment guides or surgical guides, can be made using rapid prototyping. Plastic or wax-like materials are typically used for this purpose. The inside of the container can subsequently be coated, for example with a ceramic, for subsequent casting. Using this process, personalized casts can be generated.

Rapid prototyping can be used for producing articular repair systems including surgical tools, molds, alignment guides, cut guides etc. Rapid prototyping can be performed at a manufacturing facility. Alternatively, it may be performed in the operating room after an intraoperative measurement has been performed.

V. Implantation

Following one or more manipulations (e.g., shaping, growth, development, etc), the cartilage replacement or regenerating material can then be implanted into the area of the defect. Implantation can be performed with the cartilage replacement or regenerating material still attached to the base material or removed from the base material. Any suitable methods and devices can be used for implantation, for example, devices as described in U.S. Pat. No. 6,375,658 to Hangody et al. issued Apr. 23, 2002; U.S. Pat. No. 6,358,253 to Torrie et al. issued Mar. 19, 2002; U.S. Pat. No. 6,328,765 to Hardwick et al. issued Dec. 11, 2001; and International Publication WO 01/19254 to Cummings et al. published Mar. 22, 2001.

In selected cartilage defects, the implantation site can be prepared with a single cut across the articular surface, for example, as shown in FIG. 8. In this case, single 810 and multi-component 820 prostheses can be utilized.

A. The Joint Replacement Procedure i. Knee Joint

Performing a total knee arthroplasty is a complicated procedure. In replacing the knee with an artificial knee, it is important to get the anatomical and mechanical axes of the lower extremity aligned correctly to ensure optimal functioning of the implanted knee.

Figure 21A:
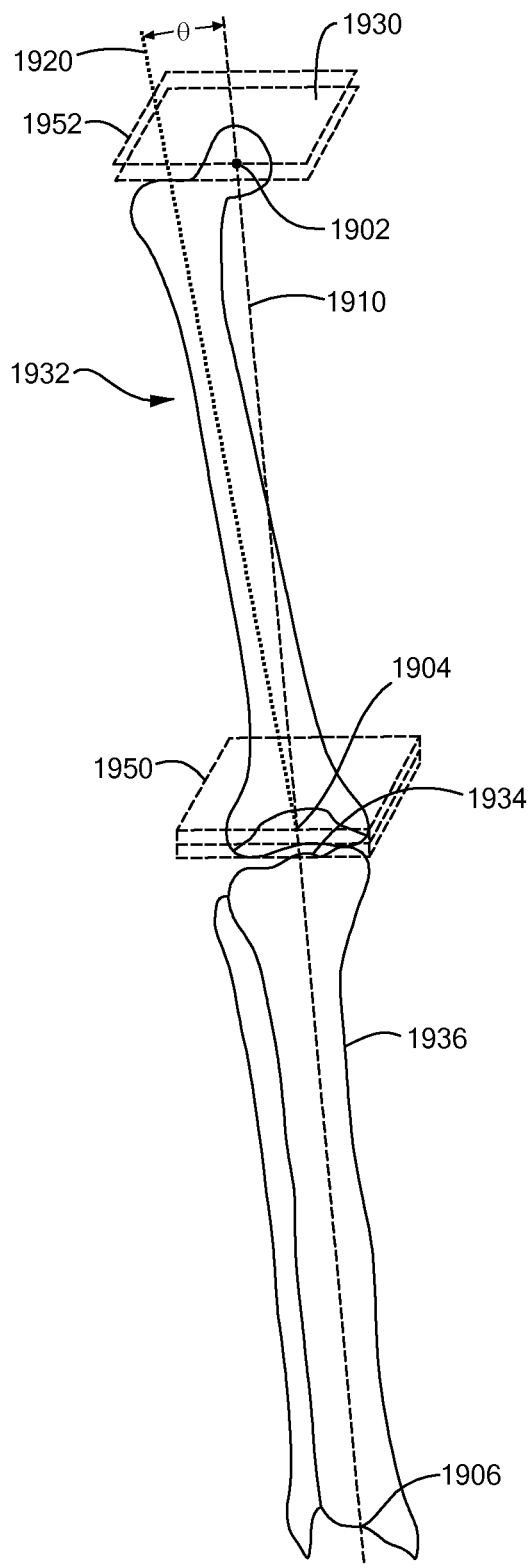
FIG. 21A illustrates a femur, tibia and fibula along with the mechanical and anatomic axes.

As shown in FIG. 21A, the center of the hip 1902 (located at the head 1930 of the femur 1932), the center of the knee 1904 (located at the notch where the intercondular tubercle 1934 of the tibia 1936 meet the femur) and ankle 1906 lie approximately in a straight line 1910 which defines the mechanical axis of the lower extremity. The anatomic axis 1920 aligns 5-7° offset θ from the mechanical axis in the valgus, or outward, direction.

The long axis of the tibia 1936 is collinear with the mechanical axis of the lower extremity 1910. From a three-dimensional perspective, the lower extremity of the body ideally functions within a single plane known as the median anterior-posterior plane (MAP-plane) throughout the flexion-extension arc. In order to accomplish this, the femoral head 1930, the mechanical axis of the femur, the patellar groove, the intercondylar notch, the patellar articular crest, the tibia and the ankle remain within the MAP-plane during the flexion-extension movement. During movement, the tibia rotates as the knee flexes and extends in the epicondylar axis which is perpendicular to the MAP-plane.

A variety of image slices can be taken at each individual joint, e.g., the knee joint 1950-1950$_n$, and the hip joint 1952-1950$_n$. These image slices can be used as described above in Section I along with an image of the full leg to ascertain the axis.

With disease and malfunction of the knee, alignment of the anatomic axis is altered. Performing a total knee arthroplasty is one solution for correcting a diseased knee. Implanting a total knee joint, such as the PFC Sigma RP Knee System by Johnson & Johnson, requires that a series of resections be made to the surfaces forming the knee joint in order to facilitate installation of the artificial knee. The resections should be made to enable the installed artificial knee to achieve flexion-extension movement within the MAP-plane and to optimize the patient's anatomical and mechanical axis of the lower extremity.

First, the tibia 1930 is resected to create a flat surface to accept the tibial component of the implant. In most cases, the tibial surface is resected perpendicular to the long axis of the tibia in the coronal plane, but is typically sloped 4-7° posteriorly in the sagittal plane to match the normal slope of the tibia. As will be appreciated by those of skill in the art, the sagittal slope can be 0° where the device to be implanted does not require a sloped tibial cut. The resection line 1958 is perpendicular to the mechanical axis 1910, but the angle between the resection line and the surface plane of the plateau 1960 varies depending on the amount of damage to the knee.

Figure 21B:
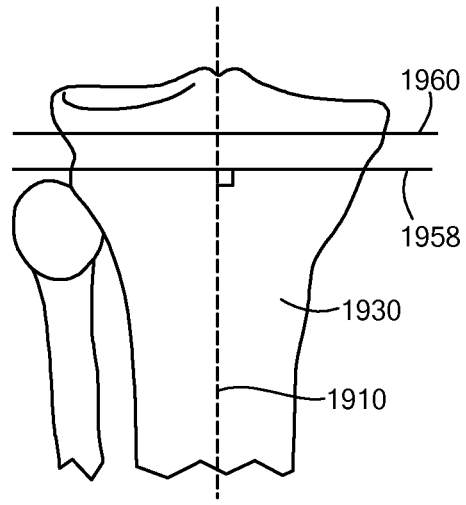
FIGS. 21B-E illustrate the tibia with the anatomic and mechanical axis used to create a cutting plane along with a cut femur and tibia.
Figure 21C:
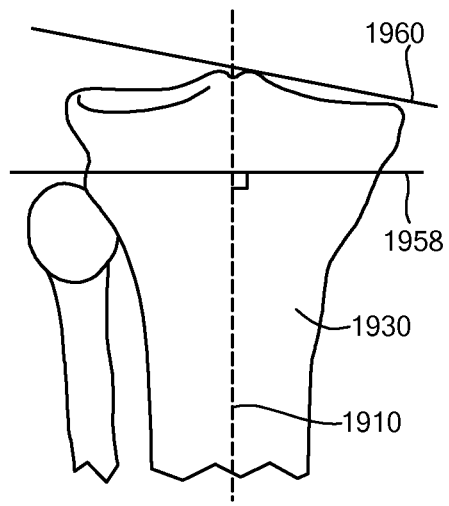
Figure 21D:
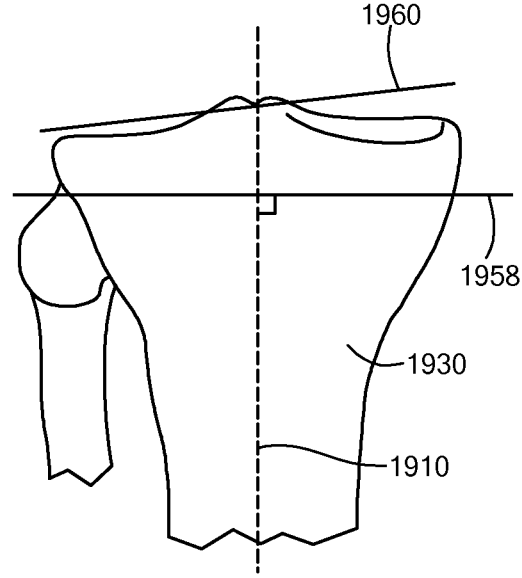

FIGS. 21B-D illustrate an anterior view of a resection of an anatomically normal tibial component, a tibial component in a varus knee, and a tibial component in a valgus knee, respectively. In each figure, the mechanical axis 1910 extends vertically through the bone and the resection line 1958 is perpendicular to the mechanical axis 1910 in the coronal plane, varying from the surface line formed by the joint depending on the amount of damage to the joint. FIG. 21B illustrates a normal knee wherein the line corresponding to the surface of the joint 1960 is parallel to the resection line 1958. FIG. 21C illustrates a varus knee wherein the line corresponding to the surface of the joint 1960 is not parallel to the resection line 1958. FIG. 21D illustrates a valgus knee wherein the line corresponding to the surface of the joint 1960 is not parallel to the resection line 1958.

Once the tibial surface has been prepared, the surgeon turns to preparing the femoral condyle.

The plateau of the femur 1970 is resected to provide flat surfaces that communicate with the interior of the femoral prosthesis. The cuts made to the femur are based on the overall height of the gap to be created between the tibia and the femur. Typically, a 20 mm gap is desirable to provide the implanted prosthesis adequate room to achieve full range of motion. The bone is resected at a 5-7° angle valgus to the mechanical axis of the femur. Resected surface 1972 forms a flat plane with an angular relationship to adjoining surfaces 1974, 1976. The angle θ', θ" between the surfaces 1972-1974, and 1972-1976 varies according to the design of the implant.

ii. Hip Joint

Figure 21E:
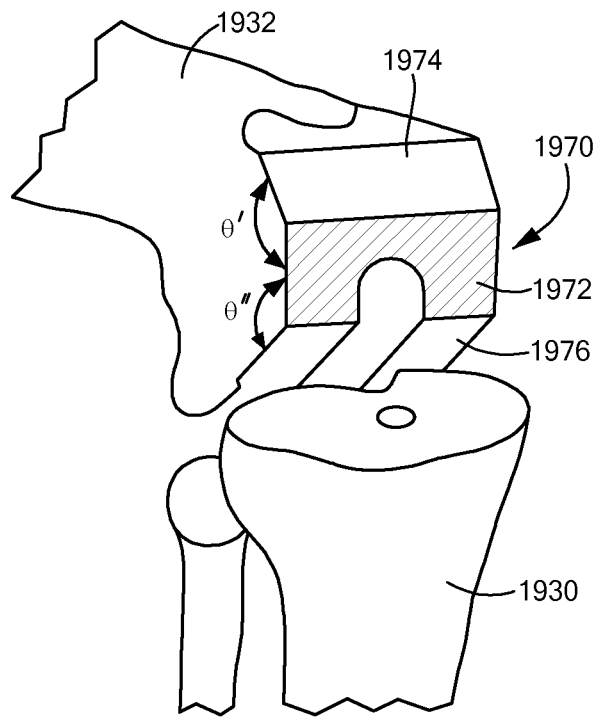
Figure 21F:
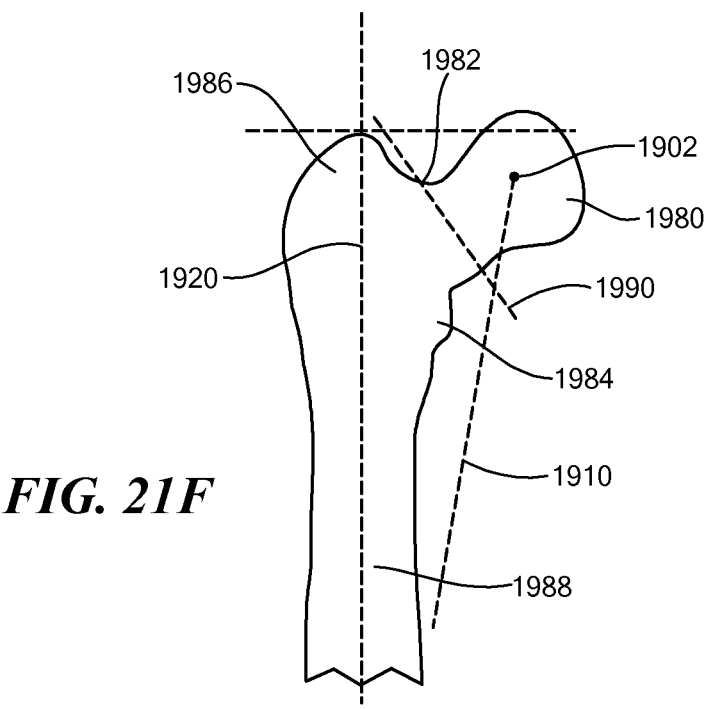
FIG. 21F illustrates the proximal end of the femur including the head of the femur.

As illustrated in FIG. 21F, the external geometry of the proximal femur includes the head 1980, the neck 1982, the lesser trochanter 1984, the greater trochanter 1986 and the proximal femoral diaphysis. The relative positions of the trochanters 1984, 1986, the femoral head center 1902 and the femoral shaft 1988 are correlated with the inclination of the neck-shaft angle. The mechanical axis 1910 and anatomic axis 1920 are also shown. Assessment of these relationships can change the reaming direction to achieve neutral alignment of the prosthesis with the femoral canal.

Using anteroposterior and lateral radiographs, measurements are made of the proximal and distal geometry to determine the size and optimal design of the implant.

Typically, after obtaining surgical access to the hip joint, the femoral neck 1982 is resected, e.g. along the line 1990. Once the neck is resected, the medullary canal is reamed.

Reaming can be accomplished, for example, with a conical or straight reamer, or a flexible reamer. The depth of reaming is dictated by the specific design of the implant. Once the canal has been reamed, the proximal reamer is prepared by serial rasping, with the rasp directed down into the canal.

B. Surgical Tools

Further, surgical assistance can be provided by using a device applied to the outer surface of the articular cartilage or the bone, including the subchondral bone, in order to match the alignment of the articular repair system and the recipient site or the joint. The device can be round, circular, oval, ellipsoid, curved or irregular in shape. The shape can be selected or adjusted to match or enclose an area of diseased cartilage or an area slightly larger than the area of diseased cartilage or substantially larger than the diseased cartilage. The area can encompass the entire articular surface or the weight bearing surface. Such devices are typically preferred when replacement of a majority or an entire articular surface is contemplated.

Mechanical devices can be used for surgical assistance (e.g., surgical tools), for example using gels, molds, plastics or metal. One or more electronic images or intraoperative measurements can be obtained providing object coordinates that define the articular and/or bone surface and shape. These objects' coordinates can be utilized to either shape the device, e.g. using a CAD/CAM technique, to be adapted to a patient's articular anatomy or, alternatively, to select a typically premade device that has a good fit with a patient's articular anatomy. The device can have a surface and shape that will match all or portions of the articular or bone surface and shape, e.g. similar to a "mirror image." The device can include apertures, slots and/or holes to accommodate surgical instruments such as drills, reamers, curettes, k-wires, screws and saws.

Typically, a position will be chosen that will result in an anatomically desirable cut plane, drill hole, or general instrument orientation for subsequent placement of an articular repair system or for facilitating placement of the articular repair system. Moreover, the device can be designed so that the depth of the drill, reamer or other surgical instrument can be controlled, e.g., the drill cannot go any deeper into the tissue than defined by the device, and the size of the hole in the block can be designed to essentially match the size of the implant. Information about other joints or axis and alignment information of a joint or extremity can be included when selecting the position of these slots or holes. Alternatively, the openings in the device can be made larger than needed to accommodate these instruments. The device can also be configured to conform to the articular shape. The apertures, or openings, provided can be wide enough to allow for varying the position or angle of the surgical instrument, e.g., reamers, saws, drills, curettes and other surgical instruments. An instrument guide, typically comprised of a relatively hard material, can then be applied to the device. The device helps orient the instrument guide relative to the three-dimensional anatomy of the joint.

The surgeon can, optionally, make fine adjustments between the alignment device and the instrument guide. In this manner, an optimal compromise can be found, for example, between biomechanical alignment and joint laxity or biomechanical alignment and joint function, e.g. in a knee joint flexion gap and extension gap. By oversizing the openings in the alignment guide, the surgeon can utilize the instruments and insert them in the instrument guide without damaging the alignment guide. Thus, in particular if the alignment guide is made of plastic, debris will not be introduced into the joint. The position and orientation between the alignment guide and the instrument guide can be also be optimized with the use of, for example, interposed spacers, wedges, screws and other mechanical or electrical methods known in the art.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more molds. The surgeon can intraoperatively evaluate the laxity or tightness of a joint using spacers with different thickness or one or more spacers with the same thickness. For example, spacers can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers for a given joint and mold. A surgical cut guide can be applied to the mold with the spacers optionally interposed between the mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the mold. Hinge-like mechanisms are applicable. Similarly, jack-like mechanisms are useful. In principal, any mechanical or electrical device useful for fine-tuning the position of the cut guide relative to the molds can be used.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more molds. The surgeon can intraoperatively evaluate the laxity or tightness of a joint using spacers with different thickness or one or more spacers with the same thickness. For example, spacers can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers for a given joint and mold. A surgical cut guide can be applied to the mold with the spacers optionally interposed between the mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the mold. Hinge-like mechanisms are applicable. Similarly, jack-like mechanisms are useful. In principal, any mechanical or electrical device useful for fine-tuning the position of the cut guide relative to the molds can be used.

The molds and any related instrumentation such as spacers or ratchets can be combined with a tensiometer to provide a better intraoperative assessment of the joint. The tensiometer can be utilized to further optimize the anatomic alignment and tightness of the joint and to improve post-operative function and outcomes. Optionally local contact pressures may be evaluated intraoperatively, for example using a sensor like the ones manufactured by Tekscan, South Boston, Mass.

The mold or alignment guide can be made of a plastic or polymer. In other embodiments, the mold or portions of the mold can be made of metal. Metal inserts may be applied to plastic components. For example, a plastic mold may have an opening to accept a reaming device or a saw. A metal insert may be used to provide a hard wall to accept the reamer or saw. Using this or similar designs can be useful to avoid the accumulation of plastic or other debris in the joint when the saw or other surgical instruments may get in contact with the mold.

The molds may not only be used for assisting the surgical technique and guiding the placement and direction of surgical instruments. In addition, the molds can be utilized for guiding the placement of the implant or implant components. For example, in the hip joint, tilting of the acetabular component is a frequent problem with total hip arthroplasty. A mold can be applied to the acetabular wall with an opening in the center large enough to accommodate the acetabular component that the surgeon intends to place. The mold can have receptacles or notches that match the shape of small extensions that can be part of the implant or that can be applied to the implant. For example, the implant can have small members or extensions applied to the twelve o'clock and six o'clock positions. See, for example, FIG. 29A-D, discussed below. By aligning these members with notches or receptacles in the mold, the surgeon can ensure that the implant is inserted without tilting or rotation. These notches or receptacles can also be helpful to hold the implant in place while bone cement is hardening in cemented designs.

One or more molds can be used during the surgery. For example, in the hip, a mold can be initially applied to the proximal femur that closely approximates the 3D anatomy prior to the resection of the femoral head. The mold can include an opening to accommodate a saw (see FIGS. 28-29). The opening is positioned to achieve an optimally placed surgical cut for subsequent reaming and placement of the prosthesis. A second mold can then be applied to the proximal femur after the surgical cut has been made. The second mold can be useful for guiding the direction of a reamer prior to placement of the prosthesis. As can be seen in this, as well as in other examples, molds can be made for joints prior to any surgical intervention. However, it is also possible to make molds that are designed to fit to a bone or portions of a joint after the surgeon has already performed selected surgical procedures, such as cutting, reaming, drilling, etc. The mold can account for the shape of the bone or the joint resulting from these procedures.

In certain embodiments, the surgical assistance device comprises an array of adjustable, closely spaced pins (e.g., plurality of individually moveable mechanical elements). One or more electronic images or intraoperative measurements can be obtained providing object coordinates that define the articular and/or bone surface and shape. These objects' coordinates can be entered or transferred into the device, for example manually or electronically, and the information can be used to create a surface and shape that will match all or portions of the articular and/or bone surface and shape by moving one or more of the elements, e.g. similar to an "image." The device can include slots and holes to accommodate surgical instruments such as drills, curettes, k-wires, screws and saws. The position of these slots and holes can be adjusted by moving one or more of the mechanical elements. Typically, a position will be chosen that will result in an anatomically desirable cut plane, reaming direction, or drill hole or instrument orientation for subsequent placement of an articular repair system or for facilitating the placement of an articular repair system. Information about other joints or axis and alignment information of a joint or extremity can be included when selecting the position of these slots or holes.

Figure 22:
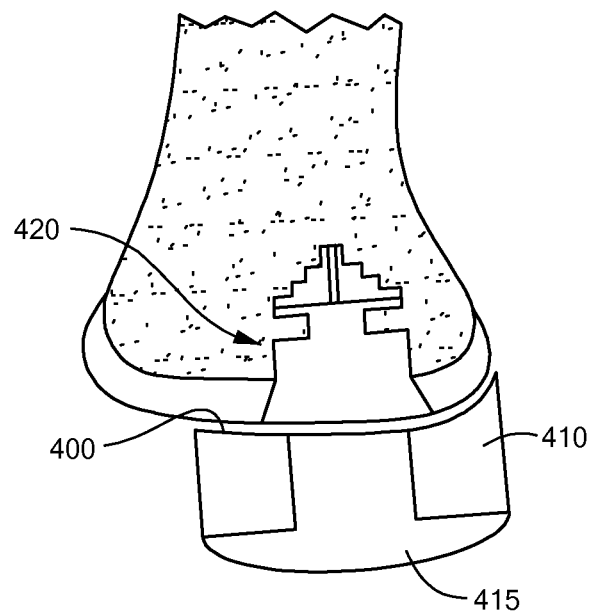
FIG. 22 shows an example of a surgical tool having one surface matching the geometry of an articular surface of the joint. Also shown is an aperture in the tool capable of controlling drill depth and width of the hole and allowing implantation of an insertion of implant having a press-fit design.

FIG. 22 shows an example of a surgical tool 410 having one surface 400 matching the geometry of an articular surface of the joint. Also shown is an aperture 415 in the tool 410 capable of controlling drill depth and width of the hole and allowing implantation or insertion of implant 420 having a press-fit design.

In another embodiment, a frame can be applied to the bone or the cartilage in areas other than the diseased bone or cartilage. The frame can include holders and guides for surgical instruments. The frame can be attached to one or preferably more previously defined anatomic reference points. Alternatively, the position of the frame can be cross-registered relative to one, or more, anatomic landmarks, using an imaging test or intraoperative measurement, for example one or more fluoroscopic images acquired intraoperatively. One or more electronic images or intraoperative measurements including using mechanical devices can be obtained providing object coordinates that define the articular and/or bone surface and shape. These objects' coordinates can be entered or transferred into the device, for example manually or electronically, and the information can be used to move one or more of the holders or guides for surgical instruments. Typically, a position will be chosen that will result in a surgically or anatomically desirable cut plane or drill hole orientation for subsequent placement of an articular repair system. Information about other joints or axis and alignment information of a joint or extremity can be included when selecting the position of these slots or holes.

Furthermore, re-useable tools (e.g., molds) can be also be created and employed. Non-limiting examples of re-useable materials include putties and other deformable materials (e.g., an array of adjustable closely spaced pins that can be configured to match the topography of a joint surface). In other embodiments, the molds may be made using balloons. The balloons can optionally be filled with a hardening material. A surface can be created or can be incorporated in the balloon that allows for placement of a surgical cut guide, reaming guide, drill guide or placement of other surgical tools. The balloon or other deformable material can be shaped intraoperatively to conform to at least one articular surface. Other surfaces can be shaped in order to be parallel or perpendicular to anatomic or biomechanical axes. The anatomic or biomechanical axes can be found using an intraoperative imaging test or surgical tools commonly used for this purpose in hip, knee or other arthroplasties.

In these embodiments, the mold can be created directly from the joint during surgery or, alternatively, created from an image of the joint, for example, using one or more computer programs to determine object coordinates defining the surface contour of the joint and transferring (e.g., dialing-in) these co-ordinates to the tool. Subsequently, the tool can be aligned accurately over the joint and, accordingly, the surgical instrument guide or the implant will be more accurately placed in or over the articular surface.

In both single-use and re-useable embodiments, the tool can be designed so that the instrument controls the depth and/or direction of the drill, i.e., the drill cannot go any deeper into the tissue than the instrument allows, and the size of the hole or aperture in the instrument can be designed to essentially match the size of the implant. The tool can be used for general prosthesis implantation, including, but not limited to, the articular repair implants described herein and for reaming the marrow in the case of a total arthroplasty.

These surgical tools (devices) can also be used to remove an area of diseased cartilage and underlying bone or an area slightly larger than the diseased cartilage and underlying bone. In addition, the device can be used on a "donor," e.g., a cadaveric specimen, to obtain implantable repair material. The device is typically positioned in the same general anatomic area in which the tissue was removed in the recipient. The shape of the device is then used to identify a donor site providing a seamless or near seamless match between the donor tissue sample and the recipient site. This can be achieved by identifying the position of the device in which the articular surface in the donor, e.g. a cadaveric specimen, has a seamless or near seamless contact with the inner surface when applied to the cartilage.

The device can be molded, machined or formed based on the size of the area of diseased cartilage and based on the curvature of the cartilage or the underlying subchondral bone or a combination of both. The molding can take into consideration surgical removal of, for example, the meniscus, in arriving at a joint surface configuration. The device can then be applied to the donor, (e.g., a cadaveric specimen) and the donor tissue can be obtained with use of a blade or saw or other tissue removing device. The device can then be applied to the recipient in the area of the diseased cartilage and the diseased cartilage and underlying bone can be removed with use of a blade or saw or other tissue cutting device whereby the size and shape of the removed tissue containing the diseased cartilage will closely resemble the size and shape of the donor tissue. The donor tissue can then be attached to the recipient site. For example, said attachment can be achieved with use of screws or pins (e.g., metallic, non-metallic or bioresorable) or other fixation means including but not limited to a tissue adhesive. Attachment can be through the cartilage surface or alternatively, through the marrow space.

The implant site can be prepared with use of a robotic device. The robotic device can use information from an electronic image for preparing the recipient site.

Identification and preparation of the implant site and insertion of the implant can be supported by asurgical navigation system. In such a system, the position or orientation of a surgical instrument with respect to the patient's anatomy can be tracked in real-time in one or more 2D or 3D images. These 2D or 3D images can be calculated from images that were acquired preoperatively, such as MR or CT images. Non-image based surgical navigation systems that find axes or anatomical structures, for example with use of joint motion, can also be used. The position and orientation of the surgical instrument as well as the mold including alignment guides, surgical instrument guides, reaming guides, drill guides, saw guides, etc. can be determined from markers attached to these devices. These markers can be located by a detector using, for example, optical, acoustical or electromagnetic signals.

Identification and preparation of the implant site and insertion of the implant can also be supported with use of a C-arm system. The C-arm system can afford imaging of the joint in one or, preferably, multiple planes. The multiplanar imaging capability can aid in defining the shape of an articular surface. This information can be used to selected an implant with a good fit to the articular surface. Currently available C-arm systems also afford cross-sectional imaging capability, for example for identification and preparation of the implant site and insertion of the implant. C-arm imaging can be combined with administration of radiographic contrast.

In still other embodiments, the surgical devices described herein can include one or more materials that harden to form a mold of the articular surface. A wide-variety of materials that harden in situ have been described above including polymers that can be triggered to undergo a phase change, for example polymers that are liquid or semi-liquid and harden to solids or gels upon exposure to air, application of ultraviolet light, visible light, exposure to blood, water or other ionic changes. (See, also, U.S. Pat. No. 6,443,988 to Felt et al. issued Sep. 3, 2002 and documents cited therein). Non-limiting examples of suitable curable and hardening materials include polyurethane materials (e.g., U.S. Pat. No. 6,443,988 to Felt et al., U.S. Pat. No. 5,288,797 to Khalil issued Feb. 22, 1994, U.S. Pat. No. 4,098,626 to Graham et al. issued Jul. 4, 1978 and U.S. Pat. No. 4,594,380 to Chapin et al. issued Jun. 10, 1986; and Lu et al. (2000) *BioMaterials* 21(15):1595-1605 describing porous poly(L-lactide acid foams); hydrophilic polymers as disclosed, for example, in U.S. Pat. No. 5,162,430; hydrogel materials such as those described in Wake et al. (1995) *Cell Transplantation* 4(3):275-279, Wiese et al. (2001) *J. Biomedical Materials Research* 54(2):179-188 and Marler et al. (2000) *Plastic Reconstruct. Surgery* 105(6): 2049-2058; hyaluronic acid materials (e.g., Duranti et al. (1998) *Dermatologic Surgery* 24(12):1317-1325); expanding beads such as chitin beads (e.g., Yusof et al. (2001) *J. Biomedical Materials Research* 54(1):59-68); crystal free metals such as Liquidmetals®, and/or materials used in dental applications (See, e.g., Brauer and Antonucci, "Dental Applications" pp. 257-258 in "Concise Encyclopedia of Polymer Science and Engineering" and U.S. Pat. No. 4,368,040 to Weissman issued Jan. 11, 1983). Any biocompatible material that is sufficiently flowable to permit it to be delivered to the joint and there undergo complete cure in situ under physiologically acceptable conditions can be used. The material can also be biodegradable.

The curable materials can be used in conjunction with a surgical tool as described herein. For example, the surgical tool can include one or more apertures therein adapted to receive injections and the curable materials can be injected through the apertures. Prior to solidifying in situ the materials will conform to the articular surface facing the surgical tool and, accordingly, will form a mirror image impression of the surface upon hardening, thereby recreating a normal or near normal articular surface. In addition, curable materials or surgical tools can also be used in conjunction with any of the imaging tests and analysis described herein, for example by molding these materials or surgical tools based on an image of a joint.

Figure 23:
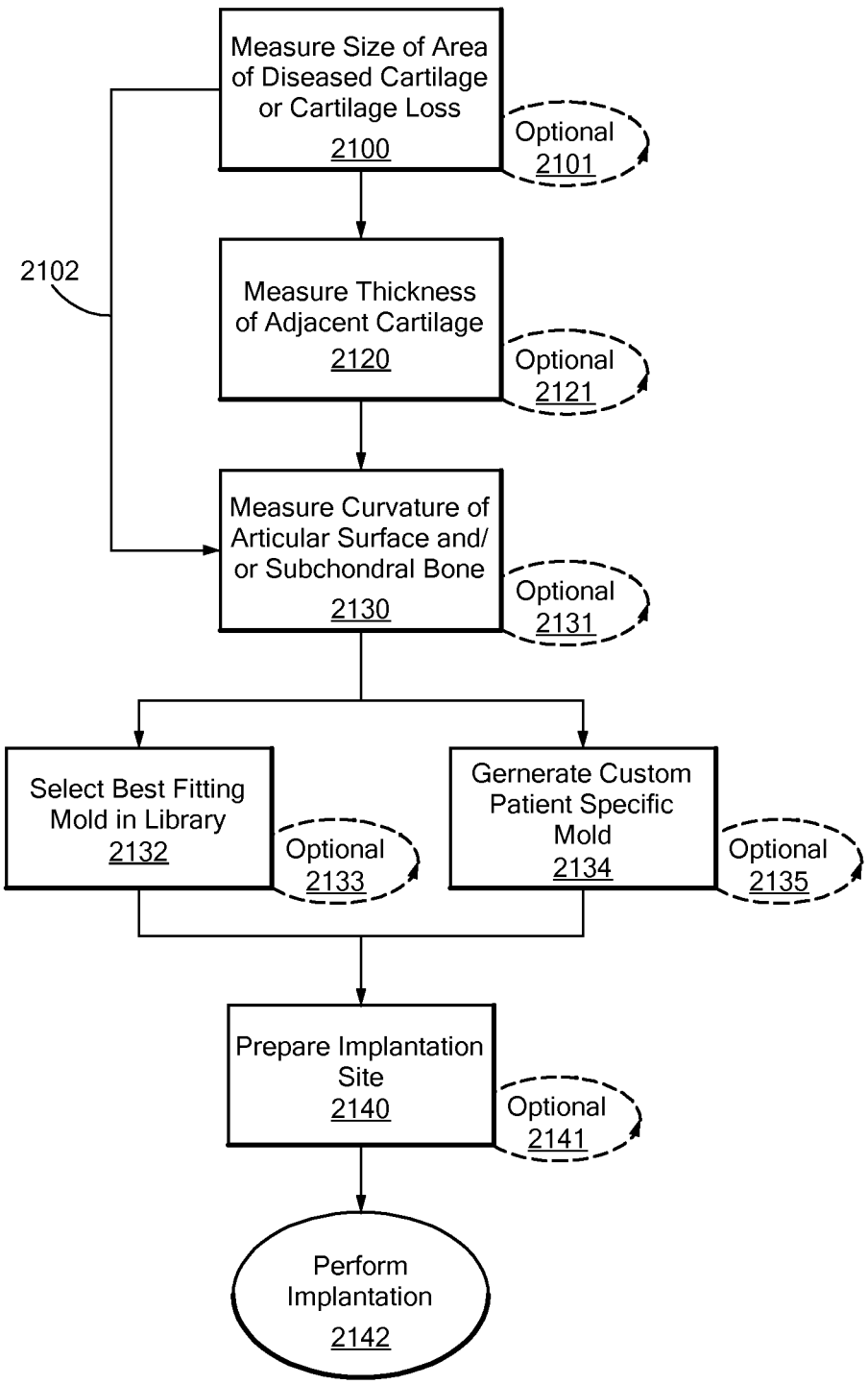
FIG. 23 is a flow chart depicting various methods of the invention used to create a mold for preparing a patient's joint for arthroscopic surgery.

FIG. 23 is a flow chart illustrating the steps involved in designing a mold for use in preparing a joint surface. Typically, the first step is to measure the size of the area of the diseased cartilage or cartilage loss 2100, Once the size of the cartilage loss has been measured, the user can measure the thickness of the adjacent cartilage 2120, prior to measuring the curvature of the articular surface and/or the subchondral bone 2130. Alternatively, the user can skip the step of measuring the thickness of the adjacent cartilage 2102. Once an understanding and determination of the nature of the cartilage defect is determined, either a mold can be selected from a library of molds 3132 or a patient specific mold can be generated 2134. In either event, the implantation site is then prepared 2140 and implantation is performed 2142. Any of these steps can be repeated by the optional repeat steps 2101, 2121, 2131, 2133, 2135, 2141.

A variety of techniques can be used to derive the shape of the mold. For example, a few selected CT slices through the hip joint, along with a full spiral CT through the knee joint and a few selected slices through the ankle joint can be used to help define the axes if surgery is contemplated of the knee joint. Once the axes are defined, the shape of the subchondral bone can be derived, followed by applying standardized cartilage loss. Other more sophisticated scanning procedures can be used to derive this information without departing from the scope of the invention.

Turning now to tools for specific joint applications which are intended to teach the concept of the design as it would then apply to other joints in the body:

i. Knee Joint

When a total knee arthroplasty is contemplated, the patient can undergo an imaging test, as discussed in more detail above, that will demonstrate the articular anatomy of a knee joint, e.g. width of the femoral condyles, the tibial plateau etc. Additionally, other joints can be included in the imaging test thereby yielding information on femoral and tibial axes, deformities such as varus and valgus and other articular alignment. The imaging test can be an x-ray image, preferably in standing, load-bearing position, a CT scan or an MRI scan or combinations thereof. The articular surface and shape as well as alignment information generated with the imaging test can be used to shape the surgical assistance device, to select the surgical assistance device from a library of different devices with pre-made shapes and sizes, or can be entered into the surgical assistance device and can be used to define the preferred location and orientation of saw guides or drill holes or guides for reaming devices or other surgical instruments. Intraoperatively, the surgical assistance device is applied to the tibial plateau and subsequently the femoral condyle(s) by matching its surface with the articular surface or by attaching it to anatomic reference points on the bone or cartilage. The surgeon can then introduce a reamer or saw through the guides and prepare the joint for the implantation. By cutting the cartilage and bone along anatomically defined planes, a more reproducible placement of the implant can be achieved. This can ultimately result in improved postoperative results by optimizing biomechanical stresses applied to the implant and surrounding bone for the patient's anatomy and by minimizing axis malalignment of the implant. In addition, the surgical assistance device can greatly reduce the number of surgical instruments needed for total or unicompartmental knee arthroplasty. Thus, the use of one or more surgical assistance devices can help make joint arthroplasty more accurate, improve postoperative results, improve long-term implant survival, reduce cost by reducing the number of surgical instruments used. Moreover, the use of one or more surgical assistance device can help lower the technical difficulty of the procedure and can help decrease operating room ("OR") times.

Thus, surgical tools described herein can also be designed and used to control drill alignment, depth and width, for example when preparing a site to receive an implant. For example, the tools described herein, which typically conform to the joint surface, can provide for improved drill alignment and more accurate placement of any implant. An anatomically correct tool can be constructed by a number of methods and can be made of any material, preferably a translucent material such as plastic, Lucite, silastic, SLA or the like, and typically is a block-like shape prior to molding.

Figure 24A:
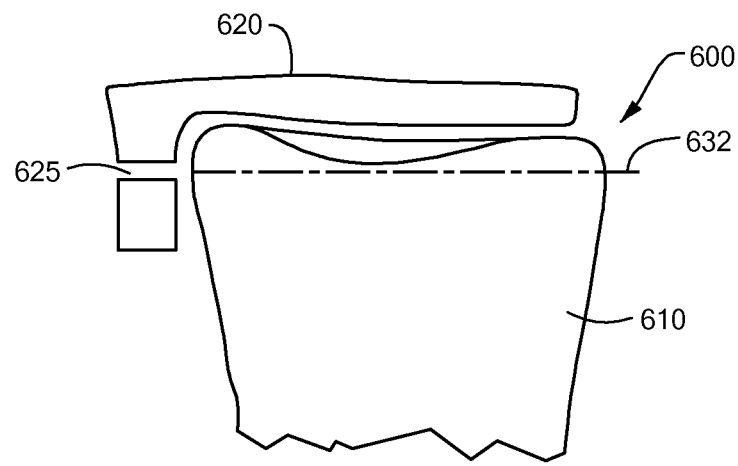
FIG. 24A depicts, in cross-section, an example of a surgical tool containing an aperture through which a surgical drill or saw can fit. The aperture guides the drill or saw to make the proper hole or cut in the underlying bone. Dotted lines represent where the cut corresponding to the aperture will be made in bone.

FIG. 24A depicts, in cross-section, an example of a mold 600 for use on the tibial surface having an upper surface 620. The mold 600 contains an aperture 625 through which a surgical drill or saw can fit. The aperture guides the drill or saw to make the proper hole or cut in the underlying bone 610 as illustrated in FIGS. 21B-D. Dotted lines 632 illustrate where the cut corresponding to the aperture will be made in bone.

Figure 24B:
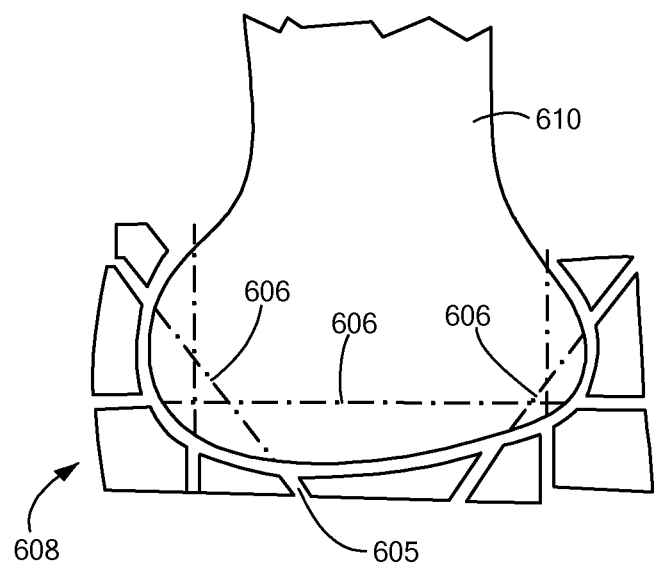
FIG. 24B depicts, in cross-section, an example of a surgical tool containing apertures through which a surgical drill or saw can fit and which guide the drill or saw to make cuts or holes in the bone. Dotted lines represent where the cuts corresponding to the apertures will be made in bone.

FIG. 24B depicts, a mold 608 suitable for use on the femur. As can be appreciated from this perspective, additional apertures are provided to enable additional cuts to the bone surface. The apertures 605 enable cuts 606 to the surface of the femur. The resulting shape of the femur corresponds to the shape of the interior surface of the femoral implant, typically as shown in FIG. 21E. Additional shapes can be achieved, if desired, by changing the size, orientation and placement of the apertures. Such changes would be desired where, for example, the interior shape of the femoral component of the implant requires a different shape of the prepared femur surface.

Turning now to FIG. 25, a variety of illustrations are provided showing a tibial cutting block and mold system. FIG. 25A illustrates the tibial cutting block 2300 in conjunction with a tibia 2302 that has not been resected. In this depiction, the cutting block 2300 consists of at least two pieces. The first piece is a patient specific interior piece 2310 or mold that is designed on its inferior surface 2312 to mate, or substantially mate, with the existing geography of the patient's tibia 2302. The superior surface 2314 and side surfaces 2316 of the first piece 2310 are configured to mate within the interior of an exterior piece 2320. The reusable exterior piece 2320 fits over the interior piece 2310. The system can be configured to hold the mold onto the bone.

The reusable exterior piece has a superior surface 2322 and an inferior surface 2324 that mates with the first piece 2310. The reusable exterior piece 2320 includes cutting guides 2328, to assist the surgeon in performing the tibial surface cut described above. As shown herein a plurality of cutting guides can be provided to provide the surgeon a variety of locations to choose from in making the tibial cut. If necessary, additional spacers can be provided that fit between the first patient configured, or molded, piece 2310 and the second reusable exterior piece, or cutting block, 2320.

The variable nature of the interior piece facilitates obtaining the most accurate cut despite the level of disease of the joint because it positions the exterior piece 2320 such that it can achieve a cut that is perpendicular to the mechanical axis. Either the interior piece 2310 or the exterior piece 2320 can be formed out of any of the materials discussed above in Section II, or any other suitable material. Additionally, a person of skill in the art will appreciate that the invention is not limited to the two piece configuration described herein. The reusable exterior piece 2320 and the patient specific interior piece 2310 can be a single piece that is either patient specific (where manufacturing costs of materials support such a product) or is reusable based on a library of substantially defect conforming shapes developed in response to known or common tibial surface sizes and defects.

The interior piece 2310 is typically molded to the tibia including the subchondral bone and/or the cartilage. The surgeon will typically remove any residual meniscal tissue prior to applying the mold. Optionally, the interior surface 2312 of the mold can include shape information of portions or all of the menisci.

Figure 25A:
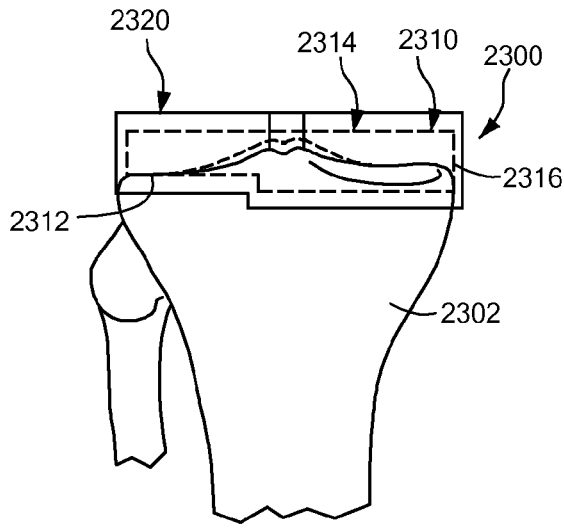
FIGS. 25A-Q illustrate tibial cutting blocks and molds used to create a surface perpendicular to the anatomic axis for receiving the tibial portion of a knee implant.
Figure 25B:
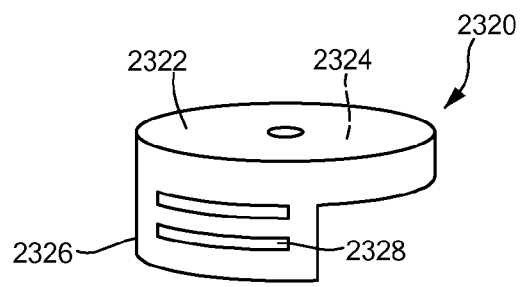
Figure 25C:
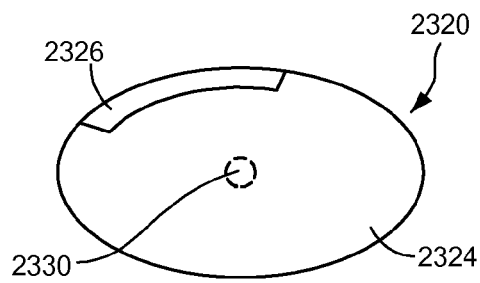
Figure 25D:
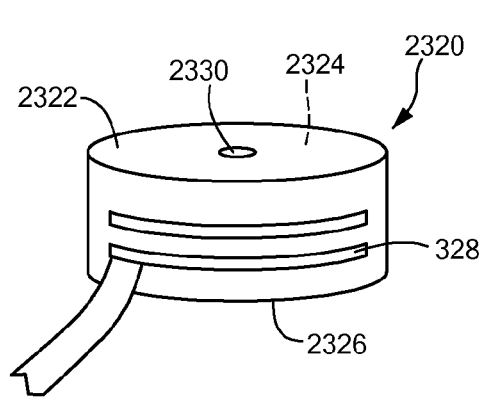

Turning now to FIG. 25B-D, a variety of views of the removable exterior piece 2320. The top surface 2322 of the exterior piece can be relatively flat. The lower surface 2324 which abuts the interior piece conforms to the shape of the upper surface of the interior piece. In this illustration the upper surface of the interior piece is flat, therefore the lower surface 2324 of the reusable exterior surface is also flat to provide an optimal mating surface.

A guide plate 2326 is provided that extends along the side of at least a portion of the exterior piece 2320. The guide plate 2326 provides one or more slots or guides 2328 through which a saw blade can be inserted to achieve the cut desired of the tibial surface. Additionally, the slot, or guide, can be configured so that the saw blade cuts at a line perpendicular to the mechanical axis, or so that it cuts at a line that is perpendicular to the mechanical axis, but has a 4-7° slope in the sagittal plane to match the normal slope of the tibia.

Optionally, a central bore 2330 can be provided that, for example, enables a drill to ream a hole into the bone for the stem of the tibial component of the knee implant.

Figure 25E:
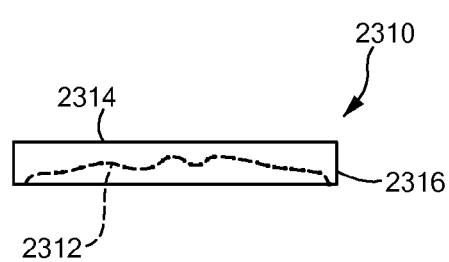
Figure 25F:
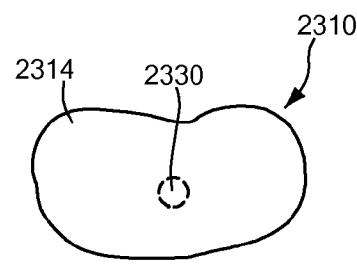
Figure 25G:
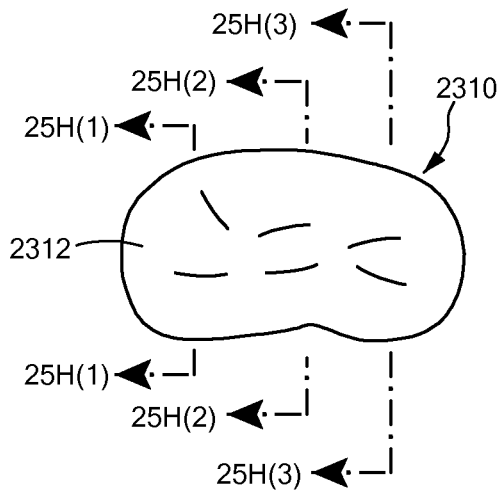
Figure 25H:
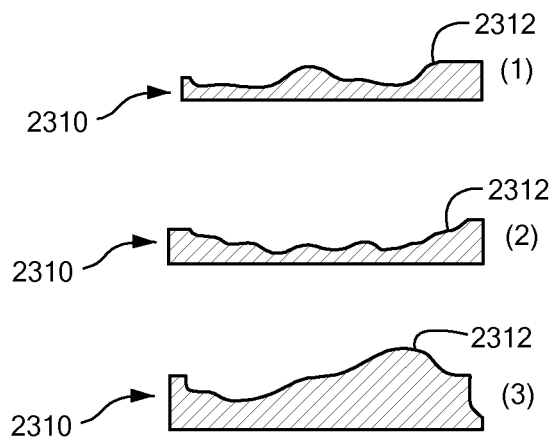

FIGS. 25E-H illustrate the interior, patient specific, piece 2310 from a variety of perspectives. FIG. 25E shows a side view of the piece showing the uniform superior surface 2314 and the uniform side surfaces 2316 along with the irregular inferior surface 2316. The inferior surface mates with the irregular surface of the tibia 2302. FIG. 25F illustrates a superior view of the interior, patient, specific piece of the mold 2310. Optionally having an aperture 2330. FIG. 25G illustrates an inferior view of the interior patient specific mold piece 2310 further illustrating the irregular surface which includes convex and concave portions to the surface, as necessary to achieve optimal mating with the surface of the tibia. FIG. 25H illustrates cross-sectional views of the interior patient specific mold piece 2310. As can be seen in the cross-sections, the surface of the interior surface changes along its length.

As is evident from the views shown in FIGS. 25B and D, the length of the guide plate 2326 can be such that it extends along all or part of the tibial plateau, e.g. where the guide plate 2326 is asymmetrically positioned as shown in FIG. 25B or symmetrical as in FIG. 23D. If total knee arthroplasty is contemplated, the length of the guide plate 2326 typically extends along all of the tibial plateau. If unicompartmental arthroplasty is contemplated, the length of the guide plate typically extends along the length of the compartment that the surgeon will operate on. Similarly, if total knee arthroplasty is contemplated, the length of the molded, interior piece 2310 typically extends along all of the tibial plateau; it can include one or both tibial spines. If unicompartmental arthroplasty is contemplated, the length of the molded interior piece typically extends along the length of the compartment that the surgeon will operate on; it can optionally include a tibial spine.

Figure 25I:
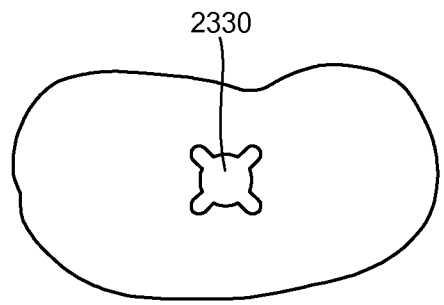

Turning now to FIG. 25I, an alternative embodiment is depicted of the aperture 2330. In this embodiment, the aperture features lateral protrusions to accommodate using a reamer or punch to create an opening in the bone that accepts a stem having flanges.

Figure 25J:
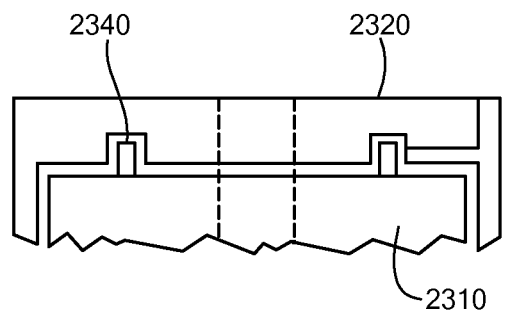
Figure 25K:
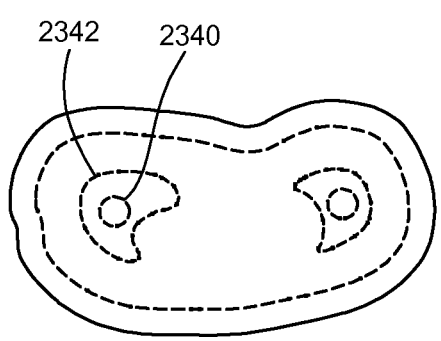
Figure 25L:
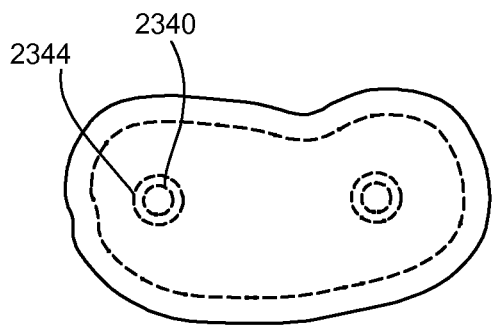
Figure 25Q:
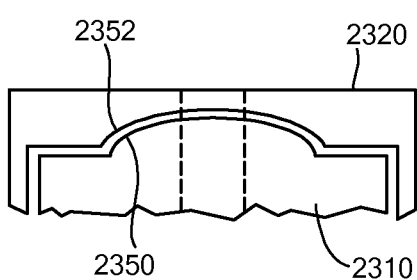
Figure 25Q:
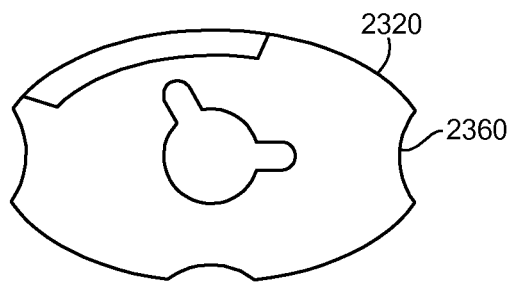
Figure 25Q:
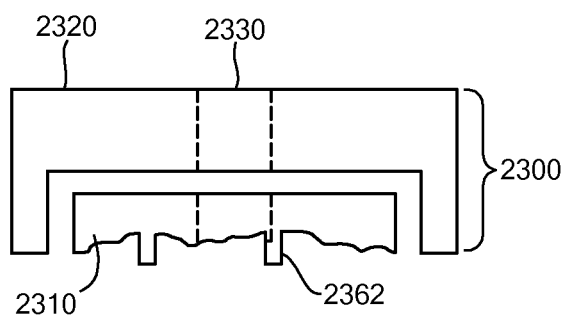
Figure 25Q:
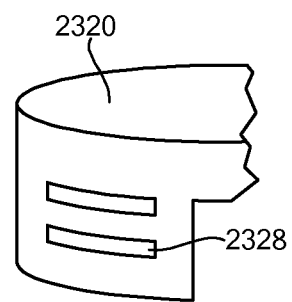
Figure 25Q:
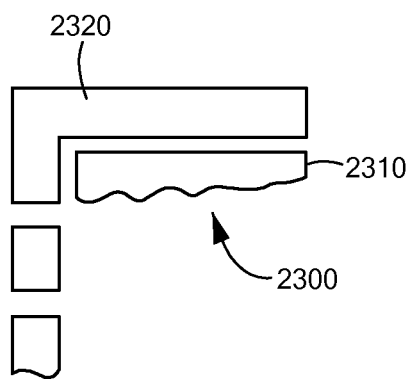

FIGS. 25J and M depict alternative embodiments of the invention designed to control the movement and rotation of the cutting block 2320 relative to the mold 2310. As shown in FIG. 25J a series of protrusions, illustrated as pegs 2340, are provided that extend from the superior surface of the mold. As will be appreciated by those of skill in the art, one or more pegs or protrusions can be used without departing from the scope of the invention. For purposes of illustration, two pegs have been shown in FIG. 25J. Depending on the control desired, the pegs 2340 are configured to fit within, for example, a curved slot 2342 that enables rotational adjustment as illustrated in FIG. 23K or within a recess 2344 that conforms in shape to the peg 2340 as shown in FIG. 25L. As will be appreciated by those of skill in the art, the recess 2344 can be sized to snugly encompass the peg or can be sized larger than the peg to allow limited lateral and rotational movement.

As illustrated in FIG. 25M the surface of the mold 2310 can be configured such that the upper surface forms a convex dome 2350 that fits within a concave well 2352 provided on the interior surface of the cutting block 2320. This configuration enables greater rotational movement about the mechanical axis while limiting lateral movement or translation.

Other embodiments and configurations could be used to achieve these results without departing from the scope of the invention.

As will be appreciated by those of skill in the art, more than two pieces can be used, where appropriate, to comprise the system. For example, the patient specific interior piece 2310 can be two pieces that are configured to form a single piece when placed on the tibia. Additionally, the exterior piece 2320 can be two components. The first component can have, for example, the cutting guide apertures 2328. After the resection using the cutting guide aperture 2328 is made, the exterior piece 2320 can be removed and a secondary exterior piece 2320' can be used which does not have the guide plate 2326 with the cutting guide apertures 2328, but has the aperture 2330 which facilitates boring into the tibial surface an aperture to receive a stem of the tibial component of the knee implant. Any of these designs could also feature the surface configurations shown in FIGS. 25J-M, if desired.

FIG. 25N illustrates an alternative design of the cutting block 2320 that provides additional structures 2360 to protect, for example, the cruciate ligaments, from being cut during the preparation of the tibial plateau. These additional structures can be in the form of indented guides 2360, as shown in FIG. 25N or other suitable structures.

FIG. 25O illustrates a cross-section of a system having anchoring pegs 2362 on the surface of the interior piece 2310 that anchor the interior piece 2310 into the cartilage or meniscal area.

FIGS. 25P AND Q illustrate a device 2300 configured to cover half of a tibial plateau such that it is unicompartmental.

Turning now to FIG. 26, a femoral mold system is depicted that facilitates preparing the surface of the femur such that the finally implanted femoral implant will achieve optimal mechanical and anatomical axis alignment.

Figure 26A:
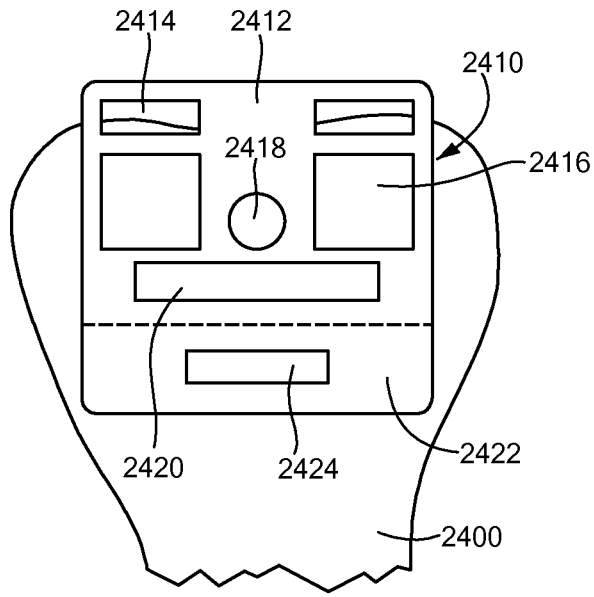
FIGS. 26A-O illustrate femur cutting blocks and molds used to create a surface for receiving the femoral portion of a knee implant.

FIG. 26A illustrates the femur 2400 with a first portion 2410 of the mold placed thereon. In this depiction, the top surface of the mold 2412 is provided with a plurality of apertures. In this instance the apertures consist of a pair of rectangular apertures 2414, a pair of square apertures 2416, a central bore aperture 2418 and a long rectangular aperture 2420. The side surface 2422 of the first portion 2410 also has a rectangular aperture 2424. Each of the apertures is larger than the eventual cuts to be made on the femur so that, in the event the material the first portion of the mold is manufactured from a soft material, such as plastic, it will not be inadvertently cut during the joint surface preparation process. Additionally, the shapes can be adjusted, e.g., rectangular shapes made trapezoidal, to give a greater flexibility to the cut length along one area, without increasing flexibility in another area. As will be appreciated by those of skill in the art, other shapes for the apertures, or orifices, can be changed without departing from the scope of the invention.

Figure 26B:
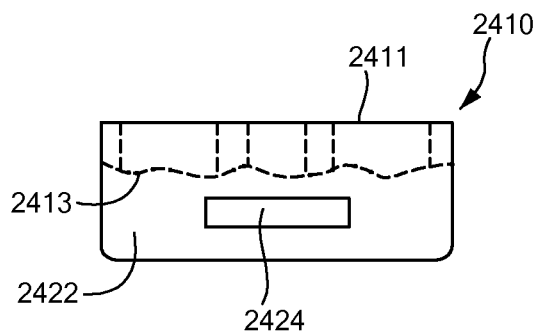

FIG. 26B illustrates a side view of the first portion 2410 from the perspective of the side surface 2422 illustrating the aperture 2424. As illustrated, the exterior surface 2411 has a uniform surface which is flat, or relatively flat configuration while the interior surface 2413 has an irregular surface that conforms, or substantially conforms, with the surface of the femur.

Figure 26C:
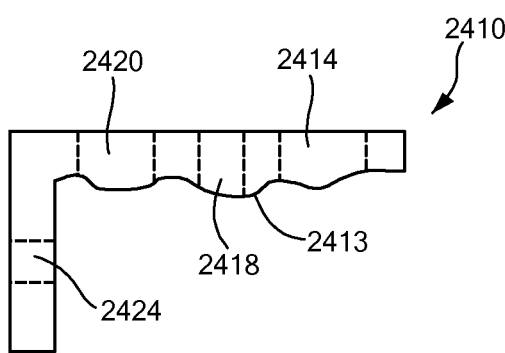
Figure 26D:
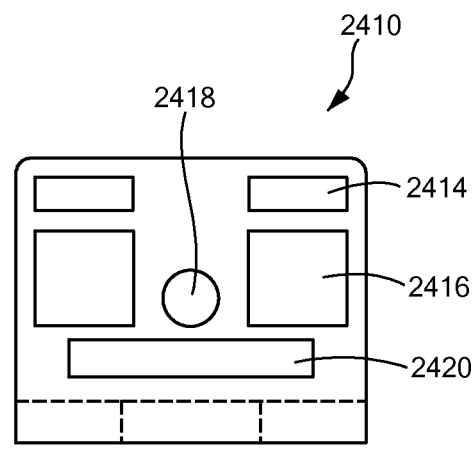

FIG. 26C illustrates another side view of the first, patient specific molded, portion 2410, more particularly illustrating the irregular surface 2413 of the interior. FIG. 26D illustrates the first portion 2410 from a top view. The center bore aperture 2418 is optionally provided to facilitate positioning the first piece and to prevent central rotation.

FIG. 26D illustrates a top view of the first portion 2410. The bottom of the illustration corresponds to an anterior location relative to the knee joint. From the top view, each of the apertures is illustrated as described above. As will be appreciated by those of skill in the art, the apertures can be shaped differently without departing from the scope of the invention.

Turning now to FIG. 26E, the femur 2400 with a first portion 2410 of the cutting block placed on the femur and a second, exterior, portion 2440 placed over the first portion 2410 is illustrated. The second, exterior, portion 2440 features a series of rectangular grooves (2442-2450) that facilitate inserting a saw blade therethrough to make the cuts necessary to achieve the femur shape illustrated in FIG. 21E. These grooves can enable the blade to access at a 90° angle to the surface of the exterior portion, or, for example, at a 45° angle. Other angles are also possible without departing from the scope of the invention.

As shown by the dashed lines, the grooves (2442-2450) of the second portion 2440, overlay the apertures of the first layer.

FIG. 26F illustrates a side view of the second, exterior, cutting block portion 2440. From the side view a single aperture 2450 is provided to access the femur cut. FIG. 26G is another side view of the second, exterior, portion 2440 showing the location and relative angles of the rectangular grooves. As evidenced from this view, the orientation of the grooves 2442, 2448 and 2450 is perpendicular to at least one surface of the second, exterior, portion 2440. The orientation of the grooves 2444, 2446 is at an angle that is not perpendicular to at least one surface of the second, exterior portion 2440. These grooves (2444, 2446) facilitate making the angled chamfer cuts to the femur. FIG. 26H is a top view of the second, exterior portion 2440. As will be appreciated by those of skill in the art, the location and orientation of the grooves will change depending upon the design of the femoral implant and the shape required of the femur to communicate with the implant.

FIG. 26I illustrates a spacer 2401 for use between the first portion 2410 and the second portion 2440. The spacer 2401 raises the second portion relative to the first portion, thus raising the area at which the cut through groove 2424 is made relative to the surface of the femur. As will be appreciated by those of skill in the art, more than one spacer can be employed without departing from the scope of the invention. Spacers can also be used for making the tibial cuts. Optional grooves or channels 2403 can be provided to accommodate, for example, pins 2460 shown in FIG. 26J.

Figure 26J:
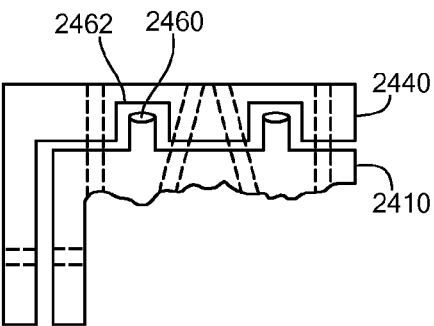

Similar to the designs discussed above with respect to FIG. 25, alternative designs can be used to control the movement and rotation of the cutting block 2440 relative to the mold 2410. As shown in FIG. 26J a series of protrusions, illustrated as pegs 2460, are provided that extend from the superior surface of the mold. These pegs or protrusions can be telescoping to facilitate the use of molds if necessary. As will be appreciated by those of skill in the art, one or more pegs or protrusions can be used without departing from the scope of the invention. For purposes of illustration, two pegs have been shown in FIG. 26J. Depending on the control desired, the pegs 2460 are configured to fit within, for example, a curved slot that enables rotational adjustment similar to the slots illustrated in FIG. 25K or within a recess that conforms in shape to the peg, similar to that shown in FIG. 25L and described with respect to the tibial cutting system. As will be appreciated by those of skill in the art, the recess 2462 can be sized to snugly encompass the peg or can be sized larger than the peg to allow limited lateral and rotational movement.

Figure 26K:
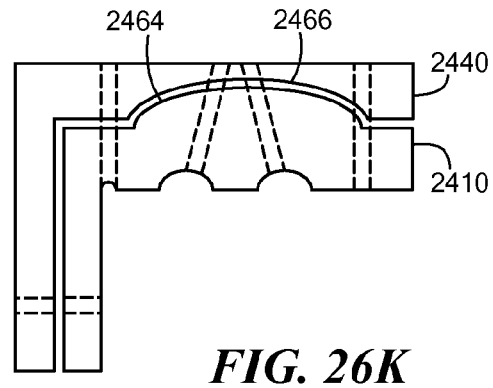
Figure 26L:
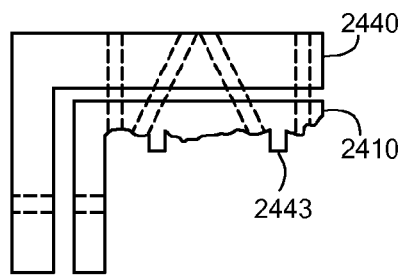
Figure 26M:
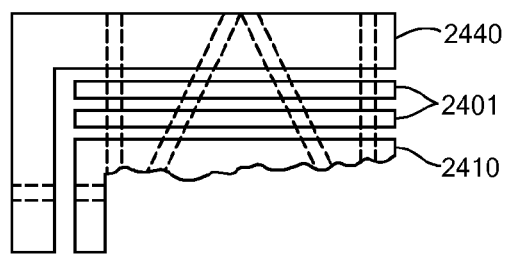

As illustrated in FIG. 26K the surface of the mold 2410 can be configured such that the upper surface forms a convex dome 2464 that fits within a concave well 2466 provided on the interior surface of the cutting block 2440. This configuration enables greater rotational movement about the mechanical axis while limiting lateral movement or translation.

In installing an implant, first the tibial surface is cut using a tibial block, such as those shown in FIG. 26. The patient specific mold is placed on the femur. The knee is then placed in extension and spacers 2470, such as those shown in FIG. 26I, or shims are used, if required, until the joint optimal function is achieved in both extension and flexion. The spacers, or shims, are typically of an incremental size, e.g., 5 mm thick to provide increasing distance as the leg is placed in extension and flexion. A tensiometer can be used to assist in this determination or can be incorporated into the mold or spacers in order to provide optimal results. The design of tensiometers are known in the art and are not included herein to avoid obscuring the invention. Suitable designs include, for example, those described in U.S. Pat. No. 5,630,820 to Todd issued May 20, 1997.

Figure 26N:
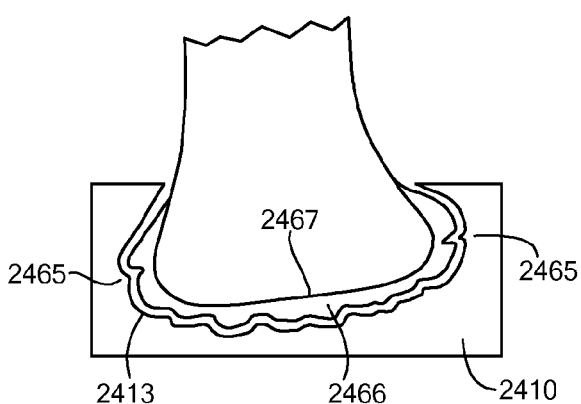
Figure 26O:
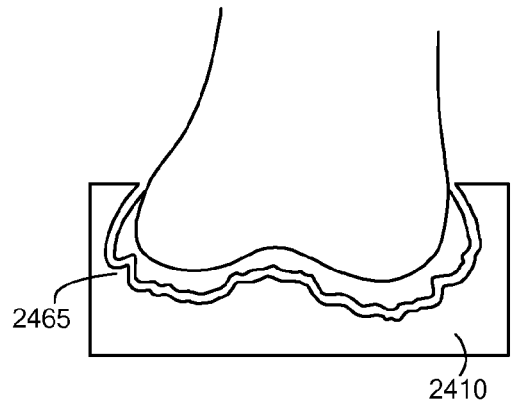

As illustrated in FIGS. 26N (sagittal view) and 26M (coronal view), the interior surface 2413 of the mold 2410 can include small teeth 2465 or extensions that can help stabilize the mold against the cartilage 2466 or subchondral bone 2467.

Turning now to FIG. 27, a variety of illustrations are provided showing a patellar cutting block and mold system. FIGS. 27A-C illustrates the patellar cutting block 2700 in conjunction with a patella 2702 that has not been resected. In this depiction, the cutting block 2700 can consist of only one piece or a plurality of pieces, if desired. The inner surface 2703 is patient specific and designed to mate, or substantially mate, with the existing geography of the patient's patella 2702. Small openings are present 2707 to accept the saw. The mold or block can have only one or multiple openings. The openings can be larger than the saw in order to allow for some rotation or other fine adjustments. FIG. 27A is a view in the sagittal plane S. The quadriceps tendon 2704 and patellar tendon 2705 are shown.

Figure 27A:
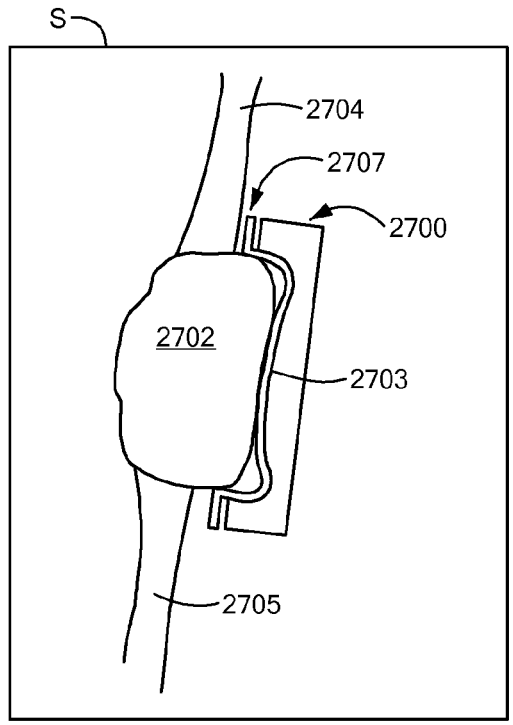
Figure 27B:
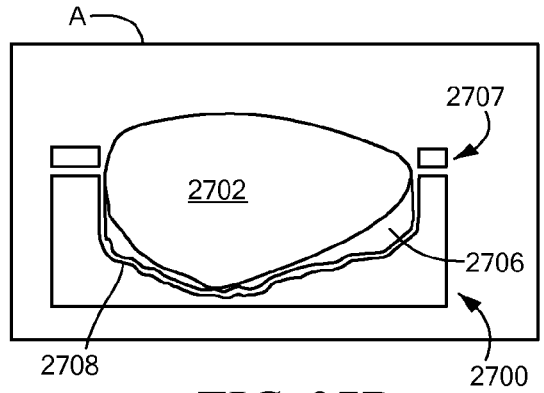
Figure 27C:
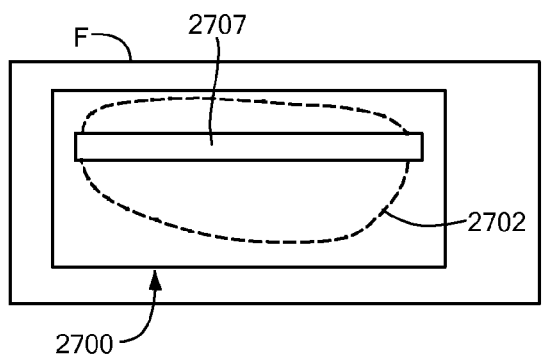

FIG. 27B is a view in the axial plane A. The cartilage 2706 is shown. The mold can be molded to the cartilage or the subchondral bone or combinations thereof. FIG. 27C is a frontal view F of the mold demonstrating the opening for the saw 2707. The dashed line indicates the relative position of the patella 2702.

Figure 27D:
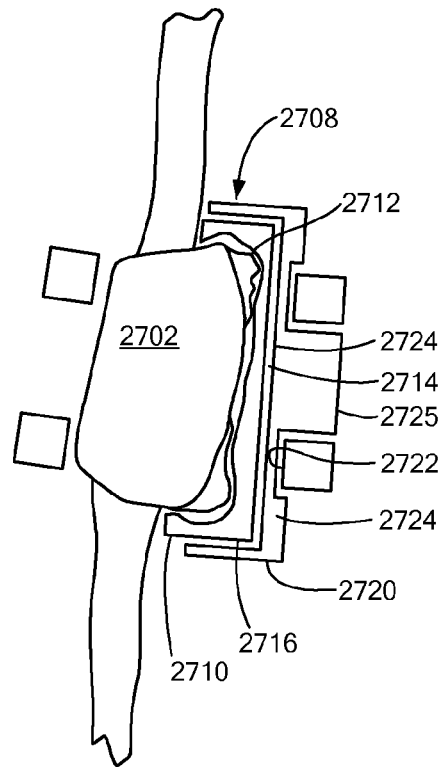

FIGS. 27D (sagittal view) and E (axial view) illustrate a patellar cutting block 2708 in conjunction with a patella 2702 that has not been resected. In this depiction, the cutting block 2708 consists of at least two pieces. The first piece is a patient specific interior piece 2710 or mold that is designed on its inferior surface 2712 to mate, or substantially mate, with the existing geography of the patient's patella 2702. The posterior surface 2714 and side surfaces 2716 of the first piece 2710 are configured to mate within the interior of an exterior piece 2720. The reusable exterior piece 2720 fits over the interior piece 2710 and holds it onto the patella. The reusable exterior piece has an interior surface 2724 that mates with the first piece 2710. The reusable exterior piece 2720 includes cutting guides 2707, to assist the surgeon in performing the patellar surface cut. A plurality of cutting guides can be provided to provide the surgeon a variety of locations to choose from in making the patellar cut. If necessary, additional spacers can be provided that fit between the first patient configured, or molded, piece 2710 and the second reusable exterior piece, or cutting block, 2720.

The second reusable exterior piece, or cutting block, 2720, can have grooves 2722 and extensions 2725 designed to mate with surgical instruments such as a patellar clamp 2726. The patellar clamp 2726 can have ring shaped graspers 2728 and locking mechanisms, for example ratchet-like 2730. The opening 2732 in the grasper fits onto the extension 2725 of the second reusable exterior piece 2720. Portions of a first portion of the handle of the grasper can be at an oblique angle 2734 relative to the second portion of the handle, or curved (not shown), in order to facilitate insertion. Typically the portion of the grasper that will be facing towards the intra-articular side will have an oblique or curved shaped thereby allowing a slightly smaller incision.

The variable nature of the interior piece facilitates obtaining the most accurate cut despite the level of disease of the joint because it positions the exterior piece 2720 in the desired plane. Either the interior piece 2710 or the exterior piece 2720 can be formed out of any of the materials discussed above in Section II, or any other suitable material. Additionally, a person of skill in the art will appreciate that the invention is not limited to the two piece configuration described herein. The reusable exterior piece 2720 and the patient specific interior piece 2710 can be a single piece that is either patient specific (where manufacturing costs of materials support such a product) or is reusable based on a library of substantially defect conforming shapes developed in response to known or common tibial surface sizes and defects.

The interior piece 2710 is typically molded to the patella including the subchondral bone and/or the cartilage.

From this determination, an understanding of the amount of space needed to balance the knee is determined and an appropriate number of spacers is then used in conjunction with the cutting block and mold to achieve the cutting surfaces and to prevent removal of too much bone. Where the cutting block has a thickness of, for example, 10 mm, and each spacer has a thickness of 5 mm, in preparing the knee for cuts, two of the spacers would be removed when applying the cutting block to achieve the cutting planes identified as optimal during flexion and extension. Similar results can be achieved with ratchet or jack like designs interposed between the mold and the cut guide.

ii. Hip Joint

Turning now to FIG. 28, a variety of views showing sample mold and cutting block systems for use in the hip joint are shown. FIG. 28A illustrates femur 2510 with a mold and cutting block system 2520 placed to provide a cutting plane 2530 across the femoral neck 2512 to facilitate removal of the head 2514 of the femur and creation of a surface 2516 for the hip ball prosthesis.

FIG. 28B illustrates a top view of the cutting block system 2520. The cutting block system 2520 includes an interior, patient specific, molded section 2524 and an exterior cutting block surface 2522. The interior, patient specific, molded section 2524 can include a canal 2526 to facilitate placing the interior section 2524 over the neck of the femur. As will be appreciated by those of skill in the art, the width of the canal will vary depending upon the rigidity of the material used to make the interior molded section. The exterior cutting block surface 2522 is configured to fit snugly around the interior section. Additional structures can be provided, similar to those described above with respect to the knee cutting block system, that control movement of the exterior cutting block 2524 relative to interior mold section 2522, as will be appreciated by those of skill in the art. Where the interior section 2524 encompasses all or part of the femoral neck, the cutting block system can be configured such that it aids in removal of the femoral head once the cut has been made by, for example, providing a handle 2501.

Figure 28E:
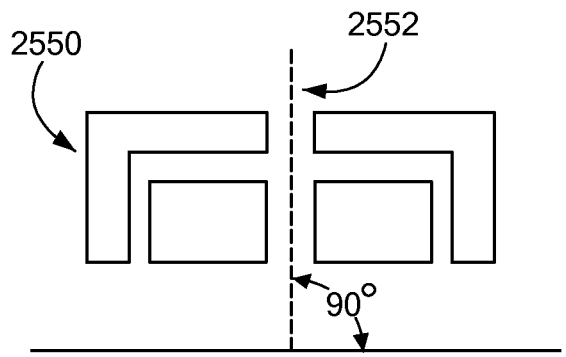
Figure 28F:
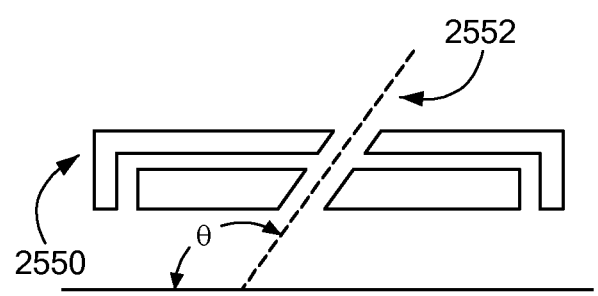
Figure 28G:
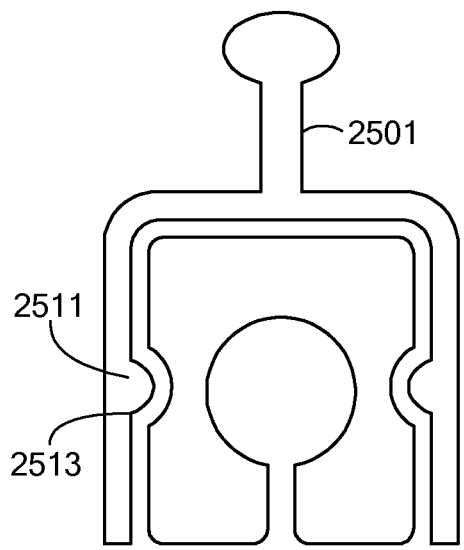
Figure 28H:
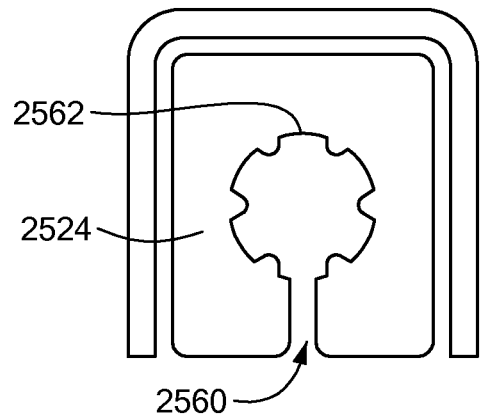

FIG. 28C illustrates a second cutting block system 2550 that can be placed over the cut femur to provide a guide for reaming after the femoral head has been removed using the cutting block shown in FIG. 28A. FIG. 28D is a top view of the cutting block shown in FIG. 28C. As will be appreciated by those of skill in the art, the cutting block shown in FIG. 28C-D, can be one or more pieces. As shown in FIG. 28E, the aperture 2552 can be configured such that it enables the reaming for the post of the implant to be at a 90° angle relative to the surface of femur. Alternatively, as shown in FIG. 28F, the aperture 2552 can be configured to provide an angle other than 90° for reaming, if desired.

Figure 29A:
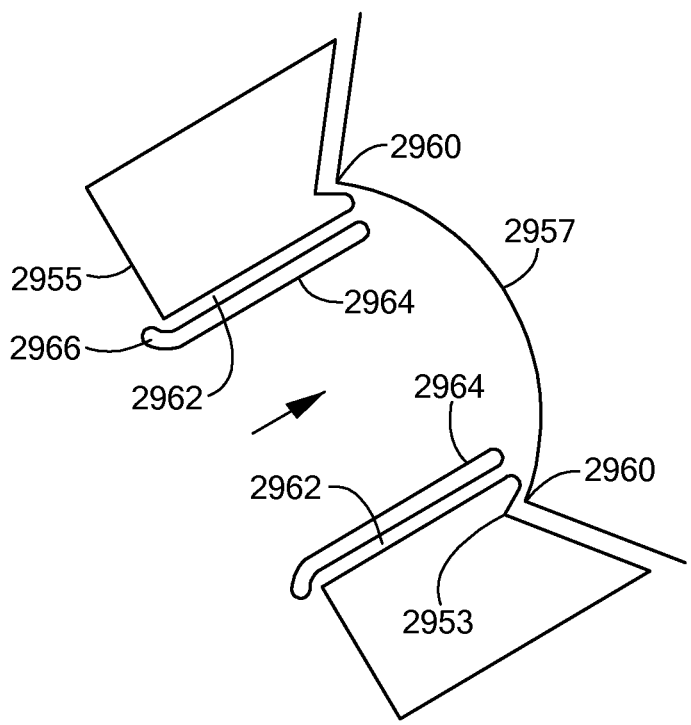
FIG. 29A-D illustrate acetabulum cutting blocks and molds used to create a surface for a hip implant.

FIGS. 29A (sagittal view) and 29B (frontal view, down onto mold) illustrates a mold system 2955 for the acetabulum 2957. The mold can have grooves 2959 that stabilize it against the acetabular rim 2960. Surgical instruments, e.g. reamers, can be passed through an opening in the mold 2956. The side wall of the opening 2962 can guide the direction of the reamer or other surgical instruments. Metal sleeves 2964 can be inserted into the side wall 2962 thereby protecting the side wall of the mold from damage. The metal sleeves 2964 can have lips 2966 or overhanging edges that secure the sleeve against the mold and help avoid movement of the sleeve against the articular surface.

Figure 29B:
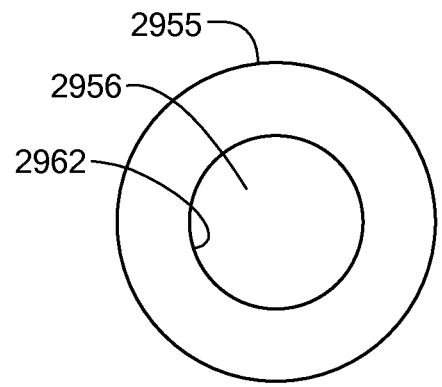
Figure 29C:
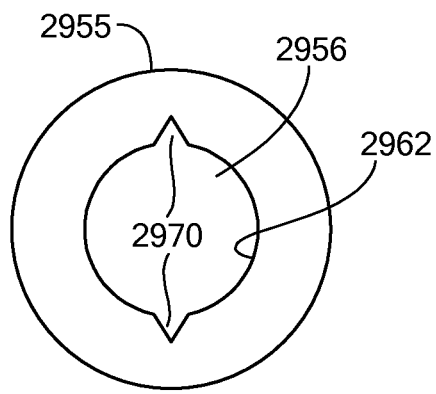

FIG. 29C is a frontal view of the same mold system shown in FIGS. 29A and 29B. A groove 2970 has been added at the 6 and 12 o'clock positions. The groove can be used for accurate positioning or placement of surgical instruments. Moreover, the groove can be useful for accurate placement of the acetabular component without rotational error. Someone skilled in the art will recognize that more than one groove or internal guide can be used in order to not only reduce rotational error but also error related to tilting of the implant. As seen FIG. 29D, the implant 2975 can have little extensions 2977 matching the grooves thereby guiding the implant placement. The extensions 2977 can be a permanent part of the implant design or they can be detachable. Note metal rim 2979 and inner polyethylene cup 2980 of the acetabular component.

Figure 29D:
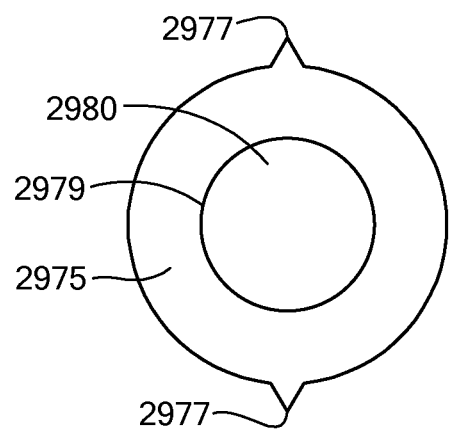

FIG. 29D illustrates a cross-section of a system where the interior surface 2960 of the molded section 2924 has teeth 2962 or grooves to facilitate grasping the neck of the femur.

iii. Small, Focal Cartilage Defect

After identification of the cartilage defect and marking of the skin surface using the proprietary U-shaped cartilage defect locator device as described herein, a 3 cm incision is placed and the tissue retractors are inserted. The cartilage defect is visualized.

A first Lucite block matching the 3D surface of the femoral condyle is placed over the cartilage defect. The central portion of the Lucite block contains a drill hole with an inner diameter of, for example, 1.5 cm, corresponding to the diameter of the base plate of the implant. A standard surgical drill with a drill guide for depth control is inserted through the Lucite block, and the recipient site is prepared for the base component of the implant. The drill and the Lucite block are then removed.

A second Lucite block of identical outer dimensions is then placed over the implant recipient site. The second Lucite block has a rounded, cylindrical extension matching the size of the first drill hole (and matching the shape of the base component of the implant), with a diameter 0.1 mm smaller than the first drill hole and 0.2 mm smaller than that of the base of the implant. The cylindrical extension is placed inside the first drill hole.

The second Lucite block contains a drill hole extending from the external surface of the block to the cylindrical extension. The inner diameter of the second drill hole matches the diameter of the distal portion of the fin-shaped stabilizer strut of the implant, e.g. 3 mm. A drill, e.g. with 3 mm diameter, with a drill guide for depth control is inserted into the second hole and the recipient site is prepared for the stabilizer strut with a four fin and step design. The drill and the Lucite block are then removed.

A plastic model/trial implant matching the 3-D shape of the final implant with a diameter of the base component of 0.2 mm less than that of the final implant and a cylindrical rather than tapered strut stabilizer with a diameter of 0.1 mm less than the distal portion of the final implant is then placed inside the cartilage defect. The plastic model/trial implant is used to confirm alignment of the implant surface with the surrounding cartilage. The surgeon then performs final adjustments.

The implant is subsequently placed inside the recipient site. The anterior fin of the implant is marked with red color and labeled "A." The posterior fin is marked green with a label "P" and the medial fin is color coded yellow with a label "M." The Lucite block is then placed over the implant. A plastic hammer is utilized to advance the implant slowly into the recipient site. A press fit is achieved with help of the tapered and four fin design of the strut, as well as the slightly greater diameter (0.1 mm) of the base component relative to the drill hole. The Lucite block is removed. The tissue retractors are then removed. Standard surgical technique is used to close the 3 cm incision. The same procedure described above for the medial femoral condyle can also be applied to the lateral femoral condyle, the medial tibial plateau, the lateral tibial plateau and the patella. Immediate stabilization of the device can be achieved by combining it with bone cement if desired.

IV. Kits

Also described herein are kits comprising one or more of the methods, systems and/or compositions described herein. In particular, a kit can include one or more of the following: instructions (methods) of obtaining electronic images; systems or instructions for evaluating electronic images; one or more computer means capable of analyzing or processing the electronic images; and/or one or more surgical tools for implanting an articular repair system. The kits can include other materials, for example, instructions, reagents, containers and/or imaging aids (e.g., films, holders, digitizers, etc.).

The following examples are included to more fully illustrate the present invention. Additionally, these examples provide preferred embodiments of the invention and are not meant to limit the scope thereof.

EXAMPLE 1

Design and Construction of a Three-Dimensional Articular Repair System

Figure 13:
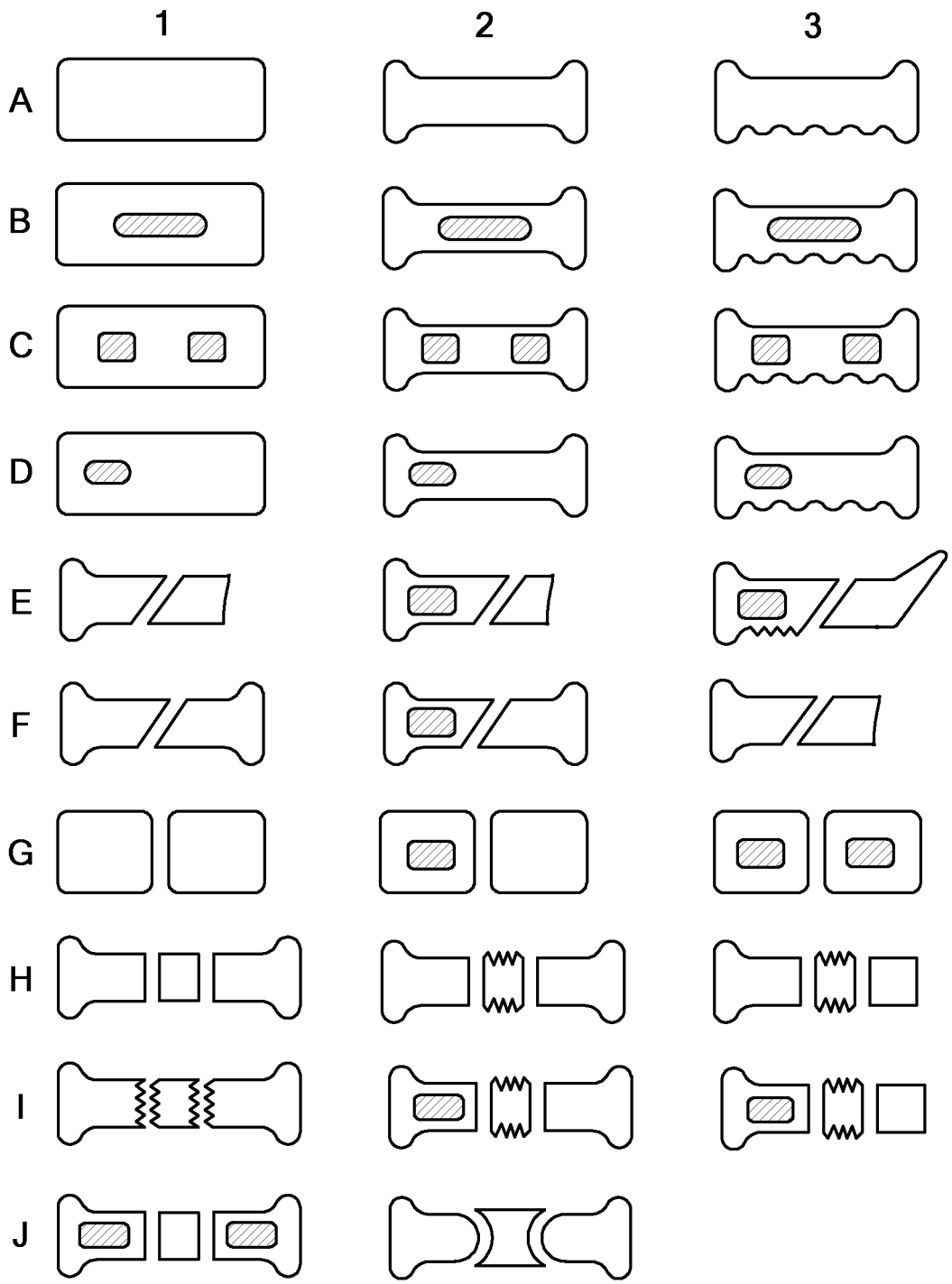
FIGS. 13A-J(1-3) show a variety of cross-sectional views of the inflation devices shown in FIGS. 11 and 12 taken at a position perpendicular to the views shown in FIGS. 11 and 12.

Areas of cartilage are imaged as described herein to detect areas of cartilage loss and/or diseased cartilage. The margins and shape of the cartilage and subchondral bone adjacent to the diseased areas are determined. The thickness of the cartilage is determined. The size of the articular repair system is determined based on the above measurements. (FIGS. 12-14). In particular, the repair system is either selected (based on best fit) from a catalogue of existing, pre-made implants with a range of different sizes and curvatures or custom-designed using CAD/CAM technology. The library of existing shapes is typically on the order of about 30 sizes.

The implant is a chromium cobalt implant (see also FIGS. 12-14 and 17-19). The articular surface is polished and the external dimensions slightly greater than the area of diseased cartilage. The shape is adapted to achieve perfect or near perfect joint congruity utilizing shape information of surrounding cartilage and underlying subchondral bone. Other design features of the implant can include: a slanted (60- to 70-degree angle) interface to adjacent cartilage; a broad-based base component for depth control; a press fit design of base component; a porous coating of base component for ingrowth of bone and rigid stabilization; a dual peg design for large defects implant stabilization, also porous coated (FIG. 12A); a single stabilizer strut with tapered, four fin and step design for small, focal defects, also porous coated (FIG. 12B); and a design applicable to femoral resurfacing (convex external surface) and tibial resurfacing (concave external surface).

EXAMPLE 2

Minimally Invasive, Arthroscopically Assisted Surgical Technique

The articular repair systems are inserted using arthroscopic assistance. The device does not require the 15 to 30 cm incision utilized in unicompartmental and total knee arthroplasties. The procedure is performed under regional anesthesia, typically epidural anesthesia. The surgeon can apply a tourniquet on the upper thigh of the patient to restrict the blood flow to the knee during the procedure. The leg is prepped and draped in sterile technique. A stylette is used to create two small 2 mm ports at the anteromedial and the anterolateral aspect of the joint using classical arthroscopic technique. The arthroscope is inserted via the lateral port. The arthroscopic instruments are inserted via the medial port. The cartilage defect is visualized using the arthroscope. A cartilage defect locator device is placed inside the diseased cartilage. The probe has a U-shape, with the first arm touching the center of the area of diseased cartilage inside the joint and the second arm of the U remaining outside the joint. The second arm of the U indicates the position of the cartilage relative to the skin. The surgeon marks the position of the cartilage defect on the skin. A 3 cm incision is created over the defect. Tissue retractors are inserted and the defect is visualized.

A translucent Lucite block matching the 3D shape of the adjacent cartilage and the cartilage defect is placed over the cartilage defect (FIG. 13). For larger defects, the Lucite block includes a lateral slot for insertion of a saw. The saw is inserted and a straight cut is made across the articular surface, removing an area slightly larger than the diseased cartilage. The center of the Lucite block contains two drill holes with a 7.2 mm diameter. A 7.1 mm drill with drill guide controlling the depth of tissue penetration is inserted via the drill hole. Holes for the cylindrical pegs of the implant are created. The drill and the Lucite block are subsequently removed.

A plastic model/trial implant of the mini-repair system matching the outer dimensions of the implant is then inserted. The trial implant is utilized to confirm anatomic placement of the actual implant. If indicated, the surgeon can make smaller adjustments at this point to improve the match, e.g. slight expansion of the drill holes or adjustment of the cut plane.

The implant is then inserted with the pegs pointing into the drill holes. Anterior and posterior positions of the implant are color-coded; specifically the anterior peg is marked with a red color and a small letter "A", while the posterior peg has a green color and a small letter "P". Similarly, the medial aspect of the implant is color-coded yellow and marked with a small letter "M" and the lateral aspect of the implant is marked with a small letter "L". The Lucite block is then placed on the external surface of the implant and a plastic hammer is used to gently advance the pegs into the drill holes. The pegs are designed to achieve a press fit.

The same technique can be applied in the tibia. The implant has a concave articular surface matching the 3D shape of the tibial plateau. Immediate stabilization of the device can be achieved by combining it with bone cement if desired.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

What is claimed:

1. A surgical system including an articular repair system and a patient-specific surgical tool for use in surgically repairing a joint of a patient, wherein the patient-specific surgical tool comprises:
   a block having a patient-specific surface and first and second guides;
      the patient-specific surface having at least a portion that is substantially a negative of a corresponding portion of a diseased or damaged cartilage surface of the joint of the patient;
      the first and second guides having predetermined positions and orientations relative to the patient-specific surface and being oriented to provide two predetermined drilling or cutting paths that are aligned relative to a biomechanical or anatomical axis of the joint and through a portion of the joint of the patient when the patient-specific surface is placed against the corresponding diseased or damaged cartilage surface of the joint of the patient.

2. The surgical system of claim 1, wherein the articular repair system includes one or more implant components selected for the patient from preexisting systems.

3. The surgical system of claim 2, wherein the selected one or more implant components are further shaped based on electronic image data of the joint of the patient.

4. The surgical system of claim 1, wherein the articular repair system includes one or more implant components designed for the patient using electronic image data of the joint of the patient.

5. The surgical system of claim 1, wherein the joint is one of a hip, knee, ankle, shoulder, elbow and wrist joint.

6. The surgical system of claim 1, wherein the first and second guides are holes configured to accommodate and direct a surgical drill.

7. The surgical system of claim 1, wherein the first and second guides are cutting slots.

8. The surgical system of claim 1, wherein the first guide is a hole configured to accommodate and direct a surgical drill and the second guide is a cutting slot.

9. The surgical system of claim 1, wherein the first and second guides are aligned along distinct cutting planes when the patient-specific surface is fit to the corresponding portion of the diseased or damaged cartilage surface of the joint of the patient.

10. The surgical system of claim 1, wherein the first and second guides are co-planar.

11. The surgical system of claim 1, wherein the first and second guides are not co-planar.

12. The surgical system of claim 1, wherein the first and second guides are aligned along distinct cutting planes when the patient-specific surface is fit to the corresponding portion of the diseased or damaged cartilage surface of the joint.

13. The surgical system of claim 12, wherein the patient-specific surgical tool includes a third guide.

14. The surgical system of claim 13, wherein the third guide is a slot aligned along a second plane to provide a second cutting path that is aligned through a portion of the joint when the patient-specific surface is placed against the corresponding portion of the diseased or damaged cartilage surface of the joint.

15. A surgical system including an articular repair system having one or more implant components and a patient-specific surgical tool for use in surgically repairing a joint of a patient, wherein the patient-specific surgical tool comprises:
   a block having a patient-specific surface and first and second drilling holes;
      the patient-specific surface having at least a portion that is substantially a negative of a corresponding portion of a diseased or damaged articular surface of the joint and having a predetermined position and orientation relative to the corresponding portion;
      the first and second drilling holes having predetermined positions and orientations relative to the patient-specific surface and each having an axis that extends through a portion of the joint when the patient-specific surface is fit to the corresponding portion of the diseased of damaged articular surface of the joint.

16. The surgical system of claim 15, wherein the articular repair system includes one or more implant components selected for the patient from preexisting systems.

17. The surgical system of claim 16, wherein the selected one or more implant components are further shaped based on electronic image data of the joint of the patient.

18. The surgical system of claim 15, wherein the articular repair system includes one or more implant components designed for the patient using electronic image data of the joint of the patient.

19. The surgical system of claim 15, wherein the joint is one of a hip, knee, ankle, shoulder, elbow and wrist joint.

20. The surgical system of claim 15, wherein the block containing the patient-specific surface and the drilling holes are comprised of a single component.

* * * * *